(12) United States Patent
James et al.

(10) Patent No.: US 11,913,685 B2
(45) Date of Patent: *Feb. 27, 2024

(54) COOLING LOOP WITH A SUPERCRITICAL FLUID SYSTEM USING COMPRESSED REFRIGERANT FLUID FLOW WITH A POSITIVE JOULE THOMSON COEFFICIENT

(71) Applicant: Supercritical Fluid Technologies, Inc., Newark, DE (US)

(72) Inventors: Kenneth Joseph James, Newark, DE (US); Brian Jeffrey Waibel, Kennett Square, PA (US); Kenneth Richard Krewson, Allentown, NJ (US); Kim Ferrara, Middletown, DE (US); Curtis Ebersold, Newark, DE (US)

(73) Assignee: Supercritical Fluid Technologies, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/506,353

(22) Filed: Oct. 20, 2021

(65) Prior Publication Data

US 2022/0034555 A1 Feb. 3, 2022

Related U.S. Application Data

(60) Continuation-in-part of application No. 17/313,189, filed on May 6, 2021, now Pat. No. 11,680,735,
(Continued)

(51) Int. Cl.
 F25B 7/00 (2006.01)
 F25B 9/00 (2006.01)
 (Continued)

(52) U.S. Cl.
 CPC .......... *F25B 25/005* (2013.01); *B01D 15/165* (2013.01); *B01D 15/40* (2013.01);
 (Continued)

(58) Field of Classification Search
 CPC ...... B01D 15/165; B01D 15/40; B04C 5/081; B04C 5/085; B04C 9/00; B04C 2009/004;
 (Continued)

(56) References Cited

U.S. PATENT DOCUMENTS 3,322,188 A 5/1967 Ostrander
4,033,140 A 7/1977 Klee et al.
(Continued)

FOREIGN PATENT DOCUMENTS

CA 2917035 A1 1/2015
CN 202802826 U 3/2013
(Continued)

OTHER PUBLICATIONS

Campbell et al., "Supercritical fluid fractionation of petroleum-and-coal-derived mixtures" Analytical Chemistry 58 (11):2247-2251, Sep. 1986.
(Continued)

*Primary Examiner* — Benjamin L Lebron
(74) *Attorney, Agent, or Firm* — Devlin Law Firm LLC; James M. Lennon

(57) ABSTRACT

Provided is a chiller and system that may be utilized in a supercritical fluid chromatography method, wherein a non-polar solvent may replace a portion or all of a polar solvent for the purpose of separating or extracting desired sample molecules from a combined sample/solvent stream. The system may reduce the amount of polar solvent necessary for chromatographic separation and/or extraction of desired samples. The system may incorporate a supercritical fluid chiller, a supercritical fluid pressure-equalizing vessel and a supercritical fluid cyclonic separator. The supercritical fluid chiller allows for efficient and consistent pumping of liquid-phase gases employing off-the-shelf HPLC pumps. The pressure equalizing vessel allows the use of off-the-shelf
(Continued)

HPLC column cartridges. The system may further incorporate the use of one or more disposable cartridges containing silica gel or other suitable medium. The system may also utilize an open loop cooling circuit using fluids with a positive Joule-Thomson coefficient.

19 Claims, 28 Drawing Sheets

Related U.S. Application Data which is a continuation of application No. 16/384,117, filed on Apr. 15, 2019, now Pat. No. 11,022,350, which is a division of application No. 15/784,131, filed on Oct. 14, 2017, now abandoned, which is a continuation of application No. 15/504,313, filed on Feb. 15, 2017, now Pat. No. 10,610,808, said application No. 17/313,189 is a continuation of application No. 15/397,452, filed as application No. PCT/US2015/044306 on Aug. 7, 2015, now Pat. No. 10,765,968.

(60) Provisional application No. 62/408,346, filed on Oct. 14, 2016, provisional application No. 62/276,102, filed on Jan. 7, 2016, provisional application No. 62/274,667, filed on Jan. 4, 2016, provisional application No. 62/274,672, filed on Jan. 4, 2016, provisional application No. 62/274,659, filed on Jan. 4, 2016, provisional application No. 62/274,748, filed on Jan. 4, 2016, provisional application No. 62/039,074, filed on Aug. 19, 2014, provisional application No. 62/039,083, filed on Aug. 19, 2014.

(51) Int. Cl.

| | | |
|---|---|---|
| *F25B 9/10* | (2006.01) | |
| *F25B 25/00* | (2006.01) | |
| *F25B 49/02* | (2006.01) | |
| *G01N 30/20* | (2006.01) | |
| *G01N 30/30* | (2006.01) | |
| *G01N 30/54* | (2006.01) | |
| *B01D 15/16* | (2006.01) | |
| *B01D 15/40* | (2006.01) | |
| *B04C 5/081* | (2006.01) | |
| *B04C 5/085* | (2006.01) | |
| *C07C 45/79* | (2006.01) | |
| *C07C 51/47* | (2006.01) | |
| *C07C 231/24* | (2006.01) | |
| *C09K 5/04* | (2006.01) | |
| *B04C 9/00* | (2006.01) | |
| *C07C 67/56* | (2006.01) | |

(52) U.S. Cl.
CPC .............. *B04C 5/081* (2013.01); *B04C 5/085* (2013.01); *B04C 9/00* (2013.01); *C07C 45/79* (2013.01); *C07C 51/47* (2013.01); *C07C 67/56* (2013.01); *C07C 231/24* (2013.01); *C09K 5/041* (2013.01); *F25B 7/00* (2013.01); *F25B 9/002* (2013.01); *F25B 9/008* (2013.01); *F25B 9/10* (2013.01); *F25B 49/02* (2013.01); *G01N 30/30* (2013.01); *G01N 30/54* (2013.01); *B04C 2009/004* (2013.01); *C09K 2205/106* (2013.01); *C09K 2205/13* (2013.01); *C09K 2205/132* (2013.01); *F25B 2600/2513* (2013.01); *F25B 2700/21171* (2013.01); *G01N 30/20* (2013.01); *Y02P 20/54* (2015.11)

(58) Field of Classification Search
CPC .......... C07C 45/79; C07C 51/47; C07C 67/56; C07C 231/24; C09K 6/041; C09K 2205/106; C09K 2205/13; C09K 2205/132; F25B 7/00; F25B 9/002; F25B 9/008; F25B 9/10; F25B 25/005; F25B 49/02; F25B 2600/2513; F25B 2700/21171; G01N 30/20; G01N 30/30; G01N 30/54
See application file for complete search history.

(56) References Cited

U.S. PATENT DOCUMENTS

| | | |
|---|---|---|
| 4,187,177 A | 2/1980 | Stahl |
| 4,222,414 A | 9/1980 | Achener |
| 4,604,198 A | 8/1986 | Dailey et al. |
| 4,814,089 A | 3/1989 | Kumar |
| 4,845,985 A | 4/1989 | Berger |
| 4,871,453 A | 10/1989 | Kumar |
| 5,060,481 A | 10/1991 | Bartlett et al. |
| 5,147,538 A | 9/1992 | Wright et al. |
| 5,167,930 A | 12/1992 | Fassbender |
| 5,196,575 A | 3/1993 | Sebastian |
| 5,250,195 A | 10/1993 | Winter et al. |
| 5,324,427 A | 6/1994 | Traveset-Masanes et al. |
| 5,384,051 A | 1/1995 | McGinness |
| 5,582,723 A | 12/1996 | Boone et al. |
| 5,601,707 A | 2/1997 | Clay et al. |
| 5,976,381 A | 11/1999 | Lundell et al. |
| 6,001,260 A | 12/1999 | Hatch et al. |
| 6,015,491 A | 1/2000 | Renard et al. |
| 6,086,767 A | 7/2000 | Walters et al. |
| 6,413,428 B1 | 7/2002 | Berger et al. |
| 6,561,767 B2 | 5/2003 | Berger et al. |
| 6,648,609 B2 | 11/2003 | Berger et al. |
| 6,936,165 B2 | 8/2005 | Seydoux et al. |
| 6,982,007 B2 | 1/2006 | Worm et al. |
| 7,013,660 B2 | 3/2006 | Kim |
| 7,048,517 B2 | 5/2006 | Berger et al. |
| 7,083,395 B2 | 8/2006 | Maiefski et al. |
| 7,125,453 B2 | 10/2006 | D'Evelyn et al. |
| 7,937,990 B2 | 5/2011 | Nagaoka et al. |
| 8,173,024 B2 | 5/2012 | Titmas |
| 8,215,922 B2 | 7/2012 | Berger et al. |
| 8,246,834 B2 | 8/2012 | Chordia et al. |
| 8,419,936 B2 | 4/2013 | Berger et al. |
| 10,610,808 B2 | 4/2020 | James et al. |
| 10,765,968 B2 | 9/2020 | James et al. |
| 11,022,350 B2 * | 6/2021 | James .................. C07C 67/56 |
| 2002/0139752 A1 | 10/2002 | Berger et al. |
| 2002/0144949 A1 | 10/2002 | Berger et al. |
| 2003/0215341 A1 | 11/2003 | Maiefski et al. |
| 2004/0096986 A1 | 5/2004 | Klein et al. |
| 2005/0011835 A1 | 1/2005 | Henderson et al. |
| 2005/0247632 A1 | 11/2005 | Ellis et al. |
| 2007/0006609 A1 | 1/2007 | Thomas et al. |
| 2009/0113903 A1 | 5/2009 | Babkin et al. |
| 2010/0077874 A1 | 4/2010 | Kanomata |
| 2010/0326133 A1 | 12/2010 | Beeby et al. |
| 2011/0030186 A1 | 2/2011 | Yamagata et al. |
| 2011/0146302 A1 | 6/2011 | Newman et al. |
| 2011/0306146 A1 | 12/2011 | Sidhu et al. |
| 2011/0315243 A1 | 12/2011 | Hayashi |
| 2012/0122705 A1 | 5/2012 | Ting et al. |
| 2013/0015138 A1 | 1/2013 | Schlake et al. |
| 2013/0180404 A1 | 7/2013 | Fogelman et al. |
| 2013/0289300 A1 | 10/2013 | Yu et al. |
| 2014/0190183 A1 | 7/2014 | Berger et al. |
| 2016/0370036 A1 * | 12/2016 | Herzog ................. F25B 19/005 |
| 2017/0189831 A1 | 7/2017 | James et al. |
| 2017/0246558 A1 | 8/2017 | James et al. |

(56) References Cited

U.S. PATENT DOCUMENTS

| | | |
|---|---|---|
| 2018/0112896 A1 | 4/2018 | James et al. |
| 2020/0056815 A1 | 2/2020 | James et al. |

FOREIGN PATENT DOCUMENTS

| | | |
|---|---|---|
| DE | 2739860 A1 | 3/1979 |
| WO | WO 2005-049170 A1 | 6/2005 |
| WO | WO 2015-000708 A1 | 1/2015 |
| WO | WO 2016-028521 A2 | 2/2016 |
| WO | WO 2018-071884 A1 | 4/2018 |

OTHER PUBLICATIONS

Exergy LLC, "Tube-in-tube heat exchangers". Oct. 21, 2014. https://web.archive.org/web/20141021014616/http://www.exergyllc.com/tube-in-tube-heat-exchangers.html (Year: 2014).

Jentoft et al., "Apparatus for Supercritical Fluid Chromatography with Carbon Dioxide as the Mobile Phase" Analytical Chemistry 44(4): 681-686, Apr. 1972.

Still et al., "Rapid Chromatographic Technique for Preparative Separations with Moderate Resolution" J Org Chem. 43(14):2923-2925, 1978.

Suman S et al., "Cryogenic/sub-ambient cooling of electronics: revisited", The Ninth Intersociety Conference on Thermal and Thermomechanical Phenomena in Electronic Systems, 2004, ITHERM '04, IEEE, (Jan. 1, 2004), doi:10.1109/ITHERM.2004.1319178, ISBN 978-0-7803-8357-9, pp. 224-231.

Widyaparaga A et al., "Study on a wire-type Joule Thomson microcooler with a concentric heat exchanger", Applied Thermal Engineering, Pergamon, Oxford, GB, vol. 30, No. 16, ISSN 1359-4311, (Nov. 1, 2010), pp. 2563-2573, (Jul. 15, 2010).

International Search Report for PCT/US2015/044306, dated Feb. 25, 2016.

International Search Report for PCT/US2017/056696, dated Jan. 30, 2018.

International Search Report for PCT/US2020/012275, dated Mar. 10, 2020.

Examination Report for AU2015305892, dated Sep. 1, 2020.

Examination Report for CA3040469, dated May 13, 2020.

European Search Report for EP15833172, dated Apr. 6, 2018.

European Search Report for EP17860662, dated May 6, 2020.

* cited by examiner

COOLING LOOP WITH A SUPERCRITICAL FLUID SYSTEM USING COMPRESSED REFRIGERANT FLUID FLOW WITH A POSITIVE JOULE THOMSON COEFFICIENT

CROSS-REFERENCE TO RELATED APPLICATIONS

This application is a continuation-in-part of U.S. Non-Provisional application Ser. No. 17/313,189, filed May 6, 2021, which is a continuation application of U.S. Non-Provisional application Ser. No. 16/384,117, filed Apr. 15, 2019, which is a divisional application of U.S. Non-Provisional application Ser. No. 15/784,131, filed Oct. 14, 2017, which is a continuation application of U.S. Non-Provisional application Ser. No. 15/504,313, filed on Feb. 15, 2017, which is a U.S. national phase application under 35 U.S.C. § 371 of International Application No. PCT/US2015/044306, filed on Aug. 7, 2015, which claims the benefit of priority under 35 U.S.C. § 119(e) of U.S. Provisional Application No. 62/039,066, filed on Aug. 19, 2014; U.S. Provisional Application No. 62/039,074, filed on Aug. 19, 2014; and U.S. Provisional Application No. 62/039,083, filed on Aug. 19, 2014, all of which are incorporated herein by reference in their entireties for all purposes. This application is also a continuation application of U.S. Non-Provisional application Ser. No. 15/397,452, filed Jan. 3, 2017, which claims the benefit of priority under 35 U.S.C. § 119(e) of U.S. Provisional Application No. 62/274,659, filed Jan. 4, 2016; U.S. Provisional Application No. 62/274,667, filed Jan. 4, 2016; U.S. Provisional Application No. 62/274,672, filed Jan. 4, 2016; U.S. Provisional Application No. 62/274,748, filed Jan. 4, 2016; U.S. Provisional Application No. 62/276,102, filed Jan. 7, 2016; and U.S. Provisional Application No. 62/408,346, filed Oct. 14, 2016, all of which are incorporated herein by reference in their entireties for all purposes.

FIELD OF THE INVENTION

Provided is a cooling loop refrigeration circuit as part of a larger system, wherein the system requires cooling and/or thermal energy transfer.

BACKGROUND

Cooling systems utilizing the Joule-Thomson effect are well known in the art. The Joule-Thomson effect, also known as a throttling process, refers to the temperature change of a gas or liquid when allowed to expand by passing through a valve of conduit. The temperature change is quantified by the Joule-Thomson coefficient, which may be positive (cooling) or negative (heating). Such systems are described in U.S. Pat. No. 2,991,633 to Simon, which discloses that such systems are employed where it is desired to obtain extremely low temperatures; Joule-Thomson effect cooling devices are capable of producing temperatures as low as −196° C. Simon describes the conventional device as including a thin wall tube or jacket having a closed lower end and a low pressure gas discharge opening adjacent its other end, the jacket being formed of suitable material having good heat transfer properties, such as stainless steel. Simon goes on to describe, as entering the jacket, a small elongated capillary tube extending downwardly, typically in a coiled coil configuration and terminating in a small nozzle. Simon explains that a gas having a Joule-Thomson coefficient which is positive at room temperature, such as nitrogen, may be supplied under high pressure to the capillary tube and will expand through the nozzle, whereby the expansion of the gas to the nozzle causes initial cooling, and the gas then flows upwardly over the convolutions of the tubing thus extracting further heat from the tubing in the nature of a heat exchanger. Eventually, the gas is exhausted to the atmosphere through the low pressure discharge opening of the jacket.

In application to supercritical fluid systems, however, the Joule-Thomson effect has been described in the art as an undesirably problem to be avoided or offset. See U.S. Pat. No. 5,653,884 to Burford et. al. Burford explains that unwanted depressurization occurs in flow restrictor tips in supercritical fluid systems which are designed to regulate and restrict backpressure. Specifically, Burford explains that the reduction in fluid density, combined with the Joule-Thomson cooling effect, occurs at the restrictor tip which can a decrease in the solubility of the sample/species extracted by the supercritical fluid and thus lead to unwanted precipitation and ultimately to undesirably plugging of the restrictor. Burford explains how this undesirable effect had been addressed to date. To avoid restrictor plugging the linear restrictor is heated, as heating the restrictor counteracts the Joule-Thomson cooling effect at the restrictor tip and increases the supercritical fluid solubility of the sample/species having some volatility. Several manufacturers use a heated linear flow restrictor.

Applicants are unaware of a supercritical fluid system that utilizes the same gas source intended for the supercritical fluid extraction/separation process as a refrigerant to be passed through a circuit with heat exchanger that does the oppose of counteract the Joule-Thomson cooling effect. Specifically, applicants are unaware of a supercritical fluid system that embraces the Joule-Thomson effect in order to remove heat from supercritical fluid within the system.

Such a refrigeration circuit within a supercritical fluid system may have many applications but one such application is traditional flash chromatography.

Traditional flash chromatography is a chromatographic separation technique that is used to separate organic reaction mixtures to allow the organic chemist to crudely purify the reaction products and then use these purified products to move on to the next step of an organic synthesis. A typical pharmaceutical synthesis has many reaction steps to get from starting materials to a final product where each of these reaction products needs to be purified before moving on to the next synthetic step. The traditional flash chromatography unit employs multiple organic solvent pumps (200 psi and 200 mls/min maximum operation pressure and flow rate for a traditional flash chromatography unit), a sample injection assembly where a chemist would inject the crude reaction mix for separation, a separation column in the form of a cartridge loaded with a silica or modified silica gel, a UV-VIS detector (or other form of sample detection) to detect and allow for collection of the various fractions of the reaction mix exiting the column, and a collection tray to collect the various fractions of the reaction mixture products.

Traditional flash chromatography uses large amounts of organic solvents (for example, Hexanes, Methylene Chloride, Carbon Tetra Chloride, Acetonitrile, and Chloroform) to elucidate a separation. These solvents are typically 80-90% of the flow stream through the separation column.

In the past, Applicants worked on a supercritical carbon dioxide prechiller system that included a waterless refrigeration system to supply subcooling of liquefied carbon dioxide prior to flowing into a piston-style positive displacement pump. Since this device was created, it has undergone testing with a pump meant to supply high pressure carbon dioxide (e.g. >100 bar) to a supercritical carbon dioxide (scCO$_2$) extraction system. Despite multiple attempts to improve the mechanical behavior of the pump, the system mass flow rates were never proportionate to pump speed. This was indicative of cavitation effects in the flow system comprised of duplex pump heads, each comprised of an inlet check valve, compression piston, and outlet check valve. Applicants made multiple attempts to characterize the system as a function of inlet pressure and temperature. Despite significant effort to characterize the behavior, the pump performance was not repeatable. Moreover, all attempts at linearization via compensation failed.

In all cases, the inlet CO$_2$ temperature was reduced to between 2° C. and 5° C. using the waterless refrigeration system. This was readily within the range of single stage compressor. Traditional flash chromatography applications have migrated to higher pressure systems to improve performance. Higher pressure systems, however, require use of a separation column capable of withstanding higher pressures. Traditional flash chromatography cartridges made of plastic and intended to be disposable are generally unusable in higher pressure (e.g., 'medium pressure') flash chromatography systems.

A heretofore unsolved need exists in the industry for a system that will allow higher performance chromatography using higher solvent flow stream pressures, while still allowing the use of convenient, disposable plastic cartridges prepacked for use as a chromatographic separation column, e.g., pre-filled with silica gel.

SUMMARY

In one aspect, is a cooling loop refrigeration circuit as part of a supercritical fluid (or otherwise compressed fluid) system, wherein the circuit uses compressed refrigerant fluid flow with a positive Joule-Thomson coefficient from the refrigerant's expansion, and commensurate temperature reduction, as it flows through an expansion device (e.g., capillaries, orifices and/or larger diameter channels) in the circuit, thus allowing the refrigerant to absorb thermal energy from a source of supercritical fluid placed in proximity to the expansion device.

The cooling loop refrigeration circuit may be used as supercritical fluid system designed for chemical extraction and separation processes that use no or little solvents compared to prior art techniques such as the system disclosed in International Application No. PCT/US2015/044306, the components of which are further detailed below.

Chiller or Pre-Chiller

In one aspect, provided is a chiller. In some embodiments, the chiller comprises: a) a first refrigerant circuit, comprising: i) a first compressor that pumps refrigerant through the first refrigerant circuit; ii) a first tube-in-tube heat exchanger in fluid communication with the first compressor, wherein the first tube-in-tube heat exchanger comprises an inner lumen and an outer lumen that surrounds the inner lumen, wherein the refrigerant flows through the outer lumen; b) a cryogenic refrigerant circuit in thermodynamic communication with the first refrigerant circuit, the cryogenic refrigerant circuit comprising: i) a second compressor that pumps cryogenic refrigerant through the 30 cryogenic refrigerant circuit; ii) the first tube-in-tube heat exchanger in fluid communication with the second compressor; wherein the cryogenic refrigerant flows through the inner lumen; iii) a second tube-in-tube heat exchanger in fluid communication with the first tube-in-tube heat exchanger; wherein the second tube-in-tube heat exchanger comprises an inner lumen and an outer lumen that surrounds the inner lumen, wherein the cryogenic refrigerant flows through the outer lumen and wherein liquefied gas or supercritical gas flows through the inner lumen; wherein the chiller does not comprise an intervening medium that mediates heat exchange between the first refrigerant circuit and the cryogenic refrigerant circuit and wherein the liquefied gas or supercritical gas exiting the inner lumen of the second tube-in-tube heat exchanger is chilled.

In varying embodiments, the output liquefied gas or supercritical gas is chilled at least about 35 degree C. lower than the input liquefied gas or supercritical gas. In varying embodiments, the refrigerant is selected from the group consisting of R-11, R-12, R-22, R-32, R-114, R-115, R-123, R-124, R-125, R-134A, R-142b, R-143a, R-152a, R-290, R-401A, R-401B, R-404A, R-407C, R-410A, R-409A, R-414B, R-416A, R-422B, R-422D, R-500, R-502, R-507, R-600 and mixtures thereof. In varying embodiments, the cryogenic refrigerant is selected from the group consisting of R-12, R-13, R-22, R-23, R-32, R-115, R 116, R-124, R-125, R-134A, R-142b, R-143a, R-152a, R-218, R-290, R-218, R-401A, R-401B, R-402A, R-402B, R-403B, R-404A, R-408A, R-409A, R-410A, R-414B, R-416A, R-422B, R-407A, R-407C, R-408A, R-409A, R-414B, R-422A, R-422B, R-422C, R-422D, R-500, R-502, R-503, R-508B, R-507, R-508B, R-600a and mixtures thereof. In varying embodiments, the first refrigerant circuit further comprises in fluid communication with the first compressor and the first tube-in-tube heat exchanger: iii) a first expansion valve; and iv) a liquid to air heat exchanger. In varying embodiments, the cryogenic refrigerant circuit further comprises in fluid communication with the second compressor, the first tube-in-tube heat exchanger and the second tube-in-tube heat exchanger: iv) a second expansion valve. In varying embodiments, the chiller comprises a configuration as depicted in FIGS. 3A-3B.

In another aspect, provided are methods of supplying a liquid-phase gas to a liquefied gas or supercritical gas extraction system. In some embodiments, the methods comprise: a) subcooling the liquid-phase gas to a temperature of −10° C. or lower; b) pumping the subcooled liquid-phase gas into a chamber configured for extraction with liquefied gas or supercritical gas extraction, whereby the pumping mass flow rate of the subcooled liquid phase gas is repeatable and proportionate to pump speed. In varying embodiments, the subcooling is performed using a chiller as described above and herein. In varying embodiments, the liquefied gas or supercritical gas is selected from the group consisting of carbon dioxide, n-butane, n-propane, isobutane, dimethyl ether, and mixtures thereof. In varying embodiments, the liquefied gas or supercritical gas is CO$_2$. In varying embodiments, the pumping step employs a positive displacement pump. In varying embodiments, the positive displacement pump is an unmodified high performance liquid chromatography (HPLC) pump. In varying embodiments, the system further comprises a post-pump heater downstream of and in fluid communication with the pump, wherein the post-pump heater heats the liquefied gas or supercritical gas up to an operational temperature. In varying embodiments, the liquefied carbon dioxide is subcooled to a temperature in the range of about −10° C. to about −40° C. In varying embodiments, the liquefied carbon dioxide is subcooled to a temperature in the range of about −20° C. to about −40° C. In varying embodiments, the subcooling of the liquefied gas is performed employing a 2-stage refrigerant-on-refrigerant chiller system. In varying embodiments, the pumping step employs a pump comprising at least one pump head and the method does not comprise separately cooling the at least one pump head. In varying embodiments, the liquefied gas or supercritical gas is pressurized to at least about 145 psi (at least about 10 bar).

In a further aspect, provided is a system comprising a chiller as described above and herein. In some embodiments, the system comprises: a) a tank comprising a gas stored at saturated conditions and a liquid withdrawal means; b) a chiller downstream of and in fluid communication with the tank, wherein the chiller subcools the gas to a temperature of −10° C. or lower; c) a pump downstream of and in fluid communication with the tank and the chiller and a chamber configured for liquefied gas or supercritical gas extraction, wherein the pump comprises the gas at a temperature of −10° C. or lower; wherein the mass flow rate of the subcooled liquid phase gas through the pump is repeatable and proportionate to pump speed. In some embodiments, the gas is selected from the group consisting of carbon dioxide, n-butane, n-propane, isobutane, dimethyl ether, and mixtures thereof. In some embodiments, the pump is a positive displacement pump. In some embodiments, the positive displacement pump is an unmodified high performance liquid chromatography (HPLC) pump.

In various embodiments, the system further comprises a cyclonic separator comprising: a) a cyclone body comprising an inner surface, an outer circumference, a top outlet, a tangential inlet and a bottom outlet, wherein the inner surface comprises a top portion, a middle portion and a bottom portion, wherein: i) the top portion of the inner surface comprises screw threads; ii) the middle portion of the inner surface is cylindrical; iii) the bottom portion of the inner surface comprises a funnel, wherein the funnel has an angle in the range of about 30 degrees to about 60 degrees; and wherein the ratio of the diameter of the outer circumference to the inner diameter of the mid-height of the funnel is in the range of about 3 to about 4; and b) a cap comprising a sintered filter and screw threads, wherein the screw threads of the cap interlock with the screw threads on the inner surface of the top portion of the cyclone body, wherein the cyclonic separator can withstand pressures of at least about 1000 psi, and wherein the body is in fluid communication with the cap. In varying embodiments, the bottom outlet of the body of the cyclonic separator is attached to a collection container, wherein the body is in fluid communication with the collection container. In varying embodiments, the cyclonic separator can withstand pressures of up to about 2000 psi. In varying embodiments, the cyclonic separator can withstand pressures of up to about 1500 psi. In varying embodiments, the thickness of the middle portion and the bottom portion of the cyclone body is at least about 0.30 inches. In varying embodiments, the cyclone body is made of a material selected from the group consisting of: stainless steel and titanium. In varying embodiments, the stainless steel comprises an austenitic nickel-chromium-based alloy or a martensitic nickel-chromium-based alloy. In varying embodiments, the stainless steel comprises less than about 0.1 wt. % carbon. In varying embodiments, the stainless steel comprises at least a 30,000 psi yield strength. In varying embodiments, the stainless steel is selected from the group consisting of American Iron and Steel Institute (AISI) TYPE 304 SS, AISI TYPE 316L, INCONEL® alloy 625, INCONEL® alloy 718, AK Steel 17-4-PH®, HASTELLOY® C-22 and HASTELLOY® C 276. In varying embodiments, the stainless steel is a nickel-chromium superalloy selected from the group consisting of INCONEL® alloy 625, INCONEL® alloy 718, AK Steel 17-4-PH®, HASTELLOY® C-22 and HASTELLOY® C 276. In varying embodiments, the inner surface of the cyclone body is configured to induce or guide a conical cyclone of fluid flowing in from the tangential inlet. In varying embodiments, the inner surface of the cyclone body does not comprise a filter or a porous surface. In varying embodiments, the inner surface of the cyclone body does not comprise one or more baffles. In varying embodiments, the cyclone body does not comprise multiple inlets. In varying embodiments, the sintered filter within the cap comprises a G-5 porosity grade (1-16 microns pore size). In varying embodiments, the funnel has an angle of about 40 degrees; and wherein the ratio of the diameter of the outer circumference to the inner diameter of the mid-height of the funnel is about 3.5. In varying embodiments, the bottom outlet remains open. In varying embodiments, the cyclonic separator is as depicted in any one of FIGS. 13 to 17. In varying embodiments, the system comprises 2 to 8 cyclonic separators, e.g., 2, 3, 4, 5, 6, 7 or 8 cyclonic separators. In varying embodiments, the interior of the cyclonic separator is in fluid connection with atmospheric pressure.

In varying embodiments, the system further comprises a pressure equalizing vessel downstream of and in fluid communication with the chiller and the pump and upstream of and in fluid communication with the cyclonic separator, the pressure equalizing vessel comprising: i) an inner chromatography column comprising stationary phase media; and ii) an outer column that cylindrically surrounds the length of the inner column, wherein the interspace between the inner diameter of the outer column and the outer diameter of the inner chromatography column comprises a width of at least 1 mm, wherein the outer column withstands pressures of at least about 500 psi (about 35 bar), and wherein no part of the inner column is exposed to full internal pressure without balancing external equalizing pressure. In varying embodiments, the interspace between the inner diameter of the outer column and the outer diameter of the inner chromatography column is filled with a supercritical fluid. In varying embodiments, the inner column and the outer column can be concurrently filled with supercritical fluid under a pressure in the range of about 500 psi (about 35 bar) to about 20,000 psi (about 1380 bar). In varying embodiments, the inner column and the outer column can be concurrently filled with supercritical fluid under a pressure in the range of at least about 5076 psi (at least about 350 bar). In varying embodiments, the pressure differential across the inner column from top to bottom is less than the pressure rating of the inner column. In varying embodiments, the pressure differential between the internal space of the inner column and the interspace is at or less than about 200 psi (about 14 bar). In varying embodiments, the pressure within the interspace is higher than the pressure within the internal space of the inner column. In varying embodiments, the inner column comprises an inlet end and an outlet end and the pressure at the inlet end is substantially the same as the pressure at the outlet end. In varying embodiments, the inner column is an off-the-shelf column compatible for use in a flash chromatography system. In varying embodiments, the inner column comprises a size in the range of from about 4 grams to about 350 grams stationary phase media. In varying embodiments, the inner column comprises a diameter in the range of about 0.5 inches to about 3.5 inches and a column length in the range from about 3.5 inches to about 11 inches. In varying embodiments, the stationary phase comprises an average particle size in the range of about 10 to about 100 microns. In varying embodiments, the vessel comprises an inlet adaptor which fits to a female slip or lueR-lock connector. In varying embodiments, the vessel comprises an outlet adaptor which fits to a male slip or lueR-lock connector. In varying embodiments, the outlet adaptor comprises an O-ring that seals around the male slip or lueR-lock connector. In varying embodiments, the inner column comprises an inlet end and an outlet end, wherein neither the inlet end nor the outlet end of the inner column comprises a perforated stopper. In varying embodiments, the interspace comprises a single inlet and no outlet or vent. In varying embodiments, the pressure equalizing column is as depicted in FIGS. 11 and 12.

In varying embodiments, the liquefied gas or supercritical gas is $CO_2$. In varying embodiments, the liquefied gas or supercritical gas is pressurized to at least about 145 psi (10 bar). In varying embodiments, the flow of the supercritical solvent through the system is in the range of about 10 ml/min, e.g., at least about 15 ml/min, 20 ml/min, 25 ml/min, 30 ml/min, 35 ml/min, 40 ml/min, 45 ml/min, or 50 ml/min, to about 300 ml/min. In varying embodiments, the system further pumps a co-solvent. In some embodiments, the co-solvent comprises an alcohol of three or fewer carbon atoms (e.g., methanol, ethanol, propanol, isopropanol) or an acetate of three or fewer carbon atoms (e.g., methyl acetate, ethyl acetate, propyl acetate), or mixtures thereof. In varying embodiments, the system is as depicted in FIG. 1.

In another aspect, provided are methods of performing high pressure separation and/or extraction procedures using a flash chromatography system. In some embodiments, the methods comprise inputting a stream of gas phase supercritical fluid comprising molecules into a chiller as described above and herein.

Pressure Equalizing Vessel

In one aspect, provided is a pressure equalizing chromatography vessel comprising:
i) an inner chromatography column comprising stationary phase media; and
ii) an outer column that cylindrically surrounds the length of the inner column, wherein the interspace between the inner diameter of the outer column and the outer diameter of the inner chromatography column comprises a width of at least 1 mm, wherein the outer column withstands pressures of at least about 500 psi (about 35 bar), and wherein no part of the inner column is exposed to full internal pressure without balancing external equalizing pressure. In varying embodiments, the interspace between the inner diameter of the outer column and the outer diameter of the inner chromatography column is filled with a supercritical fluid. In varying embodiments, the inner column and the outer column can be concurrently filled with supercritical fluid under a pressure in the range of about 500 psi (about 35 bar) to about 20,000 psi (about 1380 bar). In varying embodiments, the inner column and the outer column can be concurrently filled with supercritical fluid under a pressure of at least about 5076 psi (at least about 350 bar). In varying embodiments, the pressure differential across the inner column from top to bottom is less than the pressure rating for the inner column. In varying embodiments, the pressure differential between the internal space of the inner column and the interspace is at or less than about 200 psi (about 14 bar). In varying embodiments, the pressure within the interspace is higher than the pressure within the internal space of the inner column. In varying embodiments, the inner column comprises an inlet end and an outlet end and the pressure at the inlet end is substantially the same as the pressure at the outlet end. In varying embodiments, the inner column is an off-the-shelf column compatible for use in a flash chromatography system. In varying embodiments, the inner column comprises a size in the range of from about 4 grams to about 350 grams stationary phase media. In varying embodiments, the inner column comprises a diameter in the range of about 0.5 inches to about 3.5 inches and a column length in the range from about 3.5 inches to about 11 inches. In varying embodiments, the stationary phase comprises an average particle size in the range of about 10 to about 100 microns. In varying embodiments, the vessel comprises an inlet adaptor which fits to a female slip or lueR-lock connector. In varying embodiments, the vessel comprises an outlet adaptor which fits to a male slip or lueR-lock connector. In varying embodiments, the outlet adaptor comprises an O-ring that seals around the male slip or lueR-lock connector. In varying embodiments, the inner column comprises an inlet end and an outlet end, wherein neither the inlet end nor the outlet end of the inner column comprises a perforated stopper. In varying embodiments, the interspace comprises a single inlet and no outlet or vent. In varying embodiments, the pressure equalizing column is as depicted in FIGS. 11 and 12.

In another aspect, provided is a chromatography system comprising the pressure equalizing vessel as described above and herein, wherein the system is pressurized and pumps a supercritical solvent. In some embodiments, the system further comprises a supercritical solvent pump upstream of and in fluid communication with the pressure equalizing vessel and a chiller upstream of and in fluid communication with the pump, wherein the chiller reduces the temperature of the supercritical solvent to about $-5°$ C. or lower, e.g., about $-10°$ C. $-15°$ C., $-20°$ C., $-25°$ C., or lower. In some embodiments, the chiller comprises: a) a first refrigerant circuit, comprising: i) a first compressor that pumps refrigerant through the first refrigerant circuit; ii) a first tube-in-tube heat exchanger in fluid communication with the first compressor, wherein the first tube-in-tube heat exchanger comprises an inner lumen and an outer lumen that surrounds the inner lumen, wherein the refrigerant flows through the outer lumen; b) a cryogenic refrigerant circuit in thermodynamic communication with the first refrigerant circuit, the cryogenic refrigerant circuit comprising: i) a second compressor that pumps cryogenic refrigerant through the cryogenic refrigerant circuit; ii) the first tube-in-tube heat exchanger in fluid communication with the second compressor; wherein the cryogenic refrigerant flows through the inner lumen; iii) a second tube-in-tube heat exchanger in fluid communication with the first tube-in-tube heat exchanger; wherein the second tube-in-tube heat exchanger comprises an inner lumen and an outer lumen that surrounds the inner lumen, wherein the cryogenic refrigerant flows through the outer lumen and wherein liquefied gas or supercritical gas flows through the inner lumen; wherein the chiller does not comprise an intervening medium that mediates heat exchange between the first refrigerant circuit and the cryogenic refrigerant circuit and wherein the liquefied gas or supercritical gas exiting the inner lumen of the second tube-in-tube heat exchanger is chilled. In varying embodiments, the output liquefied gas or supercritical gas is chilled at least about $35°$ C. lower than the input liquefied gas or supercritical gas. In varying embodiments, the refrigerant is selected from the group consisting of R-11, R-12, R-22, R-32, R-114, R-115, R-123, R-124, R-125, R-134A, R-142b, R-143a, R-152a, R-290, R-401A, R-401B, R-404A, R-407C, R-410A, R-409A, R-414B, R-416A, R-422B, R-422D, R-500, R-502, R-507, R-600 and mixtures thereof. In varying embodiments, the cryogenic refrigerant is selected from the group consisting of R-12, R-13, R-22, R-23, R-32, R-115, R-116, R-124, R-125, R-134A, R-142b, R-143a, R-152a, R-218, R-290, R-218, R-401A, R-401B, R-402A, R-402B, R-403B, R-404A, R-408A, R-409A, R-410A, R-414B, R-416A, R-422B, R-407A, R-407C, R-408A, R-409A, R-414B, R-422A, R-422B, R-422C, R-422D, R-500, R-502, R-503, R-508B, R-507, R-508B, R-600a and mixtures thereof. In varying embodiments, the first refrigerant circuit further comprises in fluid communication with the first compressor and the first tube-in-tube heat exchanger: iii) a first expansion valve; and iv) a liquid to air heat exchanger. In varying embodiments, the cryogenic refrigerant circuit further comprises in fluid communication with the second compressor, the first tube-in-tube heat exchanger and the second tube-in-tube heat exchanger: iv) a second expansion valve. In varying embodiments, the chiller comprises a configuration as depicted in FIGS. 3A-3B. In some embodiments, the system comprises: a) a tank comprising a gas stored at saturated conditions and a liquid withdrawal means; b) a chiller in fluid communication with the tank, wherein the chiller subcools the gas to a temperature of −10° C. or lower; c) a pump in fluid communication with the tank and a chamber configured for liquefied gas or supercritical gas extraction, wherein the pump comprises the gas at a temperature of −10° C. or lower; wherein the mass flow rate of the subcooled liquid phase gas through the pump is repeatable and proportionate to pump speed. In some embodiments, the gas is selected from the group consisting of carbon dioxide, n-butane, n-propane, isobutane, dimethyl ether, and mixtures thereof. In some embodiments, the pump is a positive displacement pump. In some embodiments, the positive displacement pump is an unmodified high performance liquid chromatography (HPLC) pump. In varying embodiments, the system further comprises a post-pump heater downstream of and in fluid communication with the pump, wherein the post-pump heater heats the liquefied gas or supercritical gas up to an operational temperature.

In varying embodiments, the supercritical fluid is $CO_2$. In varying embodiments, the flow of the supercritical solvent through the system is in the range of about 10 ml/min, e.g., at least about 15 ml/min, 20 ml/min, 25 ml/min, 30 ml/min, 35 ml/min, 40 ml/min, 45 ml/min, or 50 ml/min, to about 300 ml/min. In varying embodiments, the system further pumps a co-solvent. In some embodiments, the co-solvent comprises an alcohol of 3 or fewer carbon atoms (e.g., methanol, ethanol, propanol, isopropanol) or an acetate of 3 or fewer carbon atoms (e.g., methyl acetate, ethyl acetate, propyl acetate), or mixtures thereof. In varying embodiments, the system is as depicted in FIG. 1.

In varying embodiments, the system further comprises a cyclonic separator downstream of and in fluid communication with the pressure equalizing vessel, the cyclonic separator comprising:
  a) a cyclone body comprising an inner surface, an outer circumference, a top outlet, a tangential inlet and a bottom outlet, wherein the inner surface comprises a top portion, a middle portion and a bottom portion, wherein: i) the top portion of the inner surface comprises screw threads; ii) the middle portion of the inner surface is cylindrical; iii) the bottom portion of the inner surface comprises a funnel, wherein the funnel has an angle in the range of about 30 degrees to about 60 degrees; and wherein the ratio of the diameter of the outer circumference to the inner diameter of the mid-height of the funnel is in the range of about 3 to about 4; and b) a cap comprising a sintered filter and screw threads, wherein the screw threads of the cap interlock with the screw threads on the inner surface of the top portion of the cyclone body, wherein the cyclonic separator can withstand pressures of at least about 1000 psi, and wherein the body is in fluid communication with the cap. In varying embodiments, the bottom outlet of the body is attached to a collection container, wherein the body is in fluid communication with the collection container. In some embodiments, the cyclonic separator can withstand pressures of up to about 10,000 psi, e.g., up to about 5000 psi, e.g., up to about 2000 psi, e.g., up to about 1900 psi, 1800 psi, 1700 psi, 1600 psi, or 1500 psi. In varying embodiments, the thickness of the middle portion and the bottom portion of the cyclone body is at least about 0.30 inches, e.g., at least about 0.31, 0.32, 0.33, 0.34, 0.35, 0.36, 0.37, 0.375, 0.38, 0.39, 0.40 inches. In varying embodiments, the cyclone body is made of a material selected from the group consisting of: stainless steel and titanium. In varying embodiments, the stainless steel comprises an austenitic nickel-chromium-based alloy or a martensitic nickel-chromium-based alloy. In varying embodiments, the stainless steel comprises less than about 0.1 wt. % carbon. In varying embodiments, the stainless steel comprises at least a 30,000 psi yield strength. In varying embodiments, the stainless steel is selected from the group consisting of American Iron and Steel Institute (AISI) TYPE 304 SS, AISI TYPE 316L, INCONEL®, alloy 625, INCONEL® alloy 718, AK Steel 17-4-PH®, HASTELLOY® C-22 and HASTELLOY® C-276. In varying embodiments, the stainless steel is a nickel-chromium superalloy selected from the group consisting of INCONEL® alloy 625, INCONEL® alloy 718, HASTELLOY® C-22 and HASTELLOY® C-276. In some embodiments, the inner surface of the cyclone body is configured to induce or guide a conical cyclone of fluid flowing in from the tangential inlet. In varying embodiments, the inner surface of the cyclone body does not comprise a filter or a porous surface. In varying embodiments, the inner surface of the cyclone body does not comprise one or more baffles. In some embodiments, the cyclone body does not comprise multiple inlets. In some embodiments, the sintered filter within the cap comprises a G-5 porosity grade (1-16 microns pore size). In some embodiments, the funnel has an angle of about 40 degrees; and the ratio of the diameter of the outer circumference to the inner diameter of the mid-height of the funnel is about 3.5. In varying embodiments, the bottom outlet remains open. In some embodiments, the cyclonic separator is as depicted in any one of FIGS. 13 to 17.

In a further aspect, provided is a chromatography system comprising one or more cyclonic separators as described above and herein, wherein the chromatography system is pressurized and pumps a supercritical solvent. In varying embodiments, the system comprises 2 to 8 cyclonic separators, e.g., 2, 3, 4, 5, 6, 7 or 8 cyclonic separators. In varying embodiments, the interior of the cyclonic separator is in fluid connection with atmospheric pressure.

In another aspect, provided are methods of performing high pressure separation and/or extraction procedures using a flash chromatography system, comprising separating sample in a supercritical fluid mobile phase in the inner chromatography column of the pressure equalizing vessel as described above and herein.

Cyclonic Separator

In one aspect, provided is a cyclonic separator comprising: a) a cyclone body comprising an inner surface, an outer circumference, a top outlet, a tangential inlet and a bottom outlet, wherein the inner surface comprises a top portion, a middle portion and a bottom portion, wherein: i) the top portion of the inner surface comprises screw threads; ii) the middle portion of the inner surface is cylindrical; iii) the bottom portion of the inner surface comprises a funnel, wherein the funnel has an angle in the range of about 30 degrees to about 60 degrees; and wherein the ratio of the diameter of the outer circumference to the inner diameter of the mid-height of the funnel is in the range of about 3 to about 4; and b) a cap comprising a sintered filter and screw threads, wherein the screw threads of the cap interlock with the screw threads on the inner surface of the top portion of the cyclone body, wherein the cyclonic separator can withstand pressures of at least about 1000 psi, and wherein the body is in fluid communication with the cap. In varying embodiments, the bottom outlet of the body is attached to a collection container, wherein the body is in fluid communication with the collection container. In some embodiments, the cyclonic separator can withstand pressures of up to about 10,000 psi, e.g., up to about 5000 psi, e.g., up to about 2000 psi, e.g., up to about 1900 psi, 1800 psi, 1700 psi, 1600 psi, or 1500 psi. In varying embodiments, the thickness of the middle portion and the bottom portion of the cyclone body is at least about 0.30 inches, e.g., at least about 0.31, 0.32, 0.33, 0.34, 0.35, 0.36, 0.37, 0.375, 0.38, 0.39, 0.40 inches. In varying embodiments, the cyclone body is made of a material selected from the group consisting of: stainless steel and titanium. In varying embodiments, the stainless steel comprises an austenitic nickel-chromium-based alloy or a martensitic nickel-chromium-based alloy. In varying embodiments, the stainless steel comprises less than about 0.1 wt. % carbon. In varying embodiments, the stainless steel comprises at least a 30,000 psi yield strength. In varying embodiments, the stainless steel is selected from the group consisting of American Iron and Steel Institute (AISI) TYPE 304 SS, AISI TYPE 316L, INCONEL® alloy 625, INCONEL® alloy 718, AK Steel 17-4-PH®, HASTELLOY® C-22 and HASTELLOY® C-276. In varying embodiments, the stainless steel is a nickel-chromium superalloy selected from the group consisting of INCONEL® alloy 625, INCONEL® alloy 718, HASTELLOY® C-22 and HASTELLOY® C-276. In some embodiments, the inner surface of the cyclone body is configured to induce or guide a conical cyclone of fluid flowing in from the tangential inlet. In varying embodiments, the inner surface of the cyclone body does not comprise a filter or a porous surface. In varying embodiments, the inner surface of the cyclone body does not comprise one or more baffles. In some embodiments, the cyclone body does not comprise multiple inlets. In some embodiments, the sintered filter within the cap comprises a G-5 porosity grade (1-16 microns pore size). In some embodiments, the funnel has an angle of about 40 degrees; and the ratio of the diameter of the outer circumference to the inner diameter of the mid-height of the funnel is about 3.5. In varying embodiments, the bottom outlet remains open. In some embodiments, the cyclonic separator is as depicted in any one of FIGS. 13 to 17.

In a further aspect, provided is a chromatography system comprising one or more cyclonic separators as described above and herein, wherein the chromatography system is pressurized and pumps a supercritical solvent. In varying embodiments, the system comprises 2 to 8 cyclonic separators, e.g., 2, 3, 4, 5, 6, 7 or 8 cyclonic separators. In varying embodiments, the interior of the cyclonic separator is in fluid connection with atmospheric pressure.

In varying embodiments, the chromatography system further comprises a pressure equalizing vessel upstream of and in fluid communication with the cyclonic separator, the pressure equalizing vessel comprising: i) an inner chromatography column comprising stationary phase media; and ii) an outer column that cylindrically surrounds the length of the inner column, wherein the interspace between the inner diameter of the outer column and the outer diameter of the inner chromatography column comprises a width of at least 1 mm, wherein the outer column withstands pressures of at least about 500 psi (about 35 bar), and wherein no part of the inner column is exposed to full internal pressure without balancing external equalizing pressure. In varying embodiments, the interspace has a width of up to about 2, 3, 4, 5, 6, 7, 8, 9, 10, 11, 12, 13, 14, 15, 16, 17, 18, 19 or 20 mm. In varying embodiments of the pressure equalizing vessel, the interspace between the inner diameter of the outer column and the outer diameter of the inner chromatography column is filled with a supercritical fluid. In some embodiments, the inner column and the outer column can be concurrently filled with supercritical fluid under a pressure in the range of about 500 psi (about 35 bar) to about 20,000 psi (about 1380 bar). In some embodiments, the inner column and the outer column can be concurrently filled with supercritical fluid under a pressure in the range of at least about 5076 psi (at least about 350 bar). In some embodiments, the pressure differential across the inner column from top to bottom is less than the pressure rating of the inner column. Generally, the pressure differential between the internal space of the inner column and the interspace is less than the pressure rating of the inner column. In some embodiments, the pressure differential between the internal space of the inner column and the interspace is at or less than about 200 psi (about 14 bar). In some embodiments, the pressure within the interspace is higher than the pressure within the internal space of the inner column. In some embodiments, the inner column comprises an inlet end and an outlet end and the pressure at the inlet end is substantially the same as the pressure at the outlet end. In some embodiments, the inner column is an off-the-shelf column compatible for use in a flash chromatography system. In some embodiments, the inner column comprises a size in the range of from about 4 grams to about 350 grams stationary phase media. In some embodiments, the inner column comprises a diameter in the range of about 0.5 inches to about 3.5 inches and a column length in the range from about 3.5 inches to about 11 inches. In some embodiments, the stationary phase comprises an average particle size in the range of about 10 to about 100 microns, e.g., in the range of about 20 to about 80 microns. In some embodiments, the pressure equalizing vessel comprises an inlet adaptor which fits to a female slip or lueR-lock connector. In some embodiments, the pressure equalizing vessel comprises an outlet adaptor which fits to a male slip or lueR-lock connector. In some embodiments, the outlet adaptor comprises an O-ring that seals around the male slip or lueR-lock connector. In some embodiments, the inner column comprises an inlet end and an outlet end, wherein neither the inlet end nor the outlet end of the inner column comprises a perforated stopper. In some embodiments, the interspace comprises a single inlet and no outlet or vent. In some embodiments, the pressure equalizing column is as depicted in FIGS. 11 and 12.

In varying embodiments, the chromatography system further comprises a supercritical solvent pump and a chiller in fluid communication with and upstream of the pump and the cyclonic separator, wherein the chiller reduces the temperature of the supercritical solvent to about −5° C. or lower, e.g., about −10° C., −15° C., −20° C., −25° C. or lower.

In some embodiments, the chiller comprises: a) a first refrigerant circuit, comprising: i) a first compressor that pumps refrigerant through the first refrigerant circuit; ii) a first tube-in-tube heat exchanger in fluid communication with the first compressor, wherein the first tube-in-tube heat exchanger comprises an inner lumen and an outer lumen that surrounds the inner lumen, wherein the refrigerant flows through the outer lumen; b) a cryogenic refrigerant circuit in thermodynamic communication with the first refrigerant circuit, the cryogenic refrigerant circuit comprising: i) a second compressor that pumps cryogenic refrigerant through the cryogenic refrigerant circuit; ii) the first tube-in-tube heat exchanger in fluid communication with the second compressor; wherein the cryogenic refrigerant flows through the inner lumen; iii) a second tube-in-tube heat exchanger in fluid communication with the first tube-in-tube heat exchanger; wherein the second tube-in-tube heat exchanger comprises an inner lumen and an outer lumen that surrounds the inner lumen, wherein the cryogenic refrigerant flows through the outer lumen and wherein liquefied gas or supercritical gas flows through the inner lumen; wherein the chiller does not comprise an intervening medium that mediates heat exchange between the first refrigerant circuit and the cryogenic refrigerant circuit and wherein the liquefied gas or supercritical gas exiting the inner lumen of the second tube-in-tube heat exchanger is chilled. In varying embodiments, the output liquefied gas or supercritical gas is chilled at least about 35° C. lower than the input liquefied gas or supercritical gas. In varying embodiments, the refrigerant is selected from the group consisting of R-11, R-12, R-22, R-32, R-114, R-115, R-123, R-124, R-125, R-134A, R-142b, R-143a, R-152a, R-290, R-401A, R-401B, R-404A, R-407C, R-410A, R-409A, R-414B, R-416A, R-422B, R-422D, R-500, R-502, R-507, R-600 and mixtures thereof. In varying embodiments, the cryogenic refrigerant is selected from the group consisting of R-12, R-13, R-22, R-23, R-32, R-115, R-116, R-124, R-125, R-134A, R-142b, R-143a, R-152a, R-218, R-290, R-218, R-401A, R-401B, R-402A, R-402B, R-403B, R-404A, R-408A, R-409A, R-410A, R-414B, R-416A, R-4228, R-407A, R-407C, R-408A, R-409A, R-414B, R-422A, R-422B, R-422C, R-422D, R-500, R-502, R-503, R-5088, R-507, R-5088, R-600a and mixtures thereof. In varying embodiments, the first refrigerant circuit further comprises in fluid communication with the first compressor and the first tube-in-tube heat exchanger: iii) a first expansion valve; and iv) a liquid to air heat exchanger. In varying embodiments, the cryogenic refrigerant circuit further comprises in fluid communication with the second compressor, the first tube-in-tube heat exchanger and the second tube-in-tube heat exchanger: iv) a second expansion valve. In varying embodiments, the chiller comprises a configuration as depicted in FIGS. 3A-3B. In some embodiments, the system comprises: a) a tank comprising a gas stored at saturated conditions and a liquid withdrawal means; b) a chiller in fluid communication with the tank, wherein the chiller subcools the gas to a temperature of −10° C. or lower; c) a pump downstream of and in fluid communication with the tank and the chiller, and a chamber configured for liquefied gas or supercritical gas extraction, wherein the pump comprises the gas at a temperature of −10° C. or lower; wherein the mass flow rate of the subcooled liquid phase gas through the pump is repeatable and proportionate to pump speed. In some embodiments, the gas is selected from the group consisting of carbon dioxide, n-butane, n-propane, isobutane, dimethyl ether, and mixtures thereof. In some embodiments, the pump is a positive displacement pump. In some embodiments, the positive displacement pump is an unmodified high performance liquid chromatography (HPLC) pump. In varying embodiments, the system further comprises a post-pump heater downstream of and in fluid communication with the pump, wherein the post-pump heater heats the liquefied gas or supercritical gas up to an operational temperature.

In varying embodiments, the supercritical fluid is $CO_2$. In varying embodiments, the flow of the supercritical solvent through the system is in the range of about 10 ml/min, e.g., at least about 15 ml/min, 20 ml/min, 25 ml/min, 30 ml/min, 35 ml/min, 40 ml/min, 45 ml/min, or 50 ml/min, to about 300 ml/min. In varying embodiments, the system further pumps a co-solvent. In some embodiments, the co-solvent comprises an alcohol of three or fewer carbon atoms (e.g., methanol, ethanol, propanol, isopropanol) or an acetate of three or fewer carbon atoms (e.g., methyl acetate, ethyl acetate, propyl acetate), or mixtures thereof. In varying embodiments, the system is as depicted in FIG. 1.

In a related aspect, provided are methods of separating molecules from a supercritical fluid. In varying embodiments, the methods comprise inputting a stream of gas phase supercritical fluid comprising molecules into the tangential inlet of a cyclonic separator as described above and herein, wherein the stream of supercritical fluid rotates around the inner surface of the cyclone body, wherein the molecules separate from the stream, slide down the inner surface and exit the cyclone body into the collection container; and wherein the gas phase supercritical fluid exits through the cap, and wherein any molecules still in the fluid stream do not escape through the sintered filter of the cap. In varying embodiments, the interior of the cyclonic separator is in fluid connection with atmospheric pressure.

Definitions

The phrase "conical cyclone of fluid" refers to a downward spiral path which substantially does not cross itself.

BRIEF DESCRIPTION OF SEVERAL VIEWS OF THE DRAWINGS

FIG. 3A illustrates a block diagram of the chiller's two circuit cascade refrigeration system. FIG. 3B illustrates the chiller and HPLC pumps package. The post pump heater is used to bring process fluids up to operational temperatures.

DETAILED DESCRIPTION

1. Introduction

Figure 1:
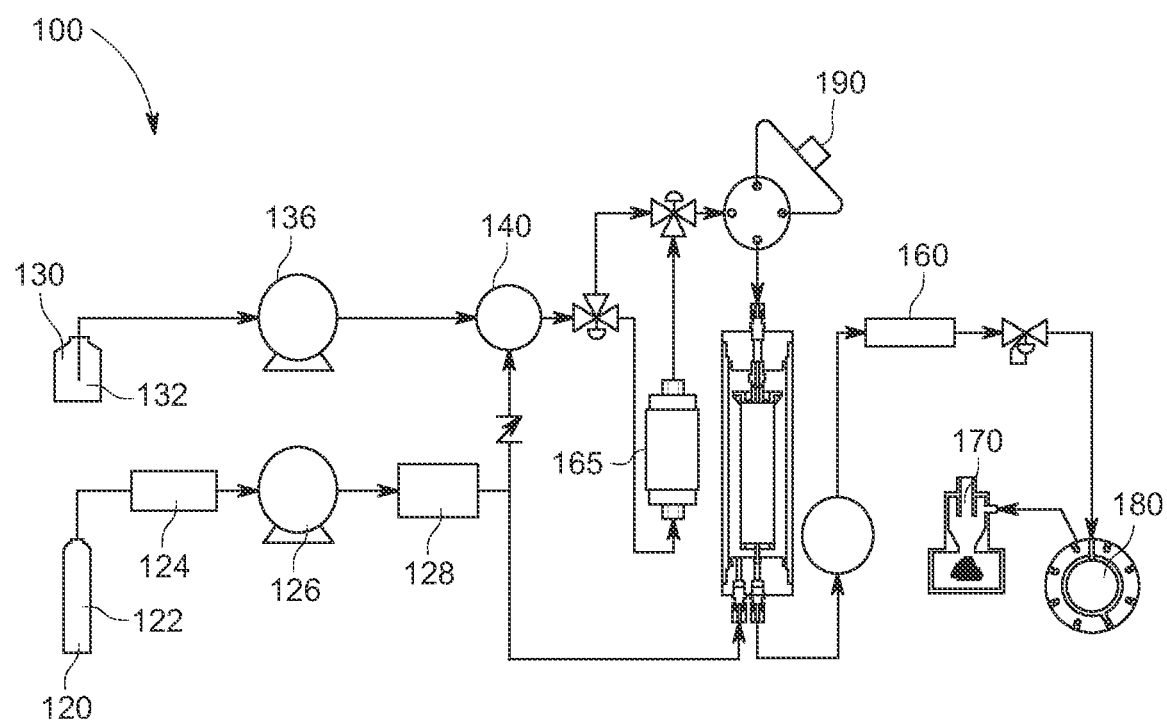
FIG. 1 illustrates a flow schematic of a chromatography system described herein.

Provided herein is gas/fluid low refrigerant circuit that may be used as a cooling loop for chilling a supercritical fluid within a supercritical fluid system is used for extracting and separating components of a chemical mixture. As described in more detail below, the cooling system may be comprised of an expansion device to expand a refrigerant fluid with a positive Joule-Thomson coefficient from an area of high pressure to one of lower pressure without capturing or recompressing the refrigerant fluid. Such expansion may be accomplished by passing the refrigerant fluid through an expansion device with one or more orifices or capillaries. The expansion device may be placed in close proximity to where the cooling effect is needed, for example, adjacent heat exchanger region of the supercritical fluid system in order to remove thermal energy from the supercritical fluid. The expanded refrigerant fluid may be passed through larger diameter channels to increase the residence time and surface area and allow the cold low pressure refrigerant fluid to absorb energy from the object being cooled, e.g., proximal supercritical fluid. The larger diameter channels can be machined directly into the adjacent system to be cooled for superior heat transfer. Further efficiencies can be obtained by using the low pressure refrigerant fluid as it is exhausted and has approached temperature equilibrium with the object being cooled (e.g., supercritical fluid) to cool the incoming high pressure refrigerant fluid before expansion (e.g., heat exchanger) to reduce its enthalpy. This can be accomplished with a counter flow or other heat exchanger. The amount of cooling and/or temperature of the device being cooled can be controlled using feedback from a temperature sensor placed on or adjacent to the device or system being cooled. A control valve connected to the sensor may be used to control the flow into the pressure reduction device. This cooling method and systems utilizing this method will have numerous advantages such as very compact, low noise, low equipment cost, low operating cost, and the ability to reach lower temperatures that many conventional refrigeration systems.

One such supercritical fluid system that may benefit significantly from this improved cooling method is a supercritical fluid chromatography system. Specifically, the system disclosed herein is one that enable the separation cartridges employed in traditional flash chromatography applications to be used in conjunction with a liquefied gas or supercritical fluid dominated solvent system. This facilitates or allows for a substantial reduction on the order 80-90% of the organic solvents or a complete elimination of organic solvents in the separation process. Achieving this goal involves implementation of one or more features to enable operating conditions in the range of pressures associated with subcritical fluids or subcritical fluids, e.g., in a pressure range of about 35 bar or higher pressure. These features include a prechiller system, a pressure equalizing vessel, and a pressurized cyclonic separator. When used in coordination, these improvements allow for liquefied gas and supercritical fluids to be utilized where only low pressure liquid solvents could previously been employed. The prechiller system enables a standard HPLC pump, nominally optimized for operation with incompressible fluids, to be employed with a liquefied gas or supercritical fluid. The pressure equalizing vessel enables an off-the-shelf chromatography cartridge, nominally intended for use with low pressure liquid solvents, to be used without further alteration in a liquefied gas or supercritical fluid system. The high pressure cyclonic separator enables product recovery from a high pressure system and serves the purpose of a collection flask in a high pressure system.

2. Supercritical Fluid Chromatography Systems

Figure 2:
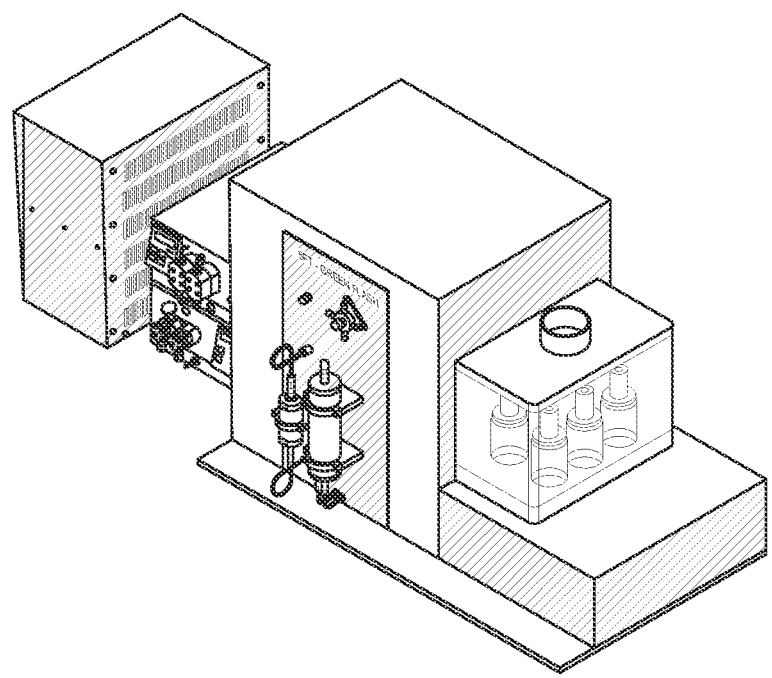
FIG. 2 illustrates an apparatus schematic of a chromatography system described herein.

The chromatography systems described herein are based, in part, on the discovery and advanced design of traditional flash chromatography technology that employs supercritical fluid (e.g., liquid phase $CO_2$) as the main non-polar solvent in flash chromatography. FIGS. 1 and 2 illustrate a supercritical fluid $CO_2$ flash chromatography apparatus. In varying embodiments, the apparatus has one or more of prechiller/supercritical fluid (e.g., $CO_2$) pump that allows for the efficient and accurate delivery of liquid-phase supercritical fluid (e.g., $CO_2$) in a supercritical fluid state to the apparatus up to 10,000 psi, e.g., up to 5000 psi or 2500 psi and at a flow rate of at least about 10 mls/min and up to about 250 mls/min or 300 mls/min, a secondary co-solvent pumping package that allows for polar modifier solvents (e.g., co-solvents) to be added to the flow stream in an isocratic or gradient mode (2500 psi and 100 mls/min), an injection manifold that can take the form of an injection loop or a secondary injection column for larger sample injection, a pressure equalizing vessel assembly that allows traditional flash column cartridges to be used in the apparatus up to the pressures of operation, a UV-VIS detector (other detectors optional), and a back pressure regulator (BPR) upstream of and in fluid communication with a stream selector, which is in fluid communication with the one or more cyclonic separators. The BPR brings the pressure of the flow stream from operation pressures down to ambient pressures for fraction collection in the cyclonic separators.

As shown in FIG. 1 a chromatography system 100 is pressurized to pump supercritical fluid 120 (e.g., $CO_2$), from a source 122 with or without co-solvent. In varying embodiments, the system further pumps a co-solvent 130 from a source. When pumping a supercritical fluid mixed with a co-solvent, the co-solvent may comprise up to about 20% v/v of the fluid being pumped through the system. As shown in FIG. 1, the co-solvent is delivered through an input pump 136 separate from the supercritical fluid input pump 126, and mixed with the supercritical fluid in a mixer 140 prior to delivery to the inner column of the pressure equalizing vessel. In some embodiments, the co-solvent comprises an alcohol of three or fewer carbon atoms (e.g., methanol, ethanol, propanol, isopropanol) or an acetate of three or fewer carbon atoms (e.g., methyl acetate, ethyl acetate, propyl acetate), or mixtures thereof. The chromatography system shown in FIG. 1 also comprises a chiller 124 and a pre-heater 128 for the supercritical fluid 120. A post heater 160, a cyclone collector 170 and a stream selector that is capable of selecting 1 or 8 cyclone collectors for the sample.

3. Chiller for Pumping Supercritical and Liquefied Gases

A system for super chilling liquid gases (e.g., including carbon dioxide, methane, ethane, propane, butane, ethylene, propylene, and ethers) and to increase pumping efficiency and consistency is provided. The chiller 124 cools liquid gases (e.g., including carbon dioxide, methane, ethane, propane, butane, ethylene, propylene, and ethers) to between $-10°$ C. and $-40°$ C. and has been shown to enable the use of a standard HPLC pump with increased mass flow rates at a constant set point as the temperature is reduced. The herein described system reduces the cost of pumping $CO_2$ by allowing the use of traditional HPLC pumps, rather than highly specialized $CO_2$ pumps.

The present systems and methods use a cascade chiller to cool the liquid $CO_2$ to less than $-10°$ C. e.g., in varying embodiments, less than $-20°$ C., to minimize the variance in pump performance. The lower temperatures enable greater tolerance for the flow path in the high pressure $CO_2$ pump head and facilitate the use of an unmodified HPLC (High Pressure Liquid Chromatography Pump). Traditional HPLC pumps are normally intended for pumping liquids; not liquid gases. There is a wide scatter in flow performance that results when the liquid is chilled to only $0°$ C. At room temperature conditions the variance would be greater than 30% and would render the unmodified HPLC pump completely ineffective in supercritical chromatography applications. The herein described chiller and methods allows the use of a traditional HPLC for precise metered pumping of liquid-gases, e.g., for delivery to extractors, reactors and chromatography equipment.

We have determined that extreme subcooling much improved pumping performance. The pumping mass flow rate was linearly related to speed and repeatability. In this case, the supercritical $CO_2$ was subcooled from an ambient condition of nearly $25°$ C. and 52 bar to approximately $-25°$ C. and 52 bar. This $55°$ C. temperature reduction resulted in the liquid $CO_2$ conditions more closely resembling an incompressible fluid, such as water. A completely unmodified and standard HPLC pump can then be used to pump the $scCO_2$ under very linear conditions. Such behavior is highly desirable for applications including supercritical fluid extraction, supercritical fluid solid phase extraction, supercritical fluid flash chromatography, and supercritical fluid chromatography.

The use of this hook of physics is advantageous in these applications, as it enables standard and cost-effective HPLC pumps to be used in supercritical fluid applications with highly linearly mass flow rates without the need for either elaborate compensation algorithms, sensor feedback systems involving compensation via a loss in weight measurement of the supply cylinder, direct compensation via a mass flow measure (e.g. coriolis mass meter), or the need for a booster pump to stabilize the delivery flow to the pumping system.

a. Prechiller or Chiller-HPLC Pump Assembly

Figure 3A:
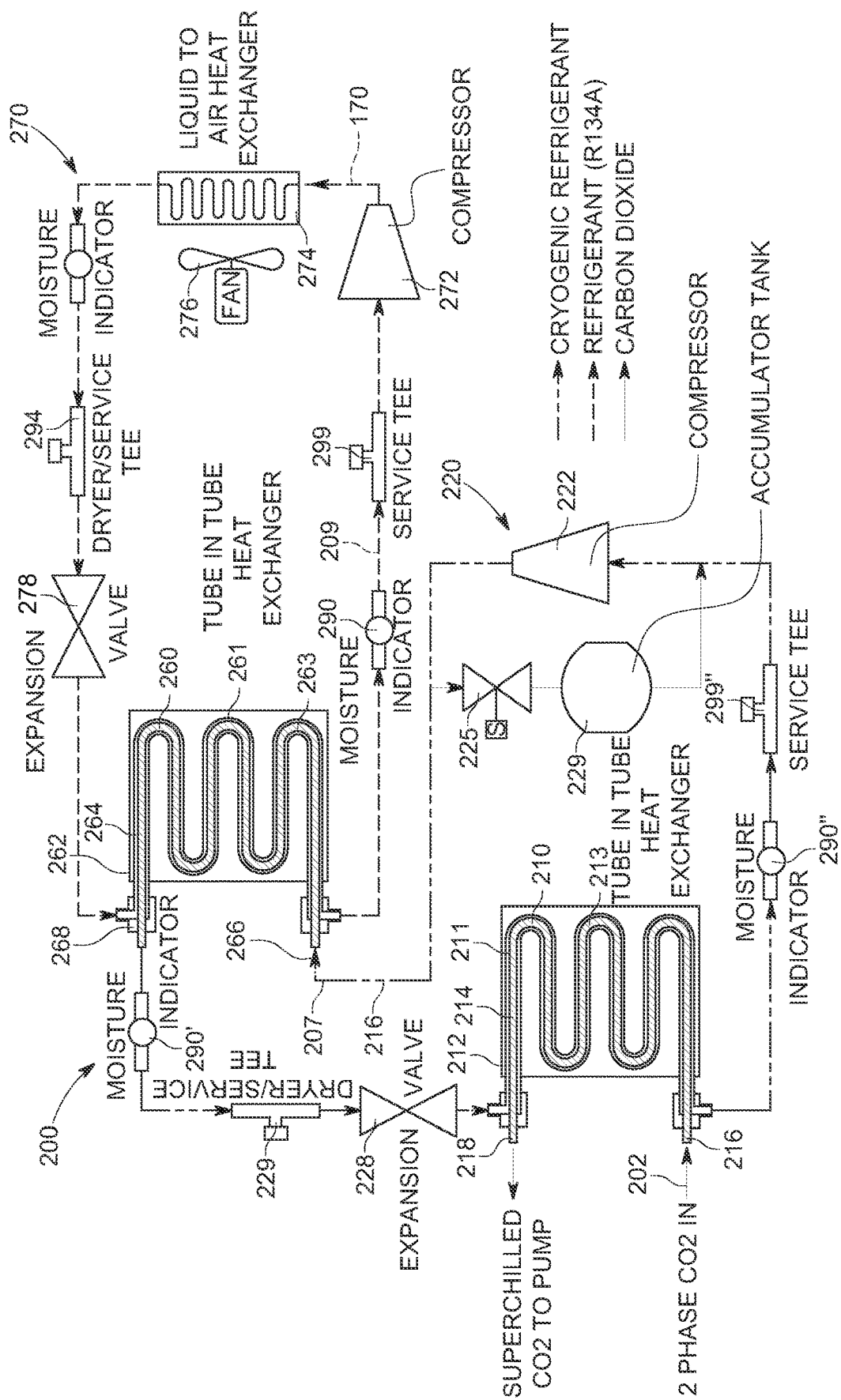
FIGS. 3A-B.

Generally, the prechiller or chiller 200 utilizes dual refrigeration circuits with tube-in-tube heat exchangers that allow for heat exchange without an intervening heat exchange medium. FIG. 3A illustrates a block diagram of the two circuit cascade refrigeration heat exchanger present in the chiller. The two circuits are a low temperature refrigeration circuit 220 and a high temperature refrigeration circuit 270. In such systems, the two circuits are thermally coupled at the condenser 213 of the low temperature circuit. In fact, the condenser of the low temperature circuit is the evaporator 211 of the high temperature circuit. To further simplify the concept, the low temperature refrigeration circuit 220 in the chiller is used to super chill the $CO_2$ 202 flow to its target temperature and the high temperature refrigeration 270 circuit is used to remove the heat from the low temperature circuit.

$CO_2$ flow enters the evaporator of the low temperature circuit at bottle pressure/temperature. Said evaporator is a tube-in-tube heat exchanger 210 with an inner tube 214 made of AISI Type 316 stainless steel or similar metal suitable for exposure to $CO_2$. Other materials of use for the inner tube include without limitation copper, brass, and Type 304 stainless steel. Heat is removed from the $CO_2$ by the flow of cryogenic refrigerant in the outside tube 212 which is made of copper and surrounds the inside tube. The heat exchanger is set up as a counter flow heat exchanger for greater efficiency.

The low temperature circuit is used to pull heat from the $CO_2$ flow to chill it to the required temperature. A cryogenic refrigerant enters the suction side of the compressor 222 and is discharged at a higher pressure. The compressor may be a 1.4 CC model by Aspen. Work is done by the compressor to increase the pressure of the cryogenic refrigerant 207, which raises its temperature. The cryogenic refrigerant then exits the compressor on the discharge (high pressure) side and enters the low temperature circuit condenser. The low temperature circuit condenser is the same unit as the high temperature circuit evaporator. The condenser is a tube in tube heat exchanger. The cryogenic refrigerant flows through the inside tube 264 of the heat exchanger from an inlet 266 to an outlet 268. Heat is removed from the cryogenic refrigerant by a conventional refrigerant 209 flowing in the outside tube 262 which surrounds the inside tube. This heat exchanger is arranged as a counter flow heat exchanger for greater efficiency. After having the heat removed, the cryogenic refrigerant flows through a moisture indicator 290', and then a dryer 229 which has a built in service port. This is the high pressure side service port. After the dryer, the cryogenic refrigerant flows through an expansion valve 228. In this case, the expansion valve is a coiled length of capillary tube. When the cryogenic refrigerant exits the expansion valve, it is returned back to a low pressure state, which reduces the temperature before it enters the low temperature circuit evaporator 211. The cryogenic refrigerant 207 flows through the outside tube of the evaporator and removes heat from the $CO_2$ 202 flowing through the inside tube which it surrounds. Upon exit, the cryogenic refrigerant flows through a moisture indicator 290" and a service tee 299" before returning to the suction side of the low temperature circuit compressor 222. This cycle is continuous. The low temperature circuit may also comprise an accumulator tank 229 and valve 225 for accumulation of cryogenic refrigerant 207.

The high temperature circuit uses a similar flow path with one major difference. The condenser of the high temperature circuit is a fan cooled liquid to air heat exchanger. In the high temperature circuit, a conventional refrigerant 209 enters the suction side of the compressor 272 and is discharged at a higher pressure. The change in pressure is accompanied by a rise in temperature. The refrigerant then flows into the condenser 274 where forced air is used to remove heat by an air moving device 276, such as a fan. This heat is transferred to the atmosphere and out of the system. The refrigerant then flows through a moisture indicator and a dryer 294 with built in service port before going through the expansion valve. On exit of the expansion valve 278 the refrigerant is returned to a lower pressure and thus lower temperature. The refrigerant then enters the evaporator 261. Here the refrigerant for the high temperature circuit absorbs heat from the low temperature circuit in a tube-in-tube heat exchanger 260. The tube-in-tube heat exchanger 260 acts as a condenser 263 for the cryogenic refrigerant 207. Upon exit the refrigerant goes through a service tee and a moisture indicator before returning to the suction side of the compressor. This cycle is continuous.

To summarize the two circuit cascade system, it is easiest to follow the transfer of heat into and then out of the system. In the case of the chiller 200, heat is brought into the system by a stream of $CO_2$. The removal of heat from the $CO_2$ is the ultimate goal of the system. This heat is removed by the evaporator of the low temperature circuit. The low temperature circuit is then used to transfer heat to the high temperature circuit. This happens in the high temperature circuit evaporator which is also the low temperature circuit condenser. In the final stage of heat transfer, the high temperature circuit transfers heat out of the system and into the atmosphere in the high temperature circuit condenser. In short, heat cascades from the $CO_2$ to the low temperature circuit then the high temperature circuit and finally the atmosphere.

Figure 3B:
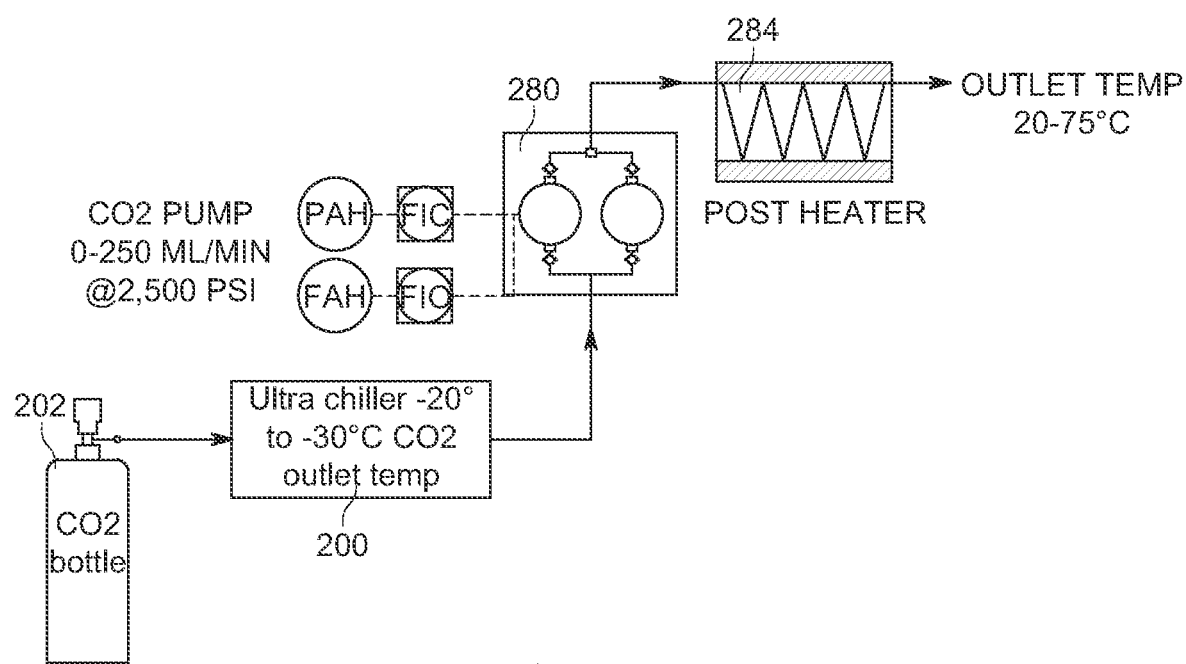

FIG. 3B illustrates the connection of the chiller 200 to a traditional HPLC type SCF Pump 280 with the addition of post-pump heater 284 to bring the fluids up to operational temperatures.

b. Embodiments of Prechiller or Chiller

In varying embodiments, the chromatography system comprises a prechiller or chiller, as described herein, upstream of a pump to cool the supercritical fluid sufficiently such that it can be pumped through a standard off-the-shelf, commercially available flash chromatography or high performance liquid chromatography (HPLC) pump. The prechiller improves the pumping performance (e.g., the consistency) for a supercritical fluid, e.g., carbon dioxide such that system mass flow rates are proportionate to pump speed.

In varying embodiments, the prechiller cools the liquid phase supercritical fluid (e.g., $CO_2$) to a temperature of about $-5°$ C. or less, e.g., $-10°$ C., $-15°$ C., $-20°$ C., $-25°$ C., or less, e.g., but above the triple point temperature, e.g., above about $-55°$ C., e.g. to about $-40°$ C., $-45°$ C. or $-50°$ C. Such supercooling or extreme subcooling reduced in much improved pumping performance. The pumping mass flow rate was linearly related to speed and repeatability. In varying embodiments, the prechiller subcools the supercritical fluid (e.g., $CO_2$) from an ambient condition of nearly $25°$ C. to approximately $-10°$ C. or lower temperatures. In varying embodiments, the system employs a 2-stage refrigerant on refrigerant chiller system to cool and liquefy the gas phase supercritical fluid. In varying embodiments, the system does not directly or separately cool the pump heads.

This minimum of $35°$ C. temperature reduction resulted in the supercritical fluid (e.g., liquid phase $CO_2$) conditions more closely resembling an incompressible fluid, such as water. A completely unmodified and standard HPLC pump can then be used to pump the supercritical fluid (e.g., liquid phase $CO_2$) under very linear conditions. Such behavior is highly desirable for application including supercritical fluid extraction, supercritical fluid solid phase extraction, supercritical fluid flash chromatography, and supercritical fluid chromatography.

The supercooling prechiller enables standard and cost effective HPLC pumps to be used in supercritical fluid applications with highly linearly mass flow rates with the need for either elaborate compensation algorithms, sensor feedback systems involving compensation via a loss in weight measurement of the supply cylinder, direct compensation via a mass flow measure (e.g., coriolis mass meter), or the need for a booster pump to stabilize the flow.

4. Pressure Equalizing Vessel a. Introduction

Pressure equalization assemblies and methods of use are provided. More specifically, provided is a pressure equalization assembly that enables the use of low-medium pressure columns for flash chromatography in a higher pressure supercritical fluid chromatography application. The pressure equalization assemblies allow the attachment of commercially available chromatography columns or cartridges to the cap of the vessel, e.g., via a luer lock fitting, and seals on the other end using an O-ring or gasket that is captured axially by the cap and tapered stem of said column. Sample stream pressure going through the column is balanced by external pressure applied to the same column to maintain a pressure differential that is less than the standard operating pressure of the column. In doing so, it ensures that the columns can be used without failure for high pressure supercritical fluid chromatography.

b. Embodiments of the Pressure Equalizing Vessel

In varying embodiments, the supercritical fluid chromatography system comprises a pressure equalizing vessel. The pressure equalizing vessel is designed to allow the use of commercially available or off-the-shelf low to medium pressure columns (e.g., in the range of about 14-200 psi) traditionally used in flash chromatography at the higher pressures (in the range of about 1000 psi to about 10,000 psi, e.g., in the range of about 1500-2000 psi) used in Supercritical Flash Chromatography. The pressure equalizing vessels described herein allow the use of more economical pre-packed disposable columns in Supercritical Flash Chromatography, rather than expensive high pressure columns that must be re-packed by the user.

The pressure equalization vessel described herein utilize pressure equalization to allow the low pressure columns to exceed their rated burst pressures. This is accomplished by pressurizing the outside of the column to a level that ensures that the pressure differential between the flow through the inside of the column and the equalizing pressure on the outside of the column remains within the rated pressure of the column. For example, if a column is rated at 200 psi normal operating pressure, and the user desired to run at higher pressure ranges of about 1000 psi to about 10,000 psi, e.g., 1500-2000 psi, the system would ensure that the equalizing pressure is within 200 psi of working pressure. Testing has proven this to be effective at preventing failure of the columns due to overpressure.

The pressure equalization system allows the attachment of commercially available or off-the-shelf flash chromatography columns to the cap of the vessel via a luer lock fitting, and seals on the other end using an O-ring or gasket that is captured axially by the cap and tapered stem of said column. The pressure equalizing vessel is compatible for use with any commercially available pre-packed flash chromatography cartridge, including without limitation cartridges made by Grace (grace.com), Silicycle (silicycle.com), Biotage (biotage.com), Teledyne-ISCO (isco.com), Buchi (buchi.com), Interchim Inc. (interchiminc.com), and Agilent (agilent.com). The pressure equalizing vessel does not limit the size of the inner column cartridge that can be used, but is designed to adjust and accommodate to the chromatography cartridge appropriate for a desired separation. In varying embodiments, the inner column can contain in the range of from about 4 grams to about 350 grams stationary phase media, e.g., 4 grams, 8 grams, 12 grams, 20 grams, 80 grams, 120 grams or 330 grams stationary phase media. In varying embodiments, the inner column comprises a diameter in the range of about 0.5 inches to about 3.5 inches and a column length in the range from about 3.5 inches to about 11 inches. Illustrative diameter and length sizes of the inner column include without limitation 0.94 inches diameter.times.3.85 inches length (4 grams stationary media); 1.38 inches diameter.times.4.60 inches length (12 grams stationary media); 1.77 inches diameter.times.6.43 inches length (40 grams stationary media); 1.99 inches diameter.times.9.50 inches length (80 grams stationary media); 2.18 inches diameter.times.10.31 inches length (120 grams stationary media); or 3.39 inches diameter.times.10.55 inches length (330 grams stationary media).

Sample stream pressure going through the column is balanced by external pressure applied to the same column to maintain a pressure differential that is less than the standard operating pressure of the column. In doing so, it ensures that the columns can be used without failure for high pressure supercritical fluid chromatography.

Figure 8:
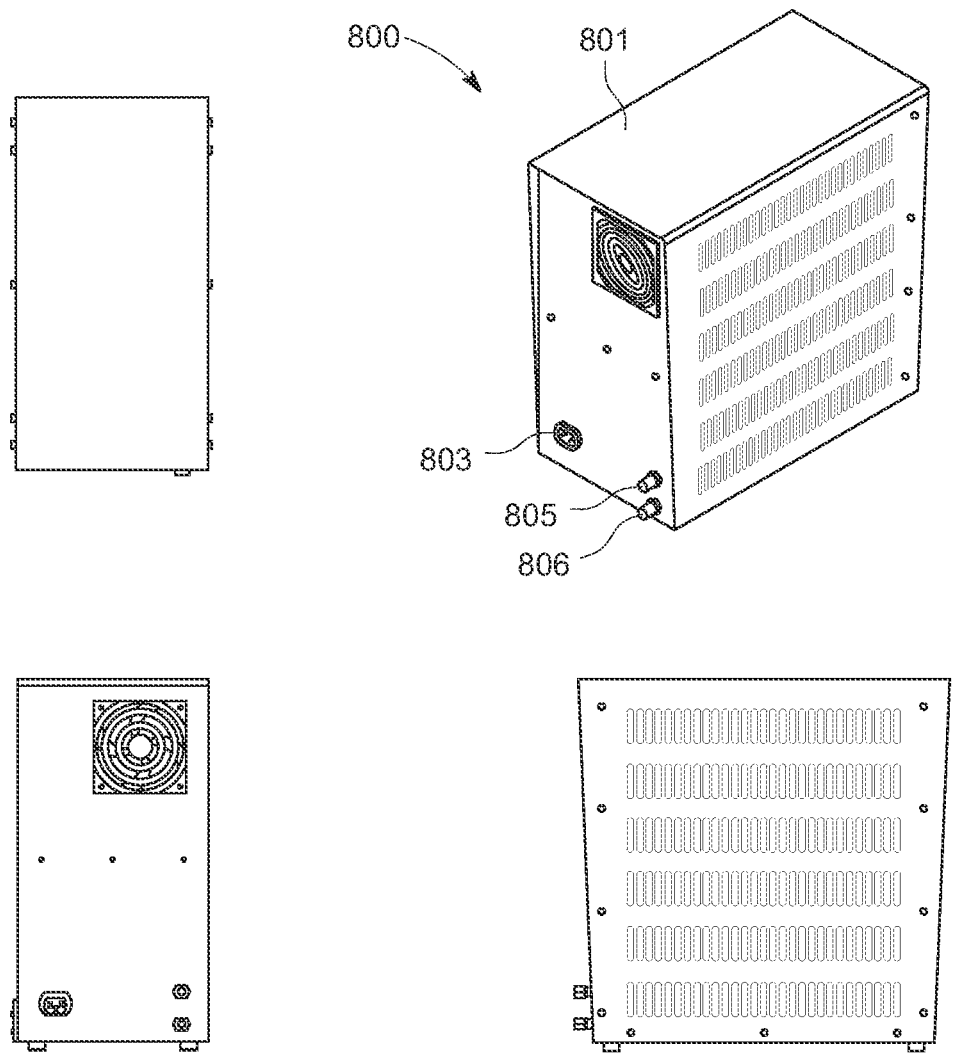
FIG. 8 illustrates an assembly drawing of external views of a production prototype of the chiller.

FIG. 8 illustrates an assembly drawing of external views of a production prototype of the chiller 800 configured within an enclosure 801 having a power connection 803 and having bulkhead connections 805 and 806.

Figure 9:
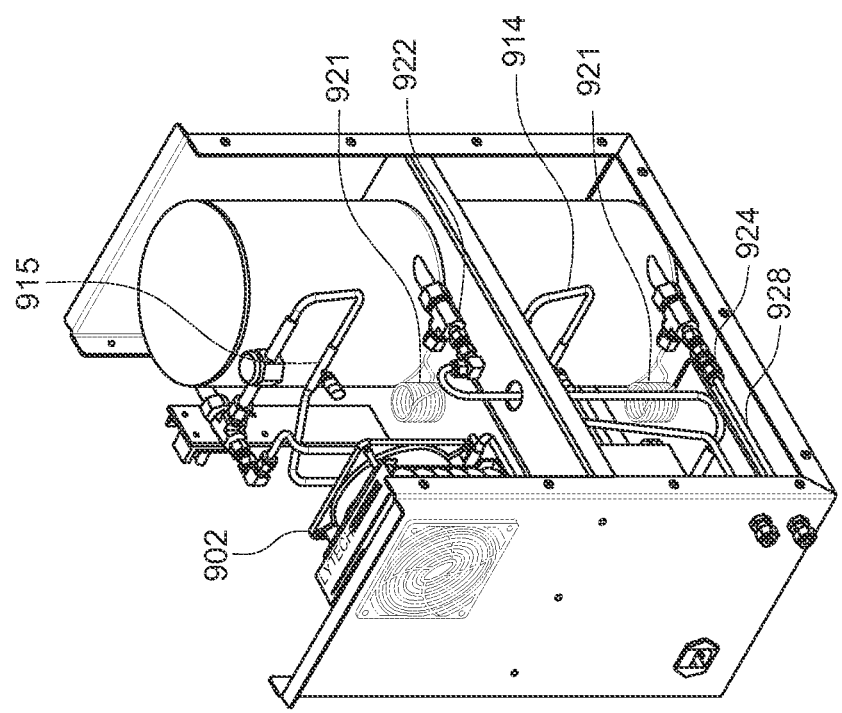
FIG. 9 illustrates an assembly drawing of internal views of a production prototype of the chiller.
Figure 9:
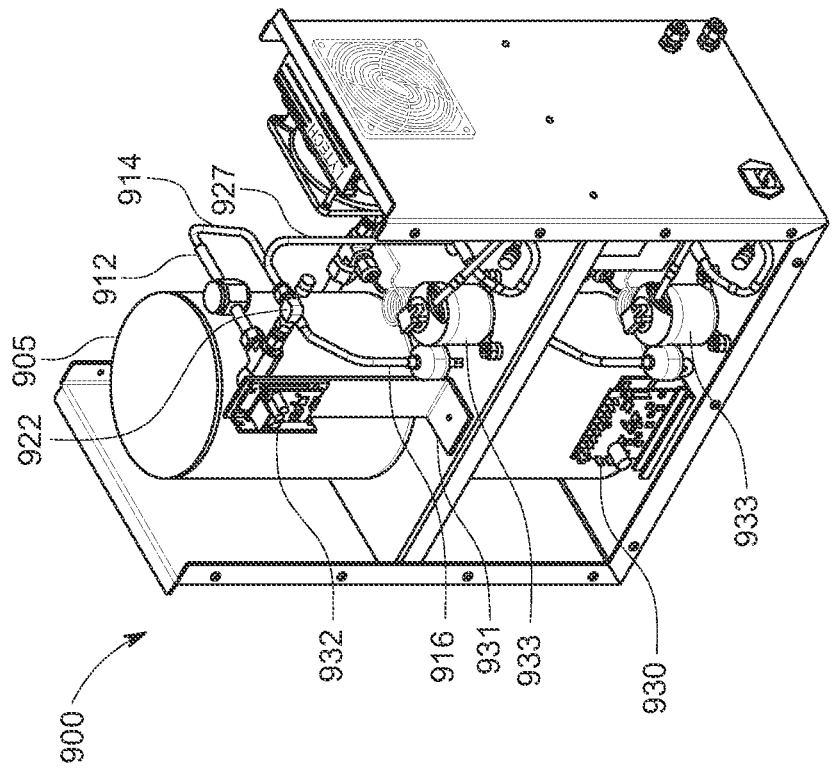

FIG. 9 illustrates an assembly drawing of internal views of a production prototype of the chiller 900. Fan-cooled heat exchanger 902. Tube-in-tube heat exchanger 905. Sight glass; moisture indicator 912. Sight glass to service Tee Tube 914. Access valve 915. Service Tee to suction inlet tube 916. Capillary tube winding 921. Union elbow with tube fitting 922. Union coupling with tube fitting 924. Cryo compressor suction inlet tube 927. Liquid gas outlet tube 928. High capacity compressor drive 930. Mounting bracket 931. Drive board-compressor 932. 1.4 CC compressor 933.

Figure 10:
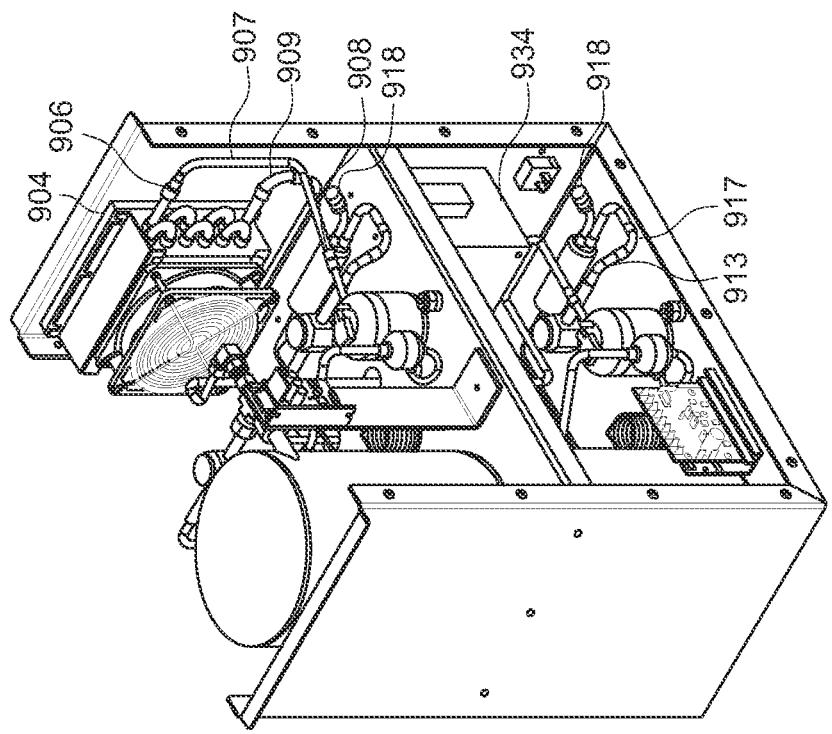
FIG. 10 illustrates an assembly drawing of internal views of a production prototype of the chiller.
Figure 10:
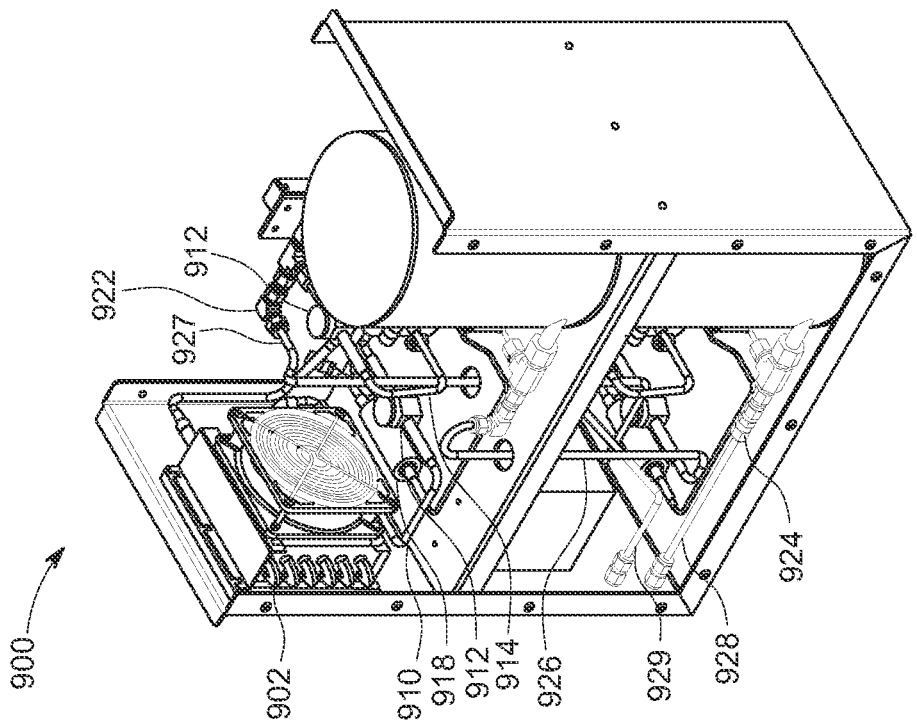

FIG. 10 illustrates an assembly drawing of internal views of a production prototype of the chiller 900. Fan mounting bracket 904. Reducing coupling 906. Compressor to condensing tube 907. Solder connection; copper fitting 908. 90 degree long elbow solder connection 909. Condenser to sight port tube 910. Copper tube, 45 degree elbow 913. 90 degree long elbow solder connection 917. Dryer, liquid line with service port 918. Down tube—condenser side 926. Liquid gas inlet tube 929. Power supply 934.

Figure 11:
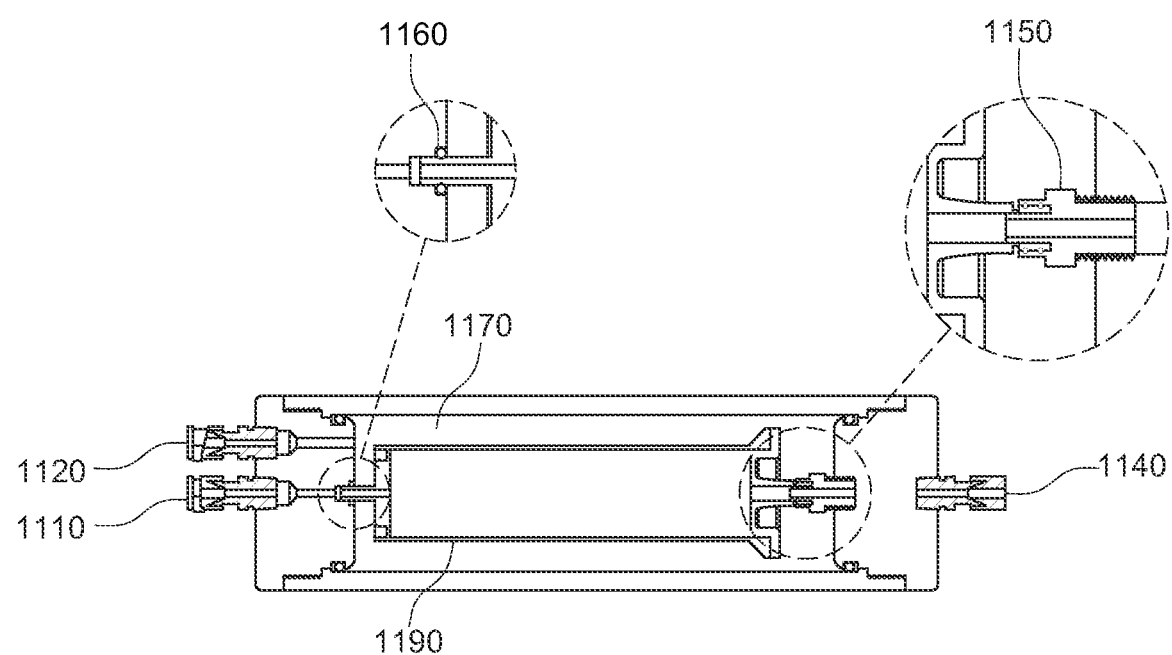
FIG. 11 illustrates a cross sectional view of the pressure equalizing vessel showing the outer pressure containment vessel and the inner chromatography cartridge or column. Insets depict the input and output attachments of the inner chromatography cartridge or column to the outer pressure containment vessel.

FIG. 11 illustrates a cross sectional view of the column system. It shows the pressure containment vessel 1170, the medium pressure column 1190, and the methods for attaching the column to the vessel itself. The fittings of the pressure equalizing vessel can be readily adjusted to accommodate the inner column being used, wherein the standard input fitting accommodates a female luer lock on the inner column and the standard output fitting accommodates a male slip fitting on the inner column. In the embodiment depicted in FIG. 11, a luer lock connection provided on the supercritical fluid (e.g., $CO_2$) plus optional co-solvent inlet 1140 of the column seals the outside pressure from the sample stream pressure. The luer lock adapter 1150 is shown as a threaded adapter in this print, but may also be an integral machined part of the vessel cap, or also a welded adapter. On the other end of the column, the outside equalizing pressure, and the sample stream pressure are sealed from each other using an O-ring 1160 or gasket, on the outside of the column stem. The cap of the vessel has a shelf to capture said gasket and the column stem is tapered so that it also helps capture the gasket in position by providing an axial force. This tapered stem and the luer lock on the opposite end are typical of industry standard low-medium pressure columns.

FIG. 11 also shows the inlet connection for the sample stream 1140. This stream typically is composed of a supercritical fluid (e.g., $CO_2$), optionally a co-solvent, and the sample to be separated. The fitting shown is a high pressure compression fitting made to seal on the outside diameter of appropriately sized high pressure tubing. The same type of fitting is used for the Sample stream outlet 1110, and the pressure equalizing inlet 1120. The pressure equalizing medium will typically be a supercritical fluid (e.g., $CO_2$).

Figure 12:
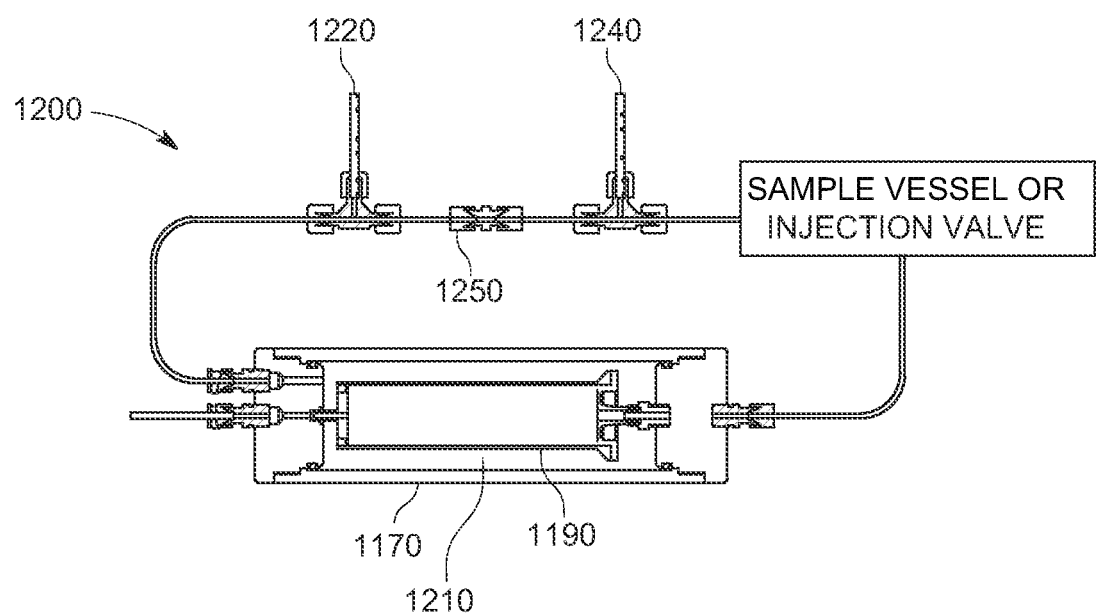
FIG. 12 illustrates a cross sectional view of the pressure containment vessel in the context of its fluid connections with an exemplary chromatography system.

FIG. 12 illustrates a cross sectional view of an example supercritical flash chromatography system 1200 with the pressure equalization system incorporated. FIG. 12 illustrates the typical input of supercritical fluid (e.g., $CO_2$) 1220 and input for co-solvent 1240, and shows how the system equalizes pressure in this case. Input flow of supercritical fluid (e.g., $CO_2$) is split, one direction serves as the pressure equalizing fluid, and the other direction is used in conjunction with co-solvent to flow with the sample through the column. The system pressure is controlled by a back pressure regulator.

The check valve 1250 after the input tee for supercritical fluid (e.g., $CO_2$) ensures that the pressure is typically greater on the outside of the low pressure column. This means that if any leaks were to occur, the leaks would occur from outside equalizing fluid, into the column. This protects the valuable samples being separated from being lost.

5. Cyclonic Separator a. Introduction

In varying embodiments, the supercritical fluid chromatography system comprises a cyclonic separator. The cyclonic separator is designed to efficiently and effectively separate sample molecules from a liquid phase or gas phase stream of a supercritical fluid, e.g., $CO_2$. The separator is designed to accept tangential input flow, e.g., via tube compression fitting, allowing the separator to accept typical industry standard tubing. Using a tangential inlet, the flow is channeled in a cyclonic flow around the separator to separate the molecules from the gaseous flow by centrifugal force. The separator deposits the sample molecules conveniently into an attached sample collection jar, and can be completely disassembled for complete cleaning. To ensure any molecules not successfully separated by the centrifugal forces of the cyclone are not released to atmosphere, a sintered filter of an appropriate size (e.g. having a porosity grade of G-5, or a pore size in the range of about 1-16 microns) can be pressed into the exit of the cyclone, allowing only the gaseous flow to escape.

b. Embodiments of the Cyclonic Separator

The herein described cyclonic separators are designed to separate molecules from a gas phase supercritical fluid (e.g., $CO_2$) flow and collect the molecules in a sample jar. In varying embodiments, separation procedures are performed at flow rates in the range of about 10-300 ml/min, e.g., about 250 ml/min, and at pressures in the range of about 1000-10,000 psi, e.g., about 1500-2000 psi or about 1,750 psi. The cyclonic separators can be used within a pressurized chromatography system and in fluid communication with a sample stream using compression fitting adapters and can be vented to atmosphere directly, or by hooking up a hose to the outlet. All materials of construction are suitable for use with corrosive solvents.

Other forms of cyclonic separators have been used in the past to attempt to separate a desired sample from $CO_2$/co-solvent streams in the supercritical fluid extraction products. These have been much cruder, simpler devices typically consisting of an inlet tube that would bring the fluid/particle stream into a collection vessel at 90 degrees, the product stream would circulate around the interior diameter of the collection vessel and the particulate products and modifier co-solvents would drop out and settle at the bottom of the collection assembly and the gaseous SCF $CO_2$ would vent through and an outlet tube. The problem with these devices was always the loss of desired product to the fluid gaseous stream on the outlet. This was because none of the devices were designed to form a true cyclonic flow, nor were they equipped with proper filtration on the outlets. By contrast, with the presently described cyclonic separators, a cyclonic flow path is induced in which the gas is forced into rotational flow around the exit tube facilitated by the tangential inlet, and is then forced into a downward spiral in towards the low pressure region by the conical section. The low pressure region is in the middle of the volume where the exit is located.

Figure 13:
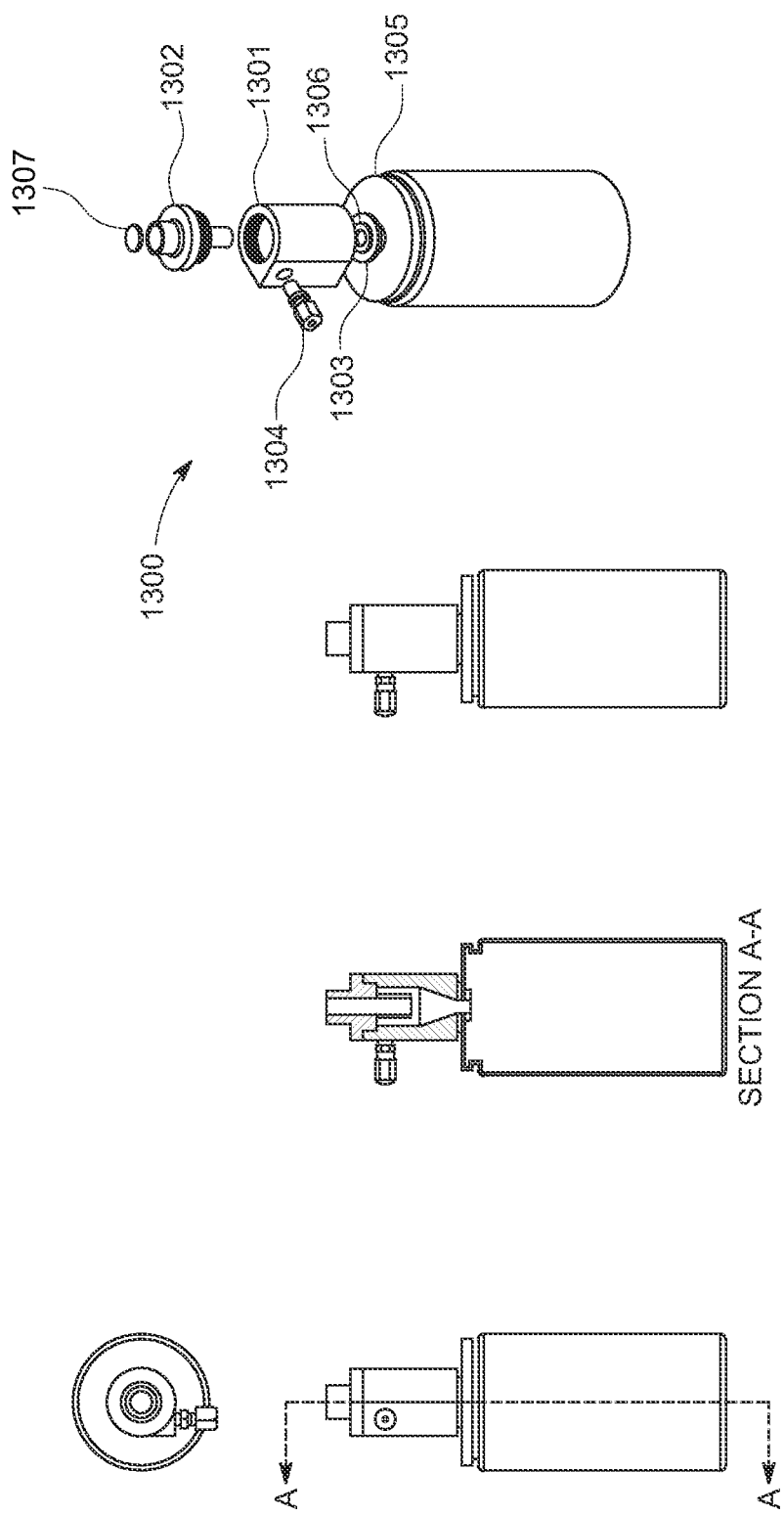
FIG. 13 illustrates an assembly drawing of the system, including a breakdown of the parts and quantities required.

FIG. 13 illustrates an overall assembly drawing of the cyclonic separator and collection assembly 1300. The cyclone body 1301 is connected to the fluid stream using a National Pipe Thread (NPT)×compression adapter. In this illustrated assembly, the compression fitting is sized for ⅛" tube and the NPT fitting is ¹⁄₁₆". Compression fittings 1304 may be sized in the range of about ¹⁄₁₆ inches to about ¼ inches find use. The cyclone cap threads into the top of the cyclone body and seals against an O-ring. This ensures that pressure is not lost through the threads. The cap 1302 has a sintered filter 1307 pressed into the exit to ensure that any sample molecules that may not have been separated by the vortex flow are captured and not released to atmosphere. Pore sizes of the sintered disc can be sized for particular compounds. In the illustrated iteration, sintered filter having a porosity grade G-5 is used (1-16 microns pore size). In varying embodiments, sintered filters with G-0 to G-5 porosity grade find use (G5=pore size in the range of about 1-16 microns; G4=pore size in the range of about 10-16; G3=pore size in the range of about 16-40 microns; G2=pore size in the range of about 40-100 microns; G1=100-160 microns; and G0=pore size in the range of about 160-250 microns).

The cyclone body can be configured to be adapted to many standard collection jars 1305. In the embodiment illustrated in FIG. 13, a 500 mL glass collection jar is used. The cyclone body can have a threaded bottom exit for attachment and sealing to the collection jar. The cap of the jar can have a through hole, which allows the cyclone body to be secured to the cap using a nut. This connection can be sealed using an O-ring 1303, as illustrated. Electrical panel nut is 1306 and compression fitting is 1304.

Figure 14:
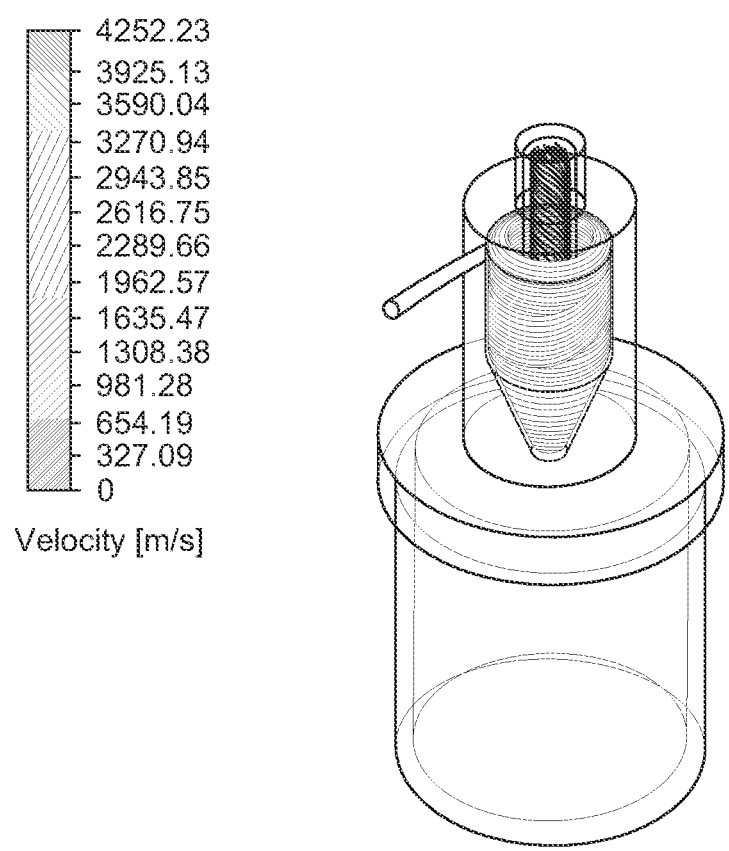
FIG. 14 illustrates a CFD visualization of the streamlines of the gas flow.

FIG. 14 illustrates the result of a Computational Fluid Dynamics (CFD) streamline study done to optimize the geometry of the cyclone at 250 mL/min@1,750 psi of supercritical $CO_2$ flow. When the $CO_2$ flow reaches the cyclone, it is no longer at such high pressures because the cyclone is open to atmospheric pressure. Because of this, the mass flow rate was calculated and then used to determine the velocity of the stream entering the cyclone. The shapes utilized have been done so to properly function with the parameters of the particular CFD program. Though the appearance may differ slightly from the assembly in FIG. 13, the internal geometry of the cyclone body is the same. The stream lines pictured illustrate the path and velocity of the fluid flow. The colors vary from red to blue, with red indicating the highest stream velocity, and blue indicating the lowest stream velocity. Most importantly, FIG. 14 illustrates the downward spiral, substantially non-overlapping stream lines typical of an optimized cyclonic separator.

As illustrated in FIG. 14, flow enters the cyclone body tangential to the inside diameter. The flow then begins to rotate around the exit tube of the cyclone. The centrifugal forces exerted on the molecules in the stream lines send the molecules outwards to the wall of the cyclone body, where a boundary layer keeps the streamlines from recollecting the molecules. The molecules are then free to fall to the bottom of the collection assembly. As the stream lines travel to the bottom of the cyclone body and hit the conical section, the velocity slows and the pressure increases. This forces the streamlines up the exit tube which is a low pressure escape from the higher pressure conical section.

Figure 15:
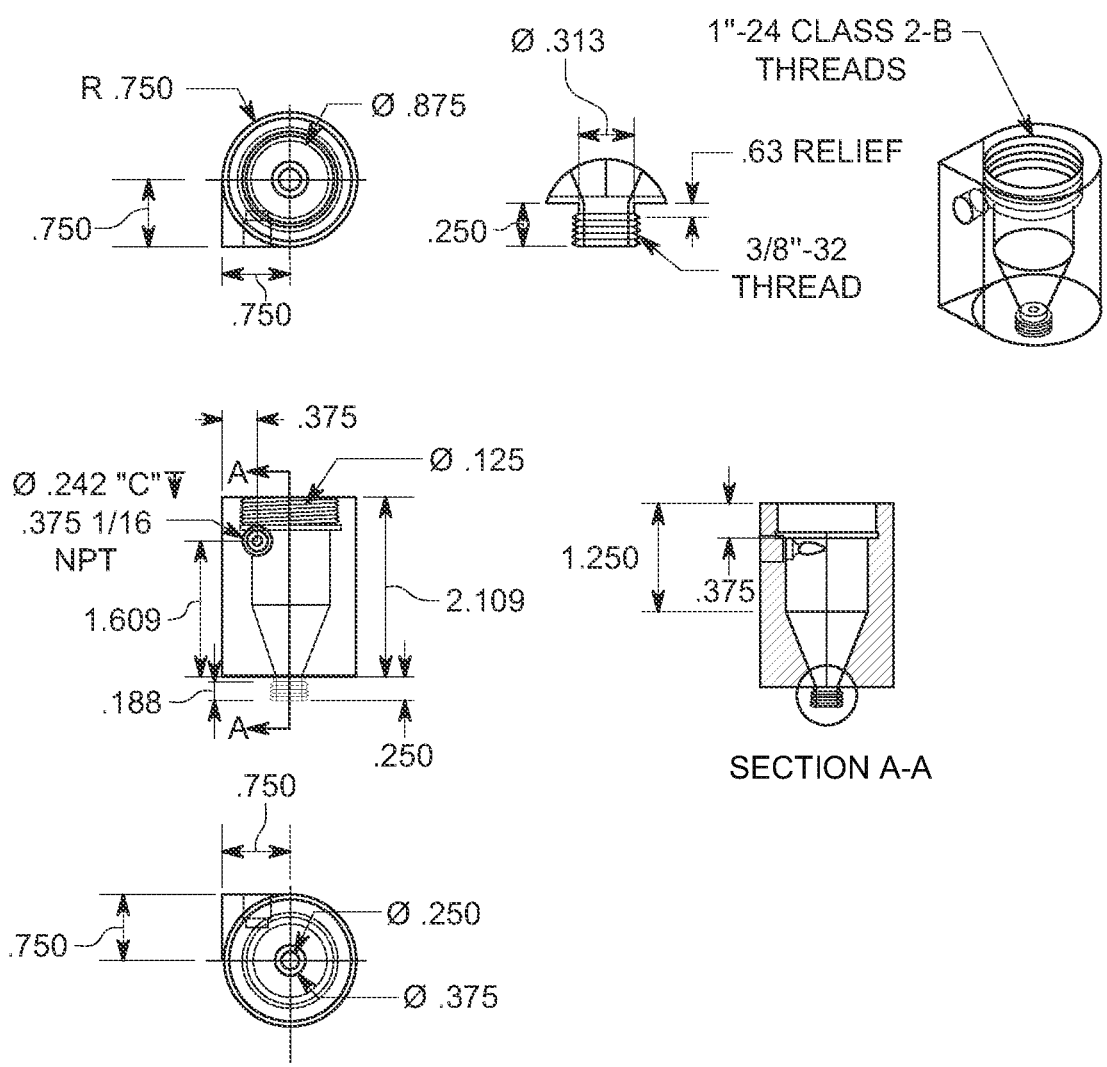
FIG. 15 illustrates a manufacturing print of the Collection Cyclone Body.

FIG. 15 illustrates the manufacturing print released to the machine shop for the current revision of the cyclone body. All dimensions and information pertinent to the manufacturing of the part are present. In the illustrated embodiment, the threads used to secure the cap to the body are the 1"-24 Class 2-B threads. Thread size is determined by the body of the cyclone, wherein the thread size and conformation are selected to withstand pressure and secure the cap. Generally, the threads are larger than the inside diameter of the cyclone body. In the illustrated embodiment, the body is secured to the collection vessel using a ⅜"-32 National Extra Fine (NEF) thread. The function of the cyclone is not dependent on these threads, they were selected to aid in manufacturing and assembly.

Figure 16:
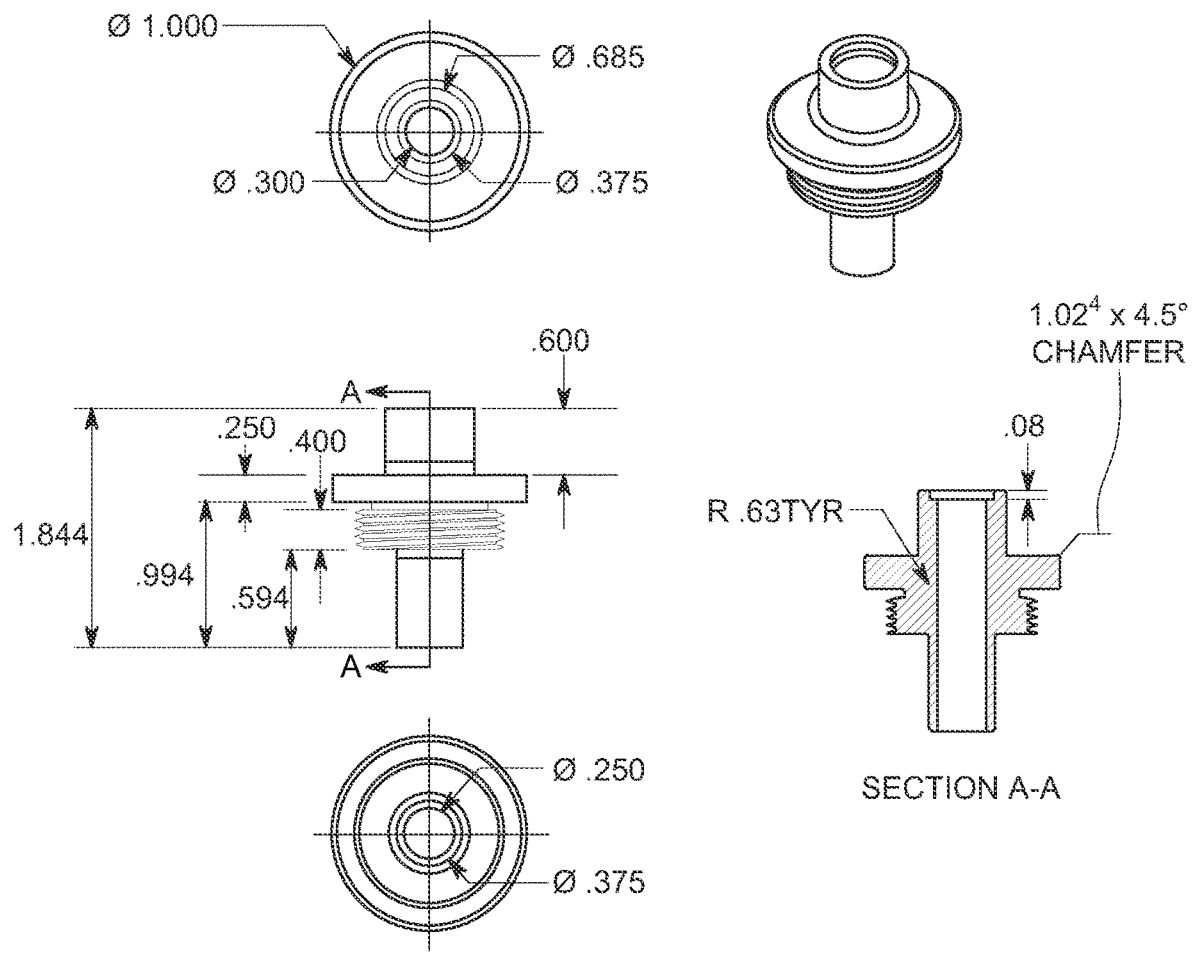
FIG. 16 illustrates a manufacturing print for the Collection Cyclone Cap.

FIG. 16 illustrates configurations of the cyclone cap. In the illustrated embodiment, the cyclone cap is secured to the cyclone body via screw threads. The ledge at the top the cap allows for a sintered filter to be pressed into the cap.

Figure 17:
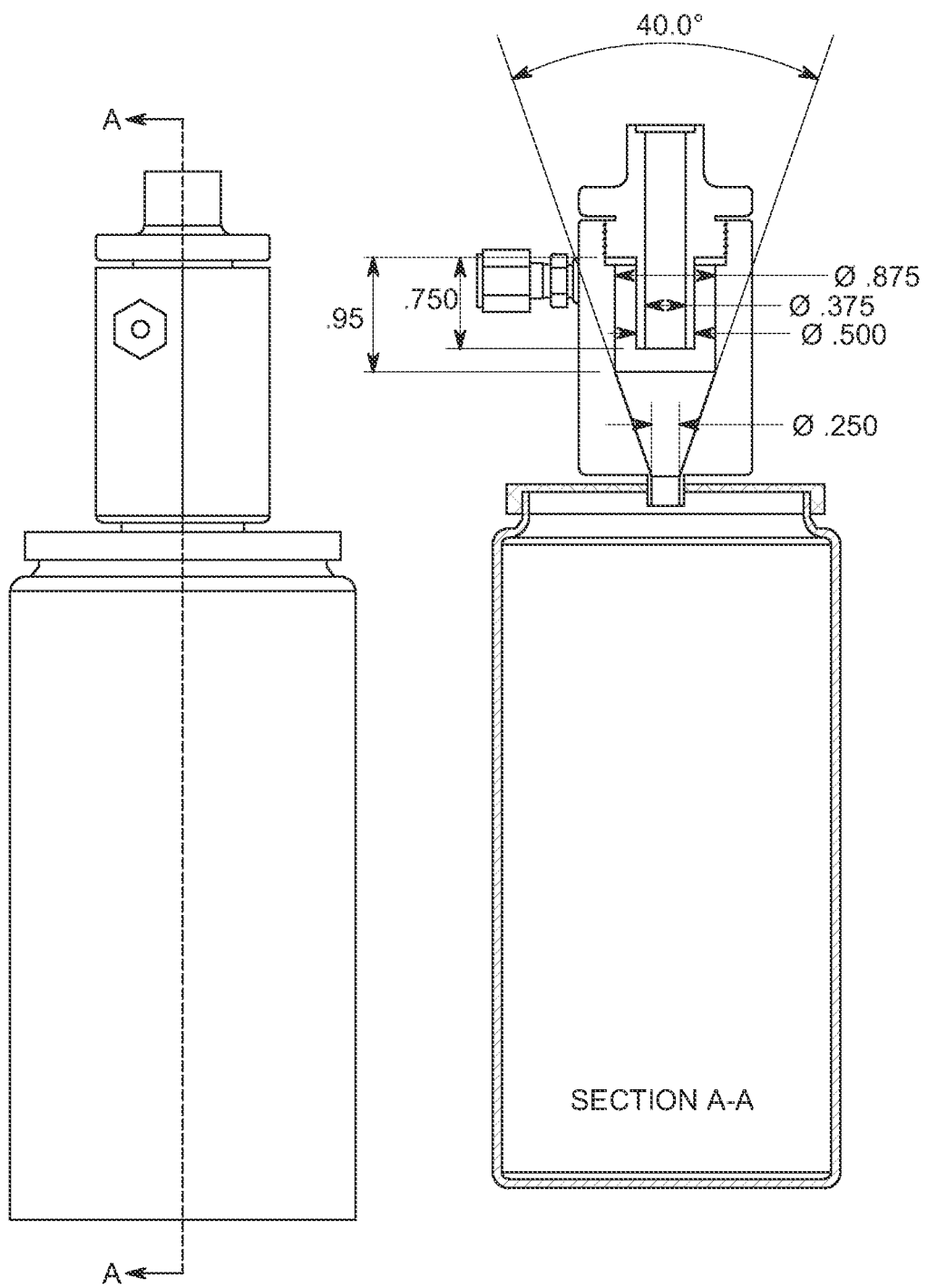
FIG. 17 illustrates a detailed internal geometry of the Collection Cyclone Assembly.

FIG. 17 illustrates the internal dimensions of the cyclone. These dimensions were honed by using CFD visualization of streamlines, as illustrated in FIG. 14. Dimensions important to the functionality include the ratio of the diameter of the outer circumference to the inner diameter of the mid-height of the funnel in the range of about 3 to about 4, e.g., about 3.5. In varying embodiments, the funnel has an angle in the range of about 30 degrees to about 60 degrees, e.g., in the range of about 35 degrees to about 55 degrees, e.g., an angle of about 30 degrees, 35 degrees, 40 degrees, 45 degrees, 50 degrees, 55 degrees, 60 degrees. The illustrated embodiment depicts a 0.875 diameter to 0.250 diameter ratio (e.g., a ratio of 3.5) along with a 40-degree funnel angle. A further important dimension includes the dimensions of the protrusion at the bottom of the cap. Generally, the depth of protrusion at the bottom of the cap extends below the tangential inlet. In varying embodiments, the depth of protrusion at the bottom of the cap extends, e.g., in the range of about 0.5 inches to about 1 inch, e.g., in the range of about, 0.6 inches to about 0.9 inches, e.g., about 0.50, 0.55, 0.60, 0.65, 0.70, 0.75, 0.80, 0.85, 0.90, 0.95 or 1.0 inches. This zone represents a part of the internal geometry of the cyclone collection assembly (see, FIG. 16).

6. Methods of Separating Molecules

Further provided are methods of performing high pressure separation and/or extraction procedures using a flash chromatography system, comprising employing the chiller or prechiller, as described above and herein. The chromatography systems comprising a pressure equalizing vessel, as described herein, are useful for the separation of molecules that can be separated using liquid chromatography, e.g., flash chromatography employing commercially available off-the-shelf column cartridges and off-the-shelf HPLC positive displacement pumps. Generally, molecules that can be successfully separated when employing a supercritical fluid solvent have a higher density than the supercritical solvent, for example, the molecules may have a higher density than supercritical, liquid phase and/or gas phase supercritical fluid (e.g., $CO_2$). In varying embodiments, the molecules to be separated in the presently described chromatography systems comprising a cyclonic separator are small organic compounds, peptides, polypeptides, lipids, carbohydrates, nucleic acids and/or polynucleotides. In varying embodiments, the molecules to be separated can have a molecular weight in the range of about 40 Daltons (Da or 40 gram/mol) to about 1,000,000 Da (g/mol), or more, e.g., in the range of about 100 Da (g/mol) to about 10,000 Da (g/mol), e.g., in the range of about 100 Da (g/mol) to about 5,000 Da (g/mol).

In varying embodiments, the methods entail inputting a sample to be separated that is dissolved or suspended in a supercritical fluid (e.g., $CO_2$), with or without co-solvent, into the inner column of the pressure equalizing vessel assembly. In varying embodiments, separation procedures are performed at flow rates in the range of about 10-300 ml/min, e.g., about 250 ml/min, and at pressures in the range of about 1000-10,000 psi, e.g., about 1500-2000 psi or about 1,750 psi. The interspace of the pressure equalizing vessel surrounding the inner column is also filled with supercritical fluid at a pressure such that the pressure differential between the pressure within the interspace and the pressure within the inner space of the inside column is less than the pressure rating of the inner column (e.g., less than about 14-200 psi). Molecules in the sample are separated according to well-known principles of liquid chromatography using commercially available and off-the-shelf flash chromatography cartridges or columns packed with solid phase media commonly used in the art.

EXAMPLES

The following examples are offered to illustrate, but not to limit the claimed invention.

Example 1: Mass Flow Rates Vs. Temperature Employing the Chiller

Figure 4:
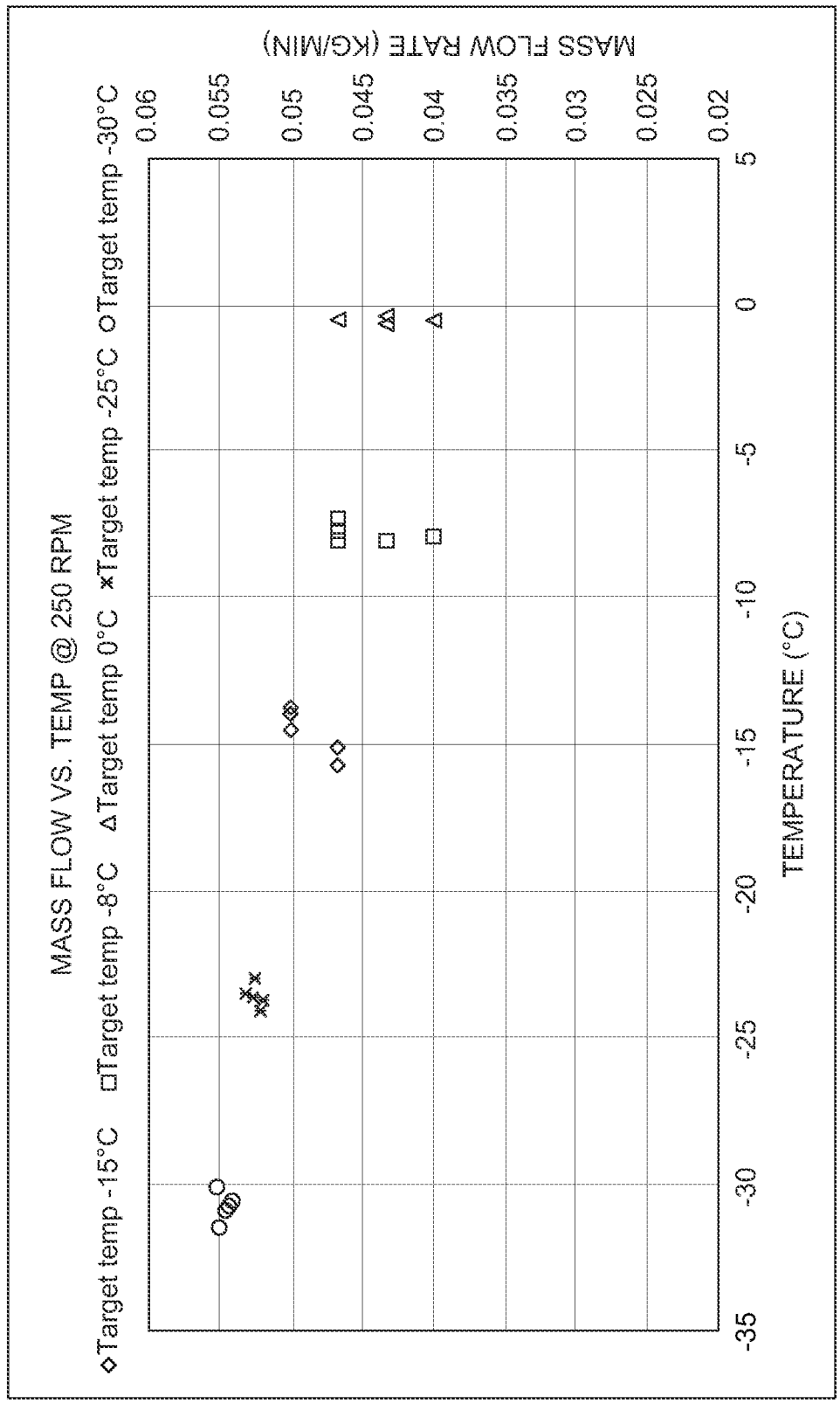
FIG. 4 illustrates a plot of mass flow rate vs. temperature at a set RPM of 250.

FIG. 4 illustrates test data for mass flow rate vs. temperature at 250 rpm pump speed. The data is focused around the temperature of −10° C. where pumping consistency increases and mass flow rate and pumping efficiency also begin to increase with decreasing temperatures. At an average temperature of 0.3° C. average mass flow rate was 0.0433 kg/min with a standard deviation of 0.0024. At an average temperature of −7.95° C., average mass flow rate was 0.0447 kg/min with a standard deviation of 0.0030. At an average temperature of −14.75° C., average mass flow rate was 0.0487 kg/min with a standard deviation of 0.0018. At an average temperature of −23.53° C. average mass flow rate was 0.0525 kg/min with a standard deviation of 0.0004. At an average temperature of −30.78° C. average mass flow rate was 0.0546 kg/min with a standard deviation of 0.0005. All tests were performed at a constant RPM of 250, with a target pressure of 2,000 psi and set point flow rate of 13 mL/min. The data shows a trend of increasing mass flow rate below −10° C. and decreased variation.

Figure 5:
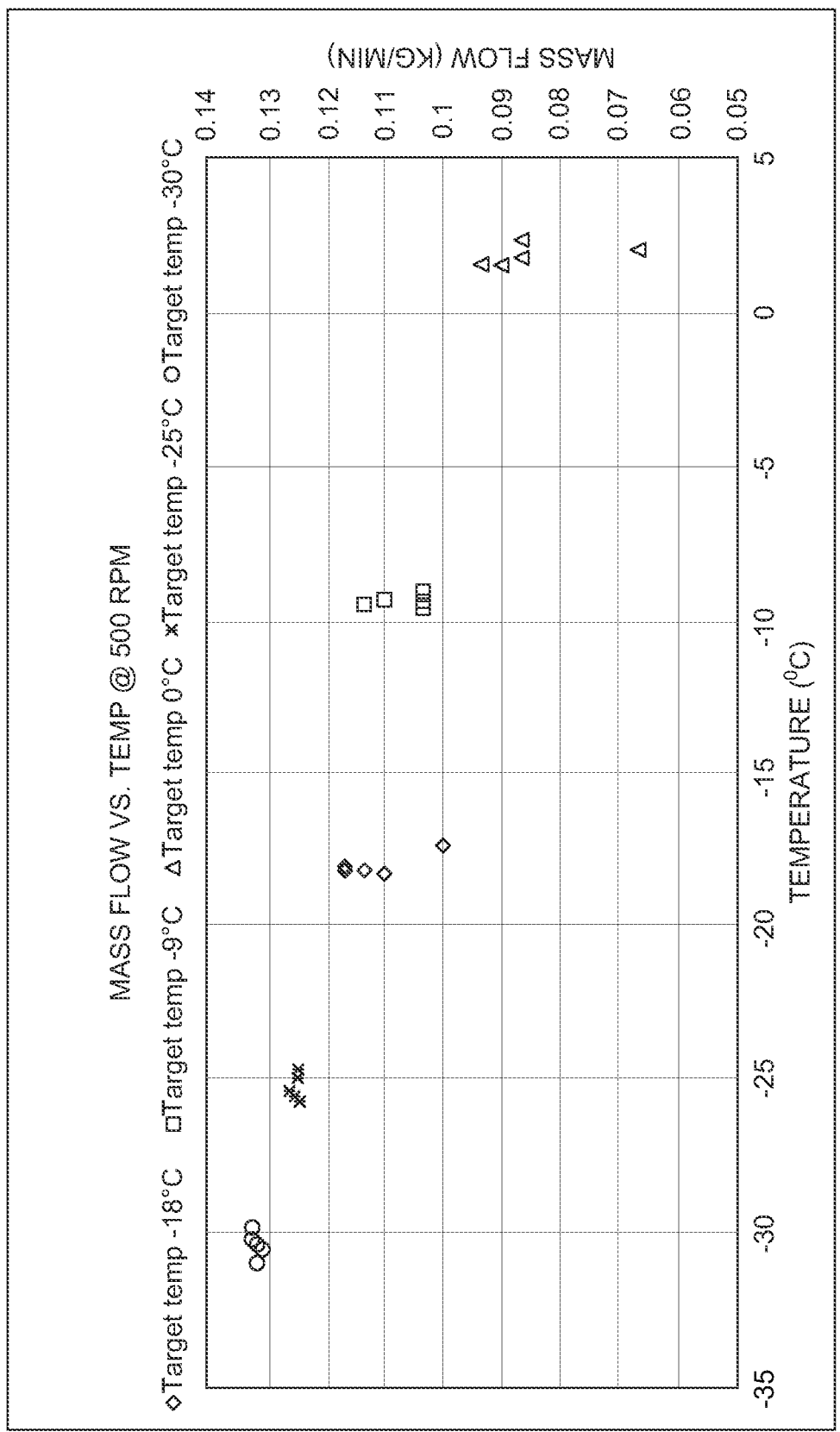
FIG. 5 illustrates a plot of mass flow rate vs. temperature at a set RPM of 500.

FIG. 5 illustrates test data for mass flow rate vs. temperature at 500 rpm pump speed. The data is focused around the temperature of −10° C., where pumping consistency increases and mass flow rate and pumping efficiency also begin to increase with decreasing temperatures. At an average temperature of 1.3° C., average mass flow rate was 0.0847 kg/min with a standard deviation of 0.0104. At an average temperature of −9.23° C., average mass flow rate was 0.1067 kg/min with a standard deviation of 0.0047. At an average temperature of −17.88° C., average mass flow rate was 0.1113 kg/min with a standard deviation of 0.0069. At an average temperature of −25.28° C., average mass flow rate was 0.125 kg/min with a standard deviation of 0.0005. At an average temperature of −30.37° C. average mass flow rate was 0.132 kg/min with a standard deviation of 0.0005. All tests were performed at a constant RPM of 500, with a target pressure of 2,000 psi and set point flow rate of 33 mL/min. The data shows a trend of increasing mass flow rate below −10° C. and decreased variation.

Figure 6:
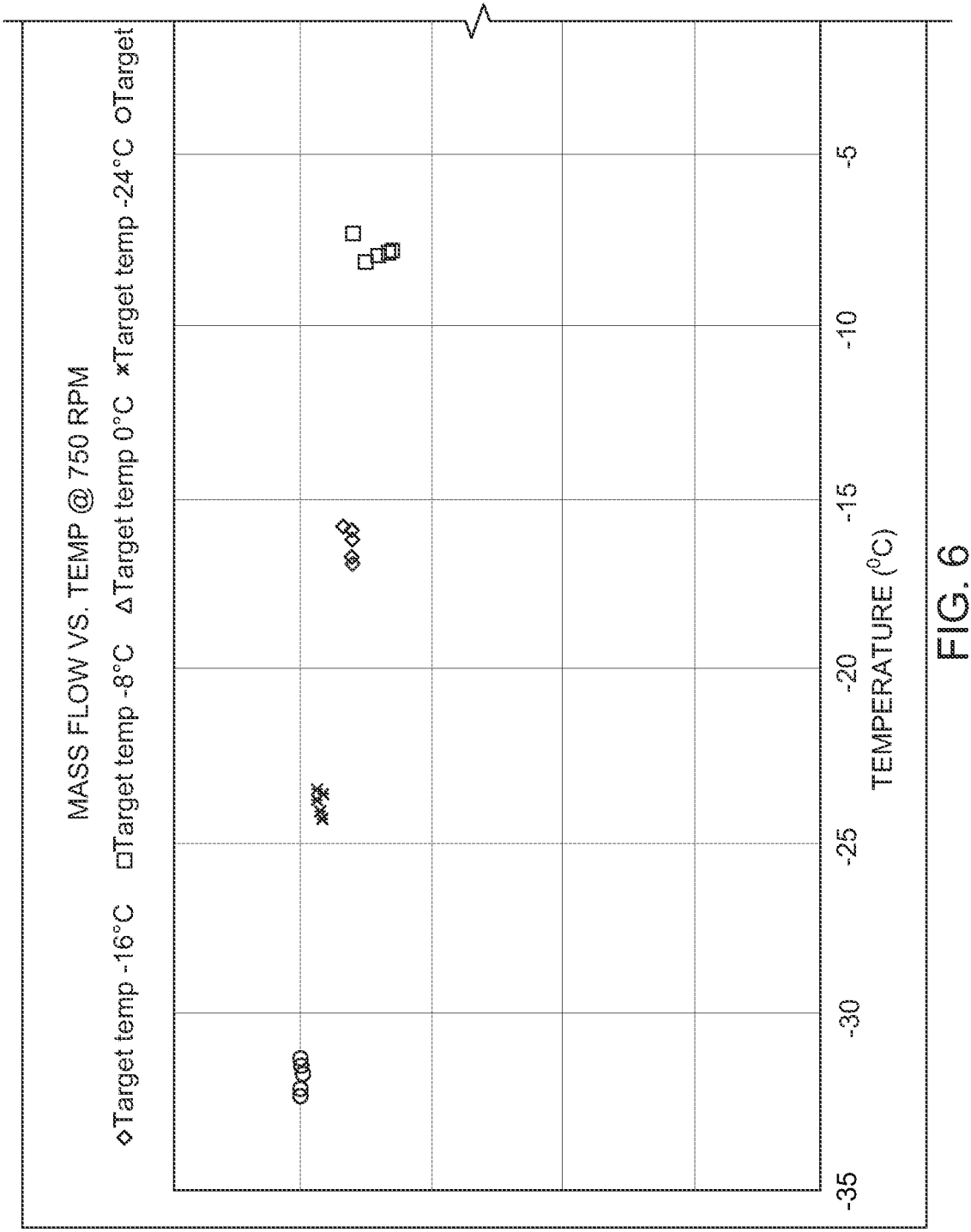
FIG. 6 illustrates a plot of mass flow rate vs. temperature at a set RPM of 750.
Figure 7:
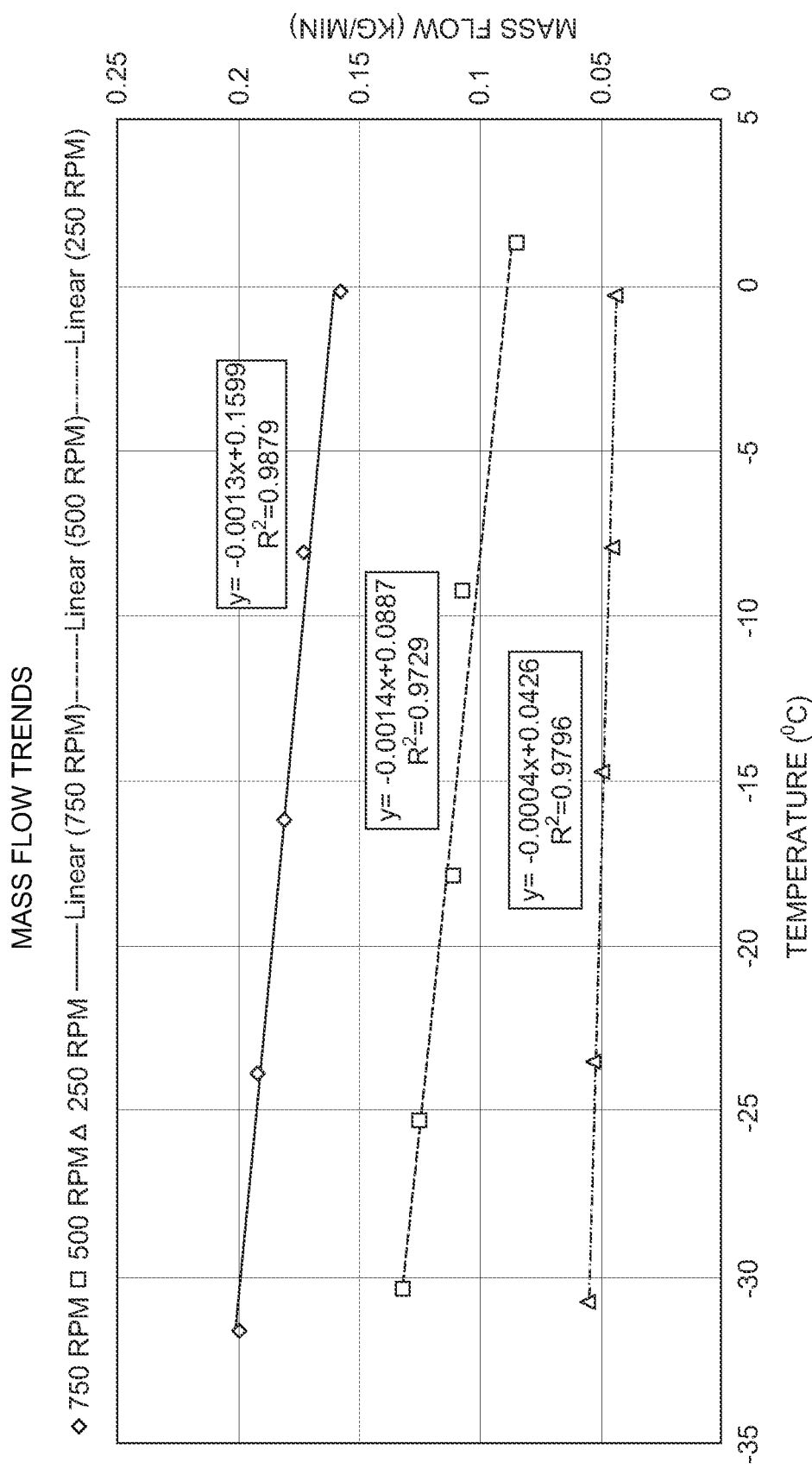
FIG. 7 illustrates trend lines for mass flow vs. temperature at the set RPMs of 250, 500 and 750.

FIG. 6 illustrates test data for mass flow rate vs. temperature at 750 rpm pump speed. The data is focused around the temperature of −10° C. where pumping consistency increases and mass flow rate and pumping efficiency also begin to increase with decreasing temperatures. At an average temperature of −0.13° C., average mass flow rate was 0.158 kg/min with a standard deviation of 0.003. At an average temperature of −8° C., average mass flow rate was 0.173 kg/min with a standard deviation of 0.0047. At an average temperature of −16.2° C. average mass flow rate was 0.181 kg/min with a standard deviation of 0.001. At an average temperature of −23.8 T C, average mass flow rate was 0.192 kg/min with a standard deviation of 0.001. At an average temperature of −31.65° C., average mass flow rate was 0.201 kg/min with a standard deviation of 0.0004. All tests were performed at a constant RPM of 750, with a target pressure of 2,000 psi and set point flow rate of 70 mL/min. The data shows a trend of increasing mass flow rate below −10° C. and decreased variation.

Example 2: Separation of Aceptophenone and Methyl Paraben 0.1 grams of Aceptophenone and 0.1 grams of Methyl Paraben were dissolved in 2 mls of Ethyl Acetate. This sample was injected into the sample loop of the SCF $CO_2$ Flash Chromatography unit with a flow rate of 50 mls/minute of SCF $CO_2$ and 10 mls/min of Ethyl Acetate at 1750 psi (120 Bar) and 50° C. These materials were separated through the 40 gram silica cartridge column and collected in cyclonic separators with a 99%+ efficiency.

The SCF $CO_2$ Flash unit, for the purposes of the present and following examples, was operated at 50 mls/minute SCF $CO_2$ and 10 mls/minute up to 17.5 mls/minute of modifier co-solvent in an isocratic or gradient mode at 1750 psi (120 bar) and 50° C. The SCF $CO_2$ Flash Chromatography unit is capable of operation up to 2500 psi (175 bar) with a SCF $CO_2$ flow rate of 250 mls/minute and co-solvent modifier flow rate of up to 100 mls/minute with a maximum operational temperature of 100°. The Ultra-Chiller cools the $CO_2$ liquid coming from the supply tank from ambient temperature down to −25° to −30° which allows for efficient and accurate pumping of the SCF $CO_2$. Once the $SCO_2$ liquid has been pumped, it flows through a pre-heater that brings the fluid from the −25° to −30° pump exit temperature up to operation temperatures of up to 100° C. The fluid streams (a supercritical fluid, e.g., supercritical $CO_2$, and Co-Solvent modifier) flow through a static mixer that ensures the homogeneous mixing of the fluids for delivery to the column assembly. Sample introduction into the unit occurs in two modes: samples dissolved in solvent up to 5 mls in size are introduced through a sample injection loop, larger samples can be introduced through a column injection manifold (reaction mixture is evaporated onto a course silica gel that is placed in the column assembly for injection).

Figure 18:
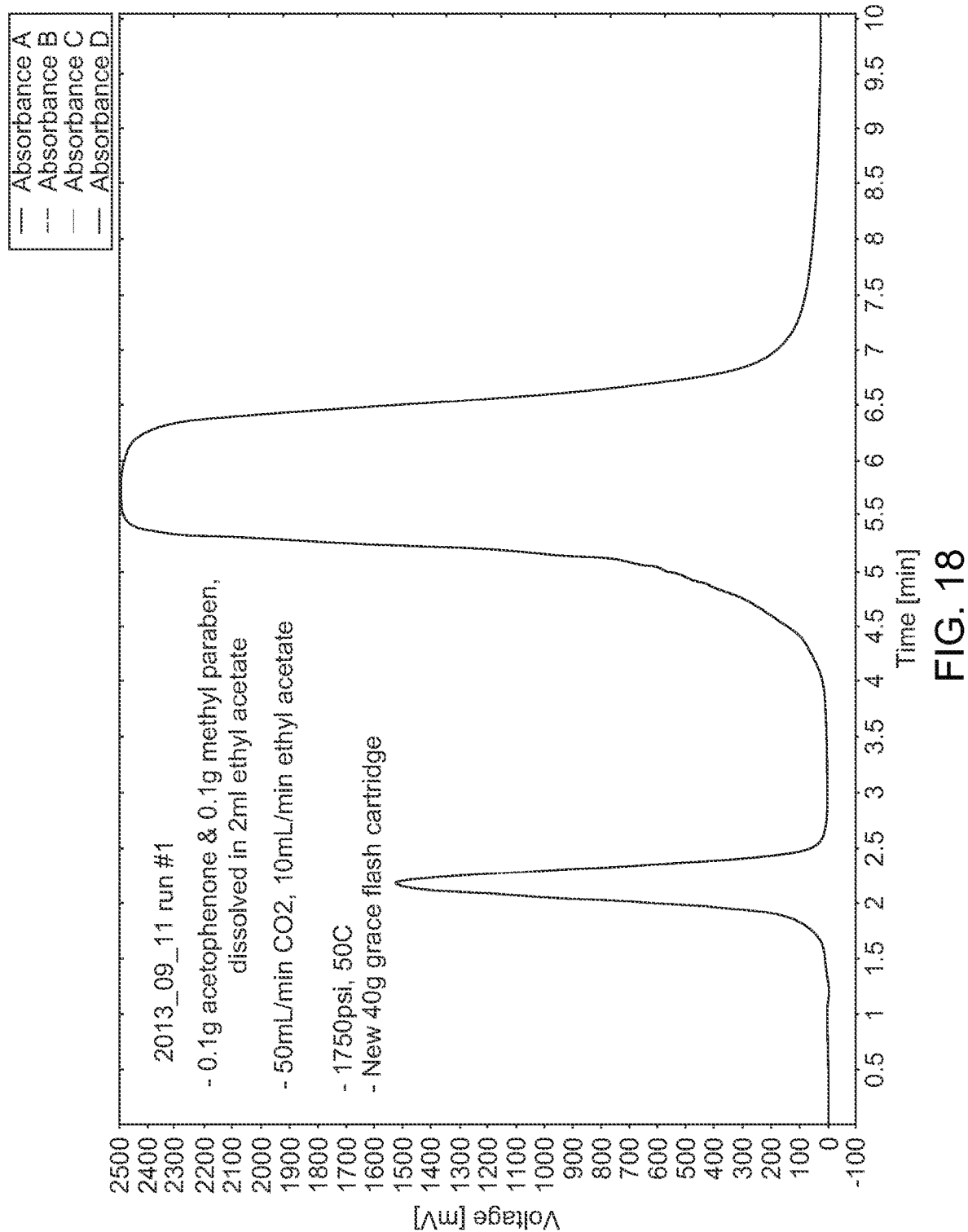
FIG. 18 illustrates a separation of aceptophenone and methyl paraben using the chromatography system described herein.

For the purposes of this work a 40 gram W. R. Grace traditional flash cartridge was used (Grace Reveleris Silica 40 micron, 40 gram, Lot #09071032, PIN 5146132, Pressure Rating 20 0 psi). However, the pressure equalizing vessel or Column Cartridge Containment Assembly can accommodate traditional flash cartridges from Grace (4 grams up to 330 grams in size) and flash cartridges from other flash chromatography vendors (Silicycle (silicycle.com), Biotage (biotage.com), Teledyne-ISCO (isco.com), Buchi (buchi.com), etc.). The UV-Vis detector was set to 254 nm to detect the fractions coming from the separation column to then be collected in the Cyclonic Separator Assemblies. Each individual peak can be collected as a pure fraction. The results are shown in FIG. 18.

Figure 19:
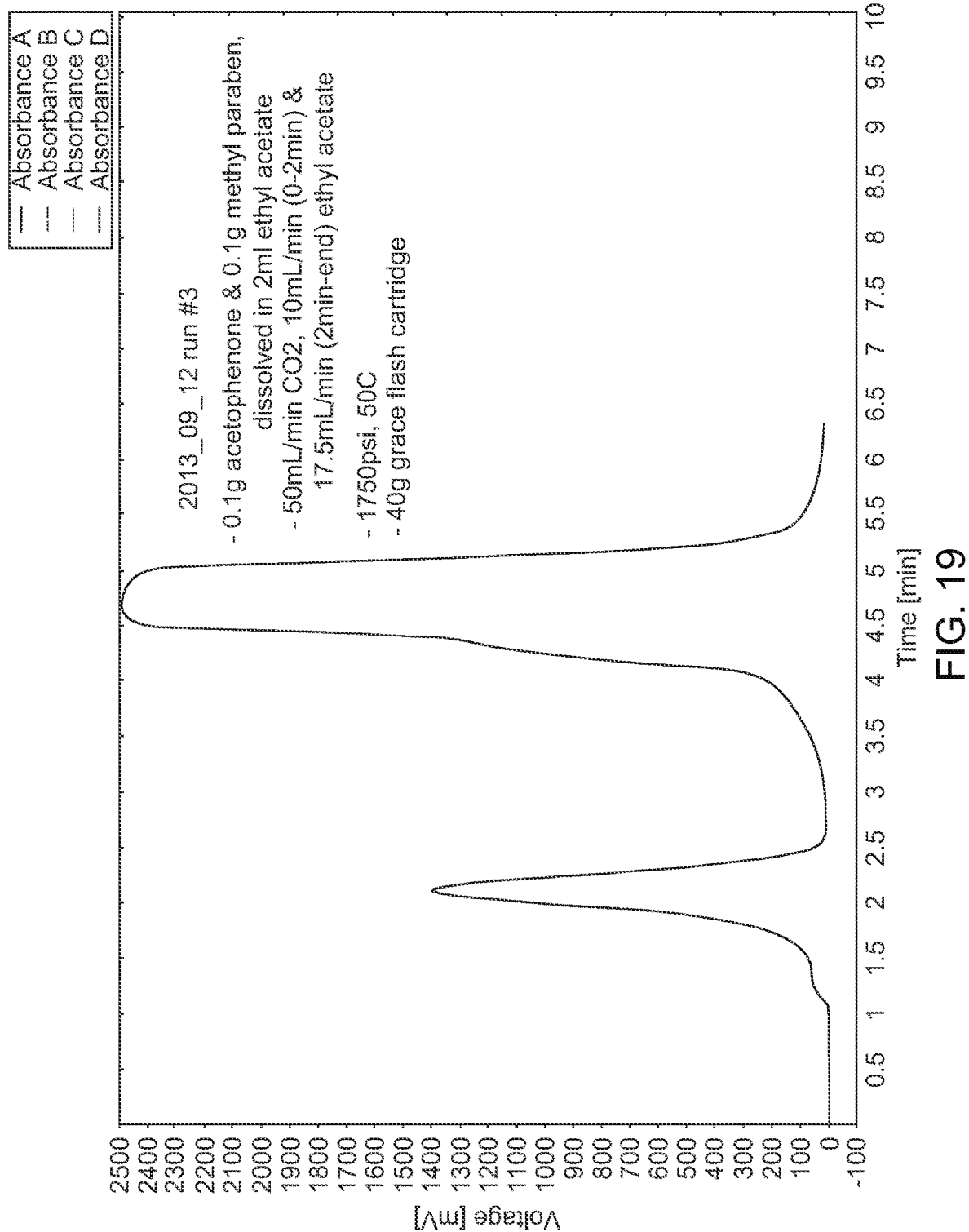
FIG. 19 illustrates a separation of aceptophenone and methyl paraben using the chromatography system described herein.

Example 3: Separation of Aceptophenone and Methyl Paraben 0.1 grams of Aceptophenone and 0.1 grams of Methyl Paraben were dissolved in 2 mls of Ethyl Acetate. This sample was injected into the sample loop of the SCF $CO_2$ Flash Chromatography unit with a flow rate of 50 mls/minute of SCF $CO_2$ and gradient of 10 mls/min to 17.5 mls/min of Ethyl Acetate at 1750 psi (120 Bar) and 50° C. These materials were separated through the 40 gram silica cartridge column and collected in cyclonic separators with a 99%+ efficiency. The results are shown in FIG. 19.

Figure 20:
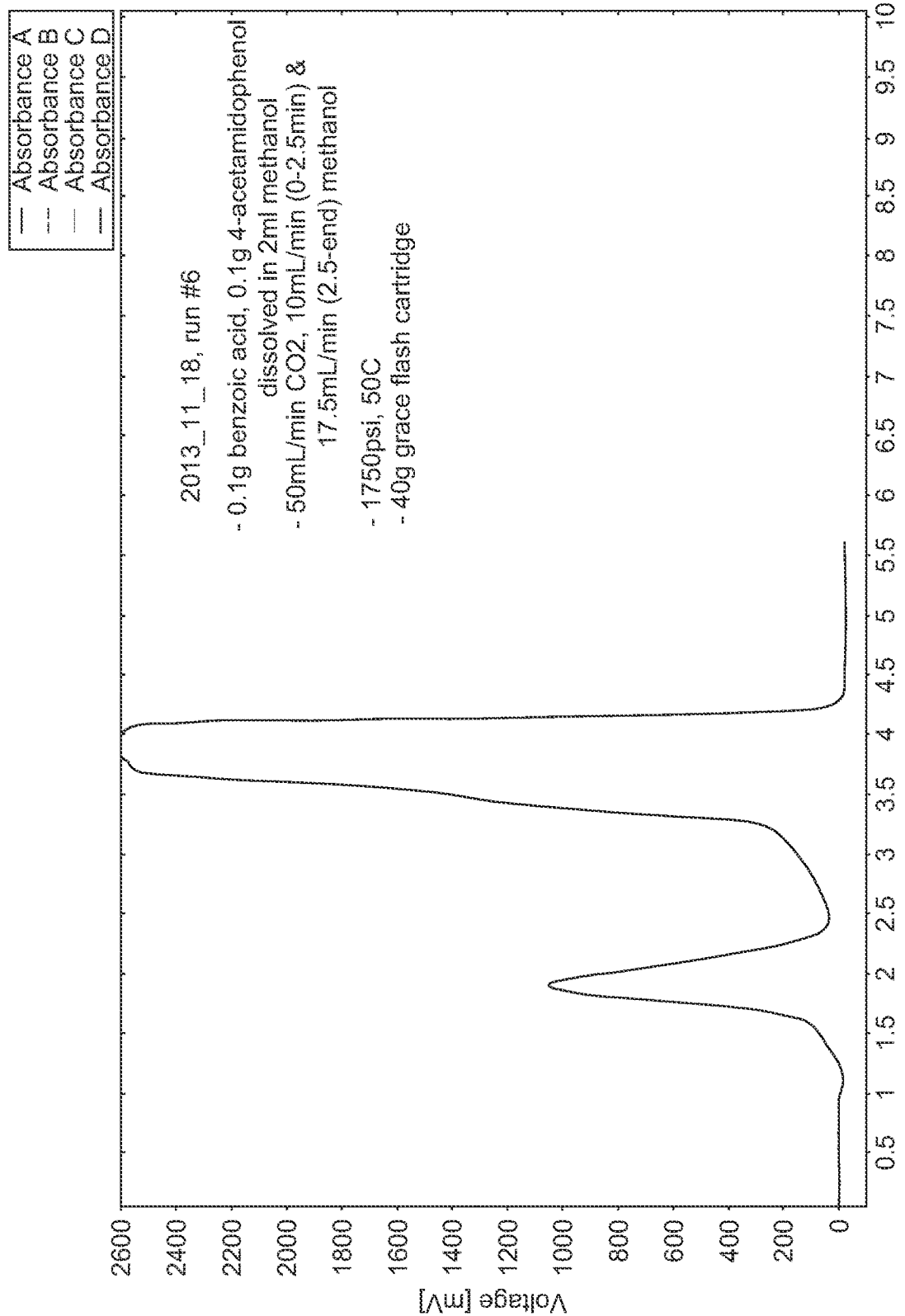
FIG. 20 illustrates a separation of benzoic acid and 4-acetamidophenol using the chromatography system described herein.

Example 4: Separation of Benzoic Acid and 4-Acetamidophenol 0.1 grams of benzoic acid and 0.1 grams of 4-acetamidophenol were dissolved in 2 mls of Methanol. This sample was injected into the sample loop of the SCF $CO_2$ Flash Chromatography unit with a flow rate of 50 mls/minute of SCF $CO_2$ and gradient of 10 mls/min to 17.5 mls/min of Methanol at 1750 psi (120 Bar) and 50°. These materials were separated through the 40 gram silica cartridge column and collected in cyclonic separators with a 99%+ efficiency. The results are shown in FIG. 20.

Figure 21:
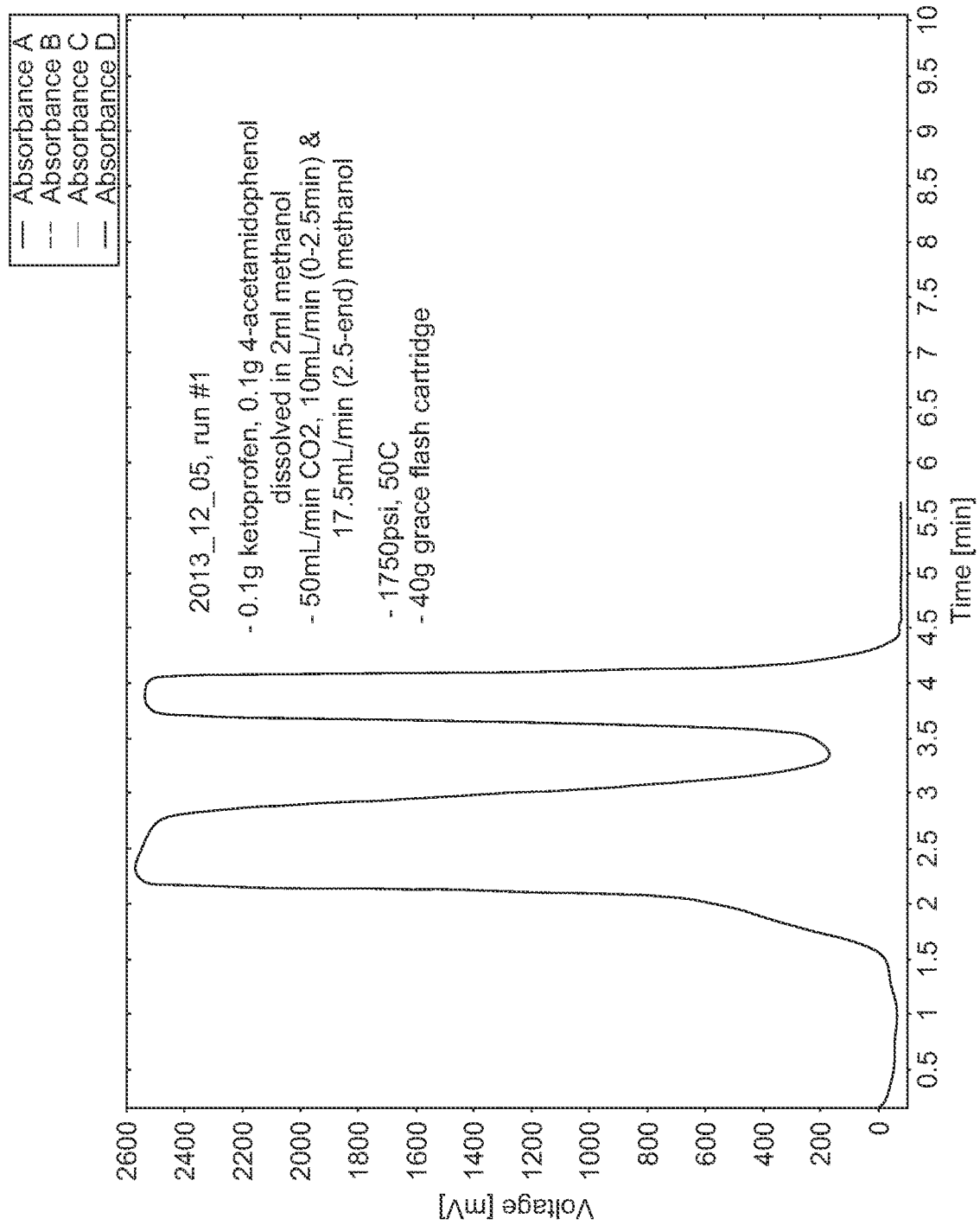
FIG. 21 illustrates a separation of ketoprofen and 4-acetamidophenol using the chromatography system described herein.

Example 5: Separation of Ketoprofen and 4-Acetamidophenol 0.1 grams of ketoprofen and 0.1 grams of 4-acetamidophenol were dissolved in 2 mls of Methanol. This sample was injected into the sample loop of the SCF $CO_2$ Flash Chromatography unit with a flow rate of 50 mls/minute of SCF $CO_2$ and gradient of 10 mls/min to 17.5 mls/min of Methanol at 1750 psi (120 Bar) and 50° C. These materials were separated through the 40 gram silica cartridge column and collected in cyclonic separators with a 99%+ efficiency. The results are shown in FIG. 21.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

7. Alternative Pressurization Methods

Alternative methods (to chilling or pre-chilling) exist to allow a non-polar solvent (e.g., $CO_2$) to perform high pressure chromatographic separation and/or extraction at or near supercritical fluid state, as a means to reduce or eliminate the need for polar (e.g., organic) solvents. One such pressurization method is disclosed in U.S. Pat. No. 8,215,922 to Berger et. al., incorporated herein by reference, wherein a set of pumps is described for pressurizing "compressible fluids" (e.g., $CO_2$) to enable flow for an ultrahigh performance chromatographic system or supercritical fluid chromatography system. The '922 Berger patent does not, however, disclose a pressure equalization means to allow for the use of this pressurized supercritical fluid technique with traditional disposable cartridges as the separation column, which is not designed to withstand high pressure. Utilizing the pressure equalization techniques described herein, one may utilize the set of pumps disclosed in the Berger '922 patent to pressurize and meter flow of a non-polar solvent at or near supercritical phase and employ this technique with traditional disposable cartridge systems.

8. Alternative Separation Methods

Alternative methods (to cyclonic separation) exist to separate and collect sample molecules from a liquid phase or gas phase stream of pressurize non-polar solvent (e.g., $CO_2$) utilizing chromatographic separation and/or extraction techniques at or near supercritical fluid state, as a means to reduce or eliminate the need for polar (e.g., organic) solvents. One such separation method is disclosed in U.S. Pat. No. 6,413,428 to Berger et. al., incorporated herein by reference, wherein a controlled decompression system is disclosed to allow for phased (step-down) pressure reduction or decompression to efficiently control separation and collection of desired sample molecules. The '428 Berger patent does not, however, disclose a chilling or pre-chilling technique to allow for pressurization of non-polar solvent at or near supercritical fluid state and subsequent flow through the system with a single non-polar solvent pump (unlike the discloser in the Berger '922 patent). Utilizing the chilling or pre-chilling techniques described herein, one may utilize the separation and collection by non-polar solvent decompression disclosed in the Berger '428 patent to fractionally separate and collect sample molecules from the pressurized system, thereby reducing or elimination the need for polar solvents.

9. Alternative Separation Methods

A Pressure Containment Assembly (PCA) can be employed in the Medium Pressure Liquid (Flash) Chromatography. Typical operation pressures of these units is 5-50 Bars (75-725 psi). Medium Pressure Liquid Chromatography (HPLC) is one of the various preparative column chromatography techniques for separation of materials. Separation under elevated pressures renders the use of smaller particle size column packing supports possible (typical stationary phase particles in the columns of size 15-40 µm particle size are used) and increases the diversity of usable stationary phases for the column cartridges. This separation method is now routinely used beside or in combination with the other common preparative tools (e.g. ISCO, Biotage, and Grace). Using PCA affords significant cost advantage by allowing use of less expensive plastic column cartridges.

It is herein disclosed and taught how PCA "pressure balancing" may be used to counter the pressure applied to the solvent flow stream that is thus exerted on the interior of the plastic column cartridge. Using an inert gas (e.g., Nitrogen or Air) one may employ PCA in a traditional all solvent medium pressure flash chromatography unit.

The control logic for the PCA includes a pressure transducer, located upstream of the PCA, reading pressure from the solvent flow stream and communicating these pressure readings to a control value capable of applying counter-balancing pressure from an inert gaseous source (N2/Air) delivered to the PCA (5-50 bars, 75-725 psi). The pressure of the inert gas introduced into the PCA is at or near the same pressure and rate of pressure increase as the solvent flow stream being delivered to the interior of the column. The PCA may also be decompressed at the same pressure and rate of pressure decrease as the solvent flow stream exiting the interior of the column at the end of a process run. The pressure balancing provided through the PCA ensures that the disposable plastic cartridge/separation column will neither burst nor be crushed by a pressure differential exceeding its design limits.

Figure 22:
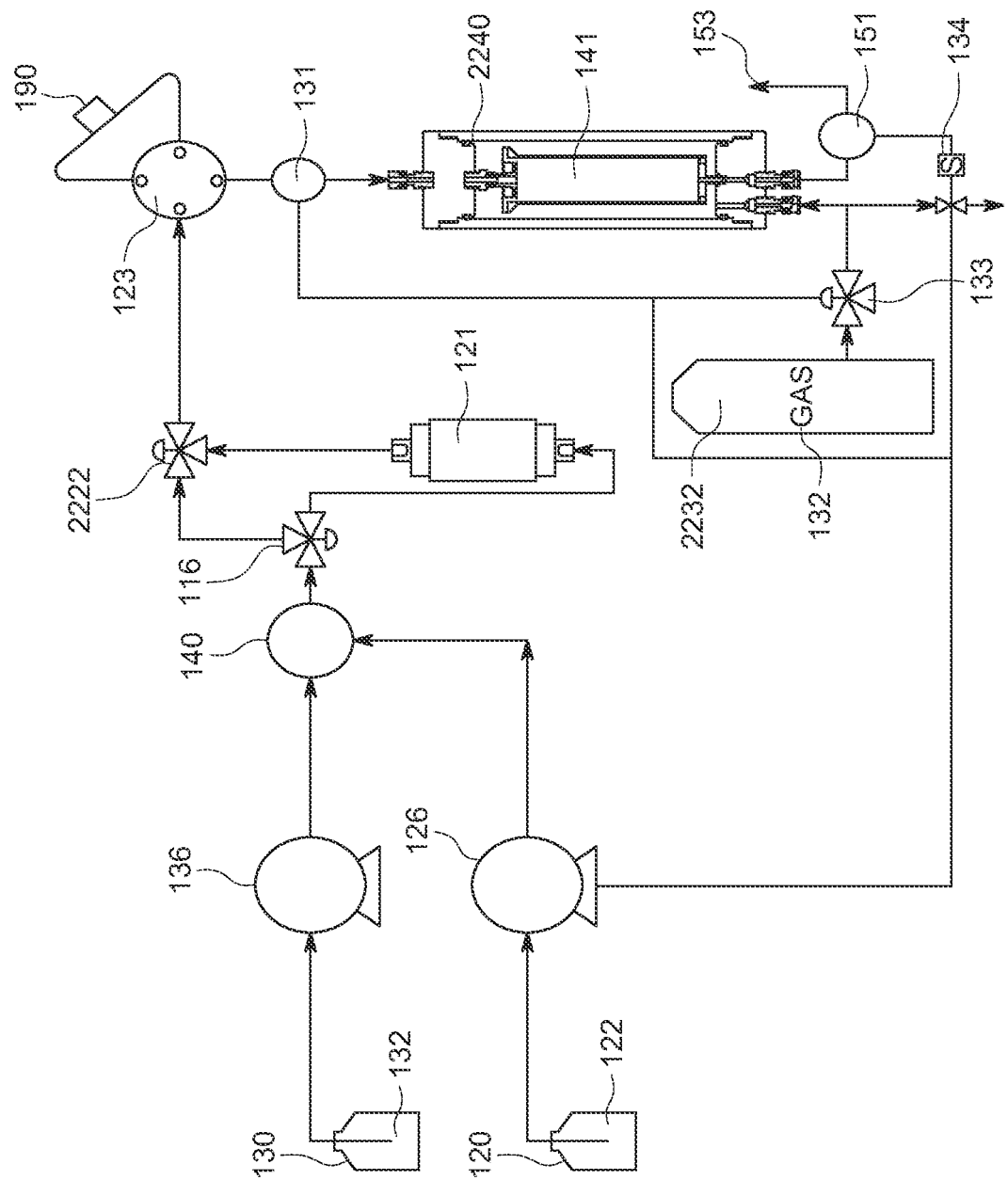
FIG. 22 illustrates a schematic layout of a medium pressure flash chromatography system according to a preferred embodiment of the invention.
Figure 23:
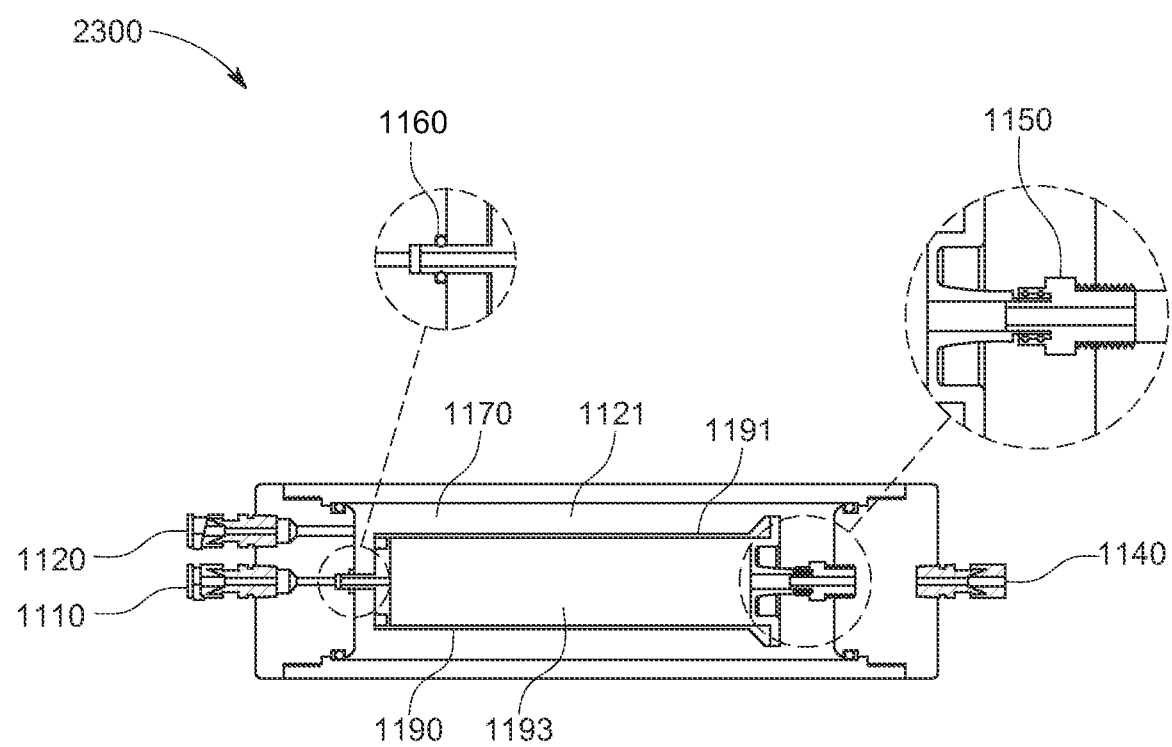
FIG. 23 illustrates a cross sectional view of a pressure equalization system, i.e., pressure containment assembly according to a preferred embodiment of the invention.

The schematic layout of a medium pressure flash chromatography system 2200 according to a preferred embodiment of the invention is disclosed in FIG. 22. The system includes two sources of traditional solvent, solvent source 132 and co-solvent source 122. Each solvent is fed into the system through a solvent pump, solvent pump 136 and co-solvent pump 126. The pumped/pressurized solvents mix within the system at static mixer 140. Valve 116 determines whether the pressurized solvent mixture flows to a sample injection vessel 121 (for larger samples) or sample injection valve 123. Valve 2222 is position to receive and direct flow streams exiting sample injection vessel 121 and valve 116. From valve 2222, the flow stream is directed to sample injection valve 121. Thus, the example sample injection manifold illustrated in FIG. 22 allows for sample injection into the loop through sample injection valve 123 or through a secondary injection column (sample injection vessel 121), intended for larger sample injection. Continuing with the schematic layout of FIG. 22, once the flow stream exits sample injection valve 123, the flow stream mixture now includes the solve, co-solvent and sample. At this point, a pressure reading from a pressure transducer will dictate the amount of pressurized gas to be released from gas pressure source 2232 (e.g., a pressurized air or N2 gas tank/canister) through control valve 133 to provide a pressure balance into pressure containment assembly 2240. The pressure reading may be obtained from a transducer that is part of one of the solvent pump assemblies, such as the reading from co-solvent pump 114 as illustrated in FIG. 22. Alternatively or additional, the pressure reading may be obtained for a separate pressure transducer such as pressure transducer 131, again, as illustrated in FIG. 22. Valve 133 may further be capable of obtaining pressure readings from multiple transducer sources. The type of gas to be used at gas pressure source 132 should be an inert gas, such as air or nitrogen (N2). Further describing the schematic layout of FIG. 22, pressure containment assembly 2240 is configured to hold plastic cartridge/column 141, which may be an industry standard disposable cartridge containing silica gel for chromatographic separation. These standard plastic cartridges are not designed to withstand elevated pressures, thus pressure containment assembly 2240 allows for balancing, to an acceptable differential, the internal and external pressures applied to the cartridge walls during system operation. Concluding the description of FIG. 22, solenoid valve vent 134 is utilized to regulate the depressurization of pressure containment assembly 140. Venting of the pressurized gas at solenoid valve vent 134 is dictated by a pressure reading from a pressure transducer. The pressure reading may be obtained a pressure transducer that is part of one of the solvent pumps or, alternatively, from a separate pressure transducer such as pressure transducer 131 or pressure transducer 151, as illustrated in FIG. 22. The valves may further be capable of obtaining pressure readings from multiple transducer sources. Without regulation of the gas pressure by controlled venting at solenoid valve vent 134, plastic cartridge/column 141 may be crushed (implode) due to exceedingly high pressure outside the cartridge relative to the sample stream pressure inside the cartridge. Similarly, without regulation of the gas pressure controlled by valve 133 receiving pressure reading input from transducer 131, the cartridge may explode due to exceedingly high sample stream pressure inside the cartridge relative to the pressure outside the cartridge. The sample collection stream outlet 153 is shown Turning to FIG. 23, this figure illustrates a cross sectional view of the pressure equalization system 2300, i.e., pressure containment assembly 2340, of an exemplary medium pressure flash chromatography system, the assembly incorporating plastic cartridge/column 1190. FIG. 23 illustrates the location of the input, inlet 1140, of a combined solvent and sample flow stream, and shows how the system equalizes (i.e., counterbalances) the pressure of this flow stream with a pressure equalizing gas input from inlet 1120. The fitting shown in FIG. 23 is a high pressure compression fitting made to seal on the outside diameter of appropriately sized high pressure tubing. The same type of fitting is used for sample stream outlet 1110, and pressure equalizing inlet 1120. The pressure equalizing medium will typically be an inert gas (e.g., air or N2).

A combined solvent and sample flow stream is introduced at inlet 1140. Input of the combined solvent and sample flows through the contents of cartridge 1190. The internally exerted pressure of the flow stream within cartridge 1190 is balanced by the externally exerted pressure of the pressure equalizing gas 1121 on the exterior 1191 of cartridge 1190. System pressure is controlled by pressure transducer readings. Transducers may be located upstream of inlet 1140 or downstream of outlet 1110, or both.

The pressure of the equalizing gas input at inlet 1120 may be moderately higher on the outside of cartridge 1190, but still within pressure tolerance rating of cartridge 241, as compared to the pressure from the flow stream on the inside 1193. By ensuring that any moderate differential favors higher external pressure, any leaks to cartridge 1190 would result in inert gas movement into cartridge, rather than a loss of the combined solvent and sample flow stream out of cartridge. This protects valuable sample material from being lost.

10. Combination of Various Methods

Certain components and elements of the systems and methods disclosed herein may be combined in various innovative ways.

In one such example, the system may be a chromatography system with reduced solvent volumes using multiple pumps as pressure sources on flow streams containing highly pressurized gas, compressible liquid, or supercritical fluid, comprising: a primary pump for pumping a relatively compressible solvent fluid flow stream; a secondary pump for pumping a first relatively incompressible fluid flow stream; a mixing device that combines said first and second flow streams into a combined flow stream; an injection device that can introduce samples or solutions into any of said flow streams; and a pressure equalizing vessel downstream of said injection device, wherein the pressure equalizing vessel comprises an inner chromatography column comprising stationary phase media and an outer column that cylindrically surrounds the length of the inner column, wherein no part of the inner column is exposed to full internal pressure without balancing external equalizing pressure. This chromatography system may further include a pressure equalizing vessel that has interspace of a width of at least 1 mm between the inner diameter of the outer column and the outer diameter of the inner chromatography column, and/or an outer column that withstands pressures of at least about 500 psi and even up to 10,000 psi.

In another such example, the system may be a chromatography system with reduced solvent volumes using multiple pumps as pressure sources on flow streams containing highly pressurized gas, compressible liquid, or supercritical fluid, comprising: a primary pump for pumping a relatively compressible solvent fluid flow stream; a secondary pump for pumping a first relatively incompressible fluid flow stream; a mixing device that combines said first and second flow streams into a combined flow stream; an injection device that can introduce samples or solutions into any of said flow streams; a chromatography separation column, downstream of said mixing device and that can receive said combined flow stream; a cyclonic separator downstream of said injection device, to allow for samples to be collected and recovered, wherein the cyclonic separator comprises a cyclone body comprising an inner surface, an outer circumference, a top outlet, a tangential inlet and a bottom outlet. This chromatography system may further include a cyclonic separator wherein (i) the top portion of the inner surface of the cyclone body comprises screw threads, (ii) the middle portion of the inner surface of the cyclone body is cylindrical, and (iii) the bottom portion of the inner surface of the cyclone body comprises a funnel. This chromatography system may further include a cyclonic separator wherein the funnel has an angle in the range of about 30 degrees to about 60 degrees and wherein the ratio of the diameter of the outer circumference to the inner diameter of the mid-height of the funnel is in the range of about 3 to about 4. This chromatography system may further include a cyclonic separator wherein the cyclone body comprises a cap comprising a sintered filter and screw threads, and wherein the screw threads of the cap interlock with the screw threads on the inner surface of the top portion of the cyclone body. This chromatography system may further include a cyclonic separator wherein the cyclonic separator can withstand pressures of at least about 1000 psi, and wherein the body is in fluid communication with the cap.

In another such example, the method may be a method of performing chromatography using a disposable cartridge, the method comprising the steps of: i) providing a pressurized vessel and a disposable plastic flash chromatography cartridge removably attached by a fitting to the vessel, wherein the cartridge is loaded with silica or modified silica gel; ii) transporting a flow stream of gas, liquid, or supercritical fluid through a first refrigerant circuit wherein the first refrigerant circuit comprises (a) a first compressor that pumps refrigerant, and (b) a first tube-in-tube heat exchanger in fluid communication with the first compressor, wherein the first tube-in-tube heat exchanger comprises an inner lumen and an outer lumen that surrounds the inner lumen, and wherein the refrigerant flows through the outer lumen; iii) further chilling the flow stream by transporting the flow stream through a cryogenic refrigerant circuit in thermodynamic communication with the first refrigerant circuit where the cryogenic refrigerant circuit comprises a second compressor that (A) pumps cryogenic refrigerant through the cryogenic refrigerant circuit, and (B) is in fluid communication with the first tube-in-tube heat exchanger; wherein the cryogenic refrigerant flows through the inner lumen, and wherein cryogenic refrigerant circuit further comprises a second tube-in-tube heat exchanger in fluid communication with the first tube-in-tube heat exchanger, and wherein the second tube-in-tube heat exchanger comprises an inner lumen and an outer lumen that surrounds the inner lumen, wherein the cryogenic refrigerant flows through the outer lumen and wherein the flow stream becomes further chilled while flowing through the inner lumen; iv) transporting the further chilled flow stream out of the inner lumen of the second tube-in-tube heat exchanger; v) injecting a sample into the flow stream; vi) receiving the flow stream and sample in an inlet of the cartridge; and vii) collecting fractions of the flow stream exiting an outlet of the cartridge in a collection tray. This chromatography method may further include a method wherein the fitting on the disposable plastic flash chromatography cartridge is a luer lock fitting, and/or the disposable plastic flash chromatography cartridge comprises two ends, a fitting end and a seal end, and/or the seal end is sealed to the column using an O-ring;

and/or the seal end is sealed to the column using a gasket, and/or the disposable plastic flash chromatography cartridge has a stationary phase media capacity of between 4 grams and 350 grams. This chromatography method may also include a method wherein the pressurized vessel is equipped to fit with a range of differently sized disposable plastic flash chromatography cartridges, and/or the cartridge has a diameter ranging in size from 0.5 inches to 3.5 inches and a length ranging in size from 3.5 inches to 11 inches.

In another such example, the method may be a method of performing chromatography with reduced solvent consumption in a disposable-cartridge chromatographic system, the method comprising the steps of: i) pumping carbon dioxide through a primary pump to allow the carbon dioxide gas to reach a supercritical fluid phase and function as a non-polar solvent in a chromatographic system; ii) pumping a polar co-solvent through a secondary pump, wherein the polar co-solvent comprises less than or equal to 20 percent of the total volume concentration of the total solvents used in the chromatographic system; iii) mixing the polar solvent and the non-polar solvent into a combined flow stream; iv) injecting a sample into the combined flow stream, wherein the sample is a material to be chromatographically separated; v) receiving the sample and combined flow stream into a disposable plastic cartridge attached to a pressurized vessel, wherein the cartridge is a chromatographic column loaded with silica or modified silica gel; and vi) collecting fractions of the separated sample from the flow stream exiting an outlet of the cartridge in a collection tray. This chromatography method may further include a method wherein the carbon dioxide is pre-chilled and passed through a single primary pump before the mixing step, or, wherein the carbon dioxide is not pre-chilled and is passed through a series of primary pumps before the mixing step. The chromatography method may alternatively include a method using chilled carbon dioxide in a disposable-cartridge chromatographic system, the method comprising the steps of: chilling a stream of carbon dioxide gas by transmitting the carbon dioxide through a chiller wherein the carbon dioxide output from the chiller is at least about 35° C. lower than the carbon dioxide input into the chiller; ii) pumping the chilled carbon dioxide stream through a single, primary, piston-style positive displacement pump; iii) without pumping the chilled carbon dioxide stream through an additional pump, injecting a sample into the carbon dioxide stream, wherein the sample is a material to be chromatographically separated; iv) receiving the sample and carbon dioxide stream into a disposable plastic cartridge attached to a pressurized vessel, wherein the cartridge is a chromatographic column loaded with silica or modified silica gel; and v) collecting fractions of the separated sample from the flow stream exiting an outlet of the cartridge in a collection tray. This chromatography method may further include a carbon dioxide stream that is combined with a separate flow stream of polar solvent constituting 20% or less of the total volume concentration of the combined polar solvent and carbon dioxide stream, and/or a carbon dioxide stream that is chilled to a temperature in the range of about −10° C. to about −40°, and/or a carbon dioxide stream pumping through a single piston-style positive displacement pump with a mass flow rate that is repeatable and proportionate to the pump speed.

In another such example, the method may be a method of separating a sample into constituent parts using a high pressure liquid chromatography device with a disposable plastic column cartridge, comprising: inserting the disposable plastic column cartridge into a pressure containment area of the chromatography device, wherein the cartridge has inlet and outlet sections and is preloaded with silica gel; pressurizing a flow stream of solvent; introducing a sample into the pressurized solvent flow stream; maintaining, within a pressure containment assembly, a pressure balance between external pressure on the cartridge applied within the pressure containment area and internal pressure on the cartridge applied through the introduction of pressurized solvent flow stream and sample mixture; wherein the external pressure is applied through an inert gas source that is controlled by a pressure control value influenced by a pressure transducer reading the pressure of the combined sample and solvent flow stream entering the cartridge, and; wherein the pressure balance in maintained in such a way so that the difference in pressure between the exterior and interior of the cartridge is at all times less than the difference in pressure that would cause mechanical warping that would damage a wall of the cartridge.

Figure 24:
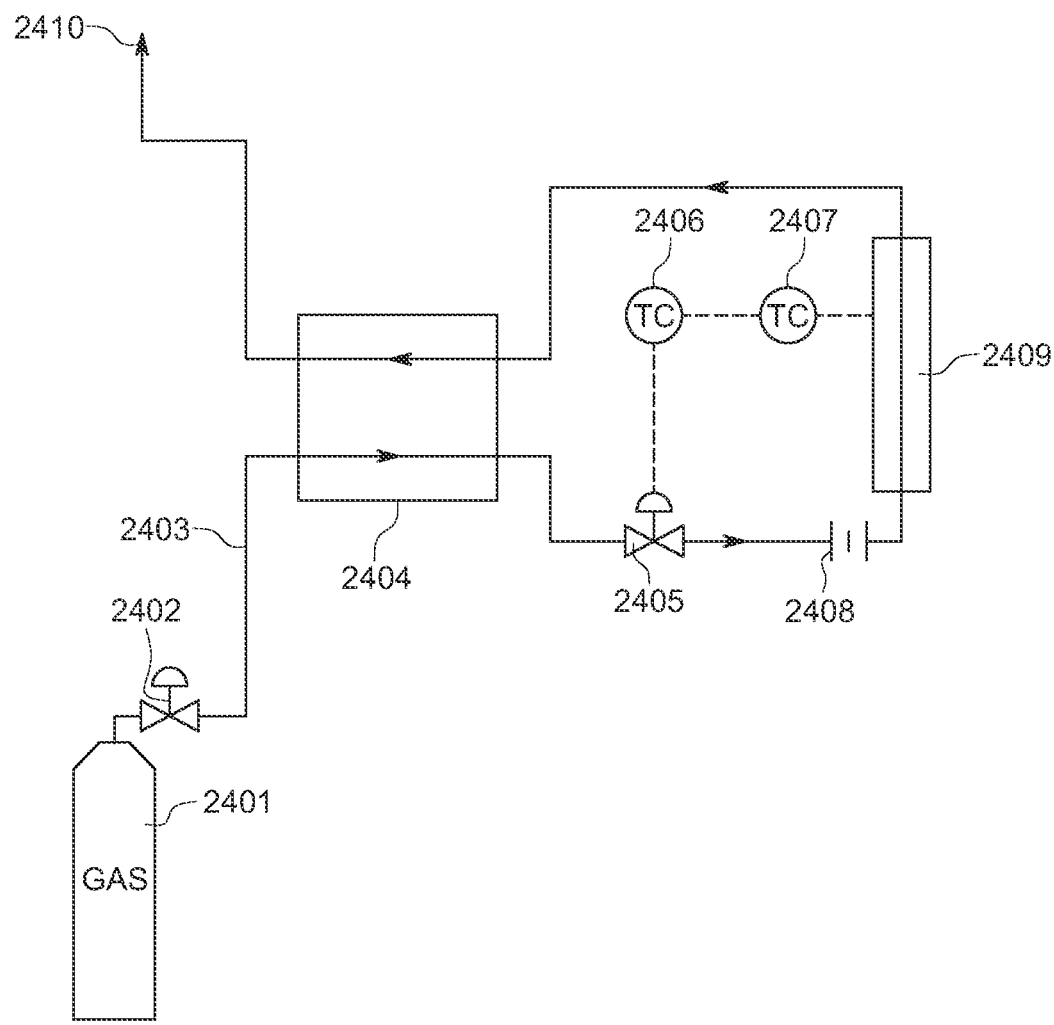
FIG. 24 illustrates a cooling system with an expansion device designed to impart fluid expansion to effectuate heat transfer where needed in the system.
Figure 25:
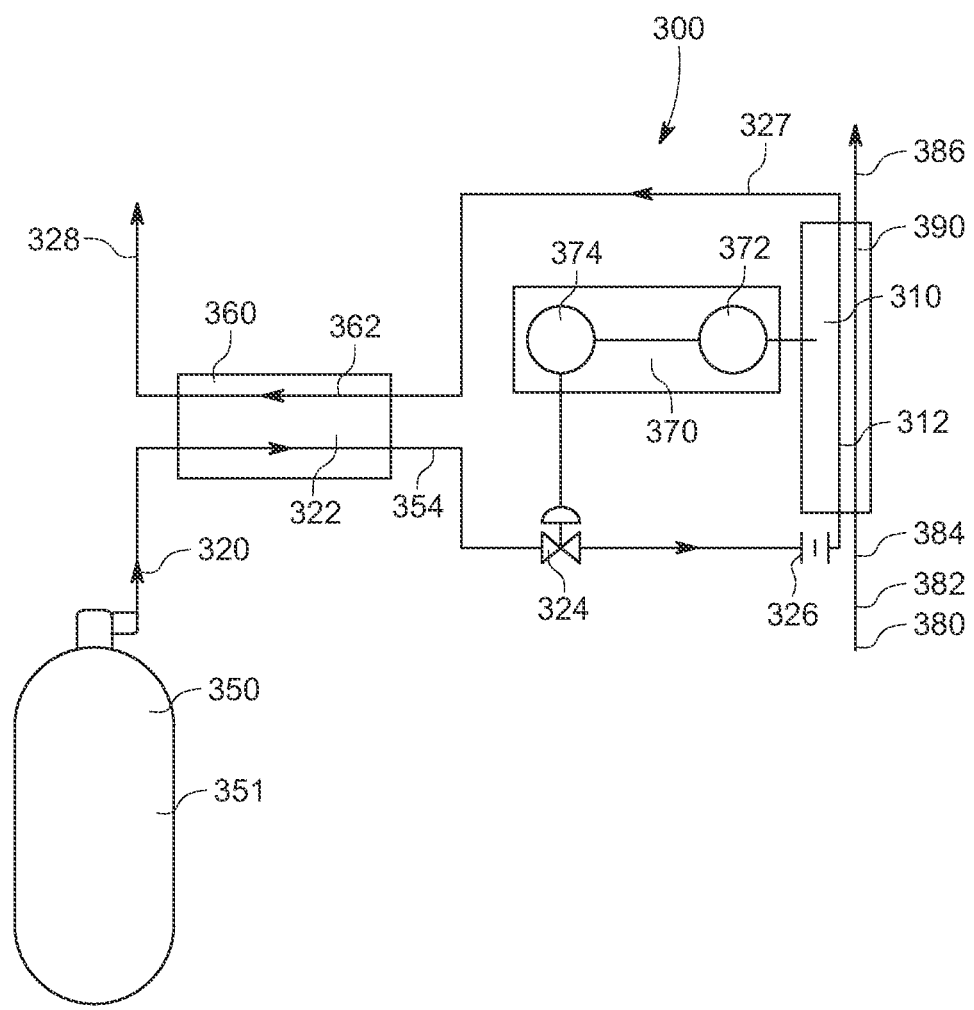
FIG. 25 illustrates an open loop cooling circuit for the refrigerant, wherein the refrigerant flows from a compressor through an inlet heat exchanger before passing to the first tube-in-tube heat exchanger.

In another such example, there may be a cooling method comprised of the expansion of a fluid with a positive Joule-Thomson coefficient from an area of high pressure to one of lower pressure without capturing or recompressing the fluid, such as shown in FIG. 24, where expansion is accomplished by passing the fluid through an expansion device 2408 with one or more orifices or capillaries and the expansion device is placed in close proximity to where the cooling effect is needed (e.g., object 2409); the expanded fluid may be passed through larger diameter channels to increase the residence time and surface area and allow the cold low pressure fluid to absorb energy from the object being cooled; the larger diameter channels can be machined directly into the object being cooled for superior heat transfer. Further efficiencies can be obtained by using the low pressure fluid as it is exhausted and has approached temperature equilibrium with the object being cooled to cool the incoming high pressure fluid before expansion (e.g., optional heat exchanger 2404) to reduce its enthalpy. This can be accomplished with a counter flow or other heat exchanger. The amount of cooling and/or temperature of the device being cooled can be controlled using feedback from a temperature sensor 2407 placed on the device being cooled 2409. A valve 2405 from this sensor is used to control (e.g., via temp. controller 2406) the flow into the pressure reduction device 2408. This cooling method and systems 2403 utilizing this method will have numerous advantages such as very compact, low noise, low equipment cost, low operating cost, and the ability to reach lower temperatures that many conventional refrigeration systems. The Joule-Thomson fluid may be exhausted from the system through exhaust 2410. A valve 2402 may control the flow of pressurized fluid 2401 into the system As shown in FIG. 25, an exemplary open loop cooling circuit 300 comprises a refrigerant inlet heat exchanger 360 for pre-cooling the cooling fluid 350, such as a refrigerant, prior to expansion and flow into the primary heat exchanger 310, which may be a tube-in-tube heat exchanger 312. A cooling fluid, such as a fluid having a positive Joule-Thomson coefficient, may be provided from a compressor 351, such as a compressed gas cylinder, and flow as source cooling fluid 320 to the inlet heat exchanger 360. The cooling fluid then flows from the inlet heat exchanger as pre-cooled cooling fluid 354 to the primary heat exchanger 310 to cool an object 390, wherein the cooling fluid expands through an expansion device 326 to reduce the temperature of the cooling fluid. In some cases, the cooling fluid reaches cryogenic temperatures and is a cryogenic refrigerant in the primary heat exchanger. The cooling fluid may then exit the primary heat exchanger and return to the inlet heat exchanger as return cooling fluid 327. The object 390 may be a solid or may be in thermal communication with a fluid, such as a supercritical fluid 380 that flows through a conduit 382. The supercritical fluid conduit may be the object that is cooled by the open loop cooling system and the supercritical fluid may be part of a flash chromatography system as described herein. The primary heat exchanger 310 may comprise one of more channels or conduits for the flow of the cooling fluid 350 therethrough, wherein the cooling fluid adsorbs heat from the object to be cooled. The channels or conduits may be machined in and along a conduit for a fluid, such as the supercritical fluid, to flow therethrough. In addition, the supercritical fluid may flow through the inner conduit of the tube-in-tube heat exchanger. The heat exchanger may be configured in a pump or portion of a pump. The cooling fluid passes through the inlet heat exchanger 360, wherein the inlet cooling fluid is cooled by return cooling fluid flowing back from the primary heat exchanger 310. The cooling fluid may be at a lower temperature after exiting the primary heat exchanger than the source cooling fluid 320 or pre-cooled cooling fluid 354 and therefore may be used to reduce the temperature of the source cooling fluid 320 in the inlet heat exchanger to produce the pre-cooled cooling fluid 354. The pre-heat exchanger may comprise a tube-in-tube heat exchanger, wherein the inlet conduit 322 or inner conduit, of the source cooling fluid 320 is within an outer tube or conduit of the return conduit 362 for the return cooling fluid 327. The cooling fluid may flow through the return conduit and then out an outlet 328 or vent. In this open loop cooling circuit 360, the cooling fluid is exhausted from the system. The pre-cooled cooling fluid 354 may then flow through an expansion device 326, such as an expansion valve wherein the temperature of the cooling fluid is reduced prior to flowing into the primary heat exchanger 310. In the primary heat exchanger, the cooling fluid absorbs heat from an object to be cooled 390, such as a fluid flowing through a conduit. In an exemplary embodiment, this fluid is a supercritical fluid that is used in a chromatography application. The primary heat exchanger may be a tube-in-tube heat exchanger, a plate and frame heat exchanger and the like. A controller 370 may incorporate a temperature sensor 372 for monitoring the temperature of the object to be cooled and a temperature controller 374 that regulates a valve 324 for the flow of cooling fluid through the open loop cooling system 300. The rate of flow of the cooling fluid through the expansion device 326 and into the primary heat exchanger 310 may be controlled by the control system 370. The fluid 380 flowing through the primary heat exchanger 310 may be chilled or reduced in temperature from the inlet 384 to the outlet 386 of the primary heat exchanger.

Figure 26:
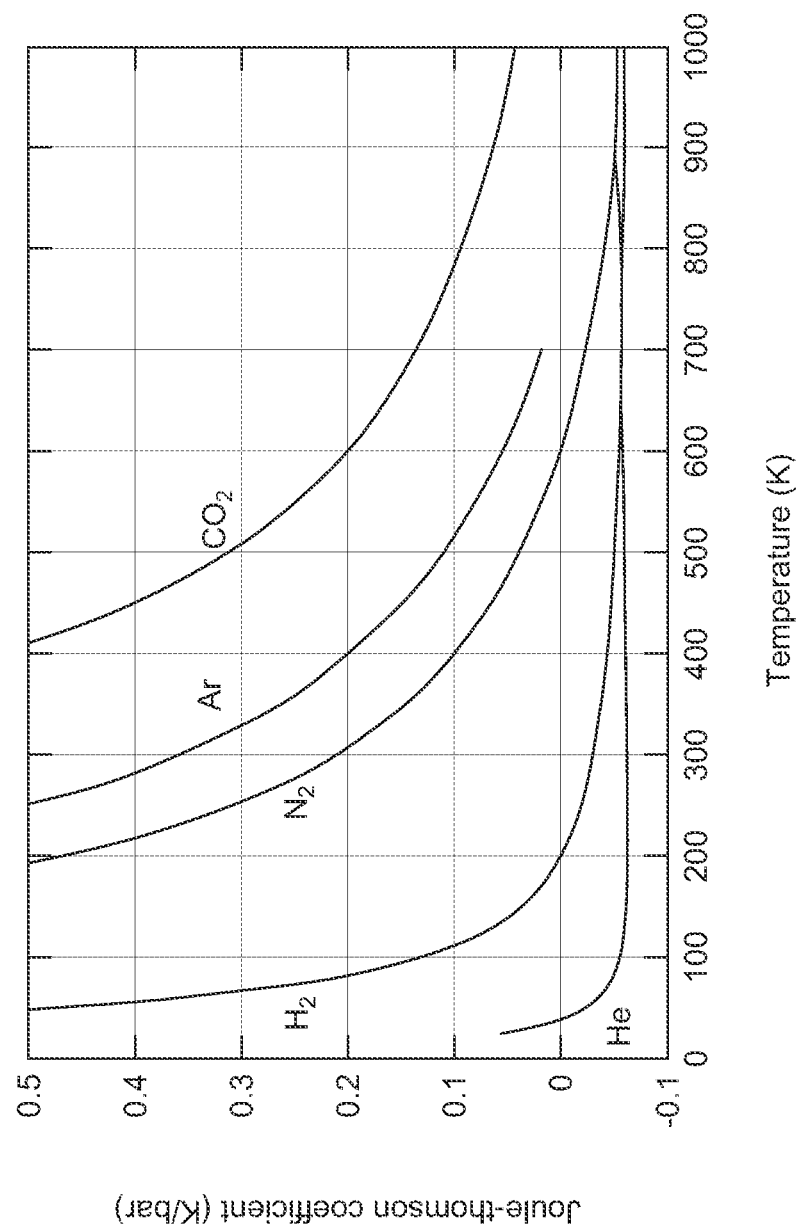
FIG. 26 shows a graph of exemplary refrigerants having a positive Joule Thomson coefficients.

FIG. 26 shows a graph of Joule-Thomson coefficients as a function of temperature for a number of fluids. As shown helium, hydrogen, nitrogen argon and carbon dioxide all have a positive Joule-Thomson coefficient over a wide range of temperatures including in the cryogenic temperature range.

Figure 27:
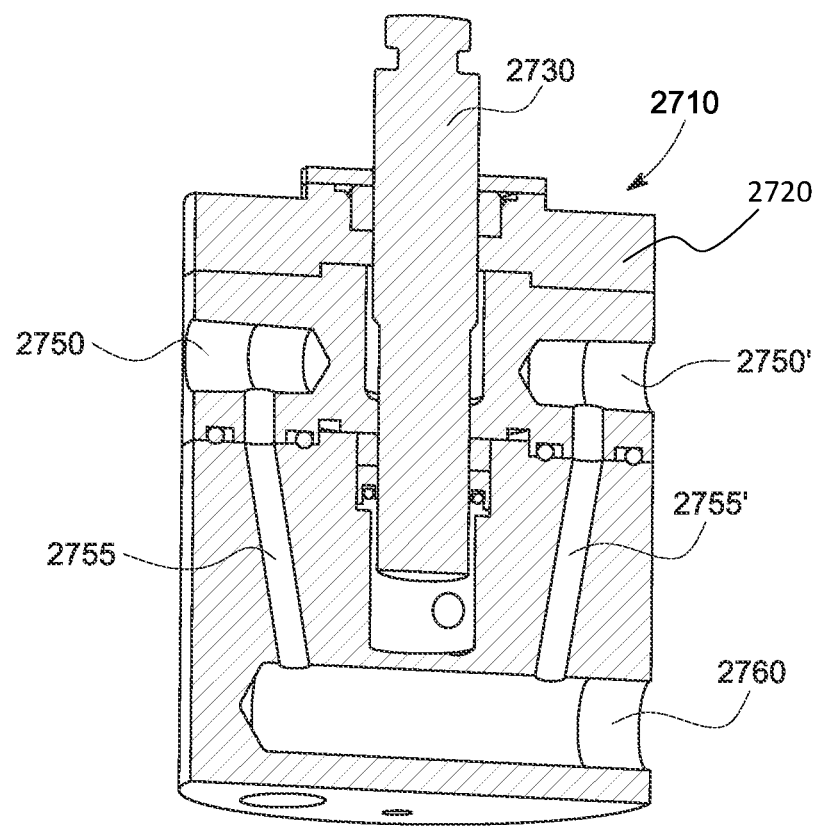
FIG. 27 shows a cross-sectional view of an exemplary primary heat exchanger incorporated into a pump.

As shown in FIG. 27, a primary heat exchanger 2710 is configured in a pump housing 2720. There are a plurality of inlets for the cooling fluid or refrigerant to cool the housing and a fluid pumped thereby. The refrigerant, such as a fluid having a positive Joule-Thomson coefficient may flow through an orifice 2750 and then expand into channels 2755 that extend along the pump housing, such as along the length of the pump head 2730. The orifice may be smaller than the channels. An exemplary orifice may have an opening that is about 0.10 mm (0.004 inches), and the channels may have a cross-length dimension or diameter of about 0.25 mm (0.010 inches). The refrigerant or cooling fluid may then exit the heat exchanger from a cooling fluid outlet 2760 as return cooling fluid that is used to cool source refrigerant or cooling fluid. Preferably, the cooling circuit may be configured with an orifice opening of 0.10 mm (0.004 inches), followed by a 0.010 inch orifice feeding into the channels in the pump head of the circuit, where the channels in the pump head are approximately 6 mm (0.25 inches) in diameter. Larger channels are also preferable as they have more area available for heat transfer. Alternatively, a capillary coil could be utilized for expansion, with the coil wrapped around a pump (or other device) needing cooling without modifying the device to have internal channels. The expansion ratio from an orifice opening to an orifice or channel for the Joule-Thomson fluid to expand is at least 2 to 1 and more preferably 5 to 1 to 10 to 1 or more.

What is claimed is:

1. A method of cooling via a circulator system utilizing the Joule-Thomson cooling effect of a fluid expanding through an expansion device located adjacent a pump head of a chiller pump to cool a refrigerant being pumped by the chiller pump, the method comprising:
    (a) introducing the refrigerant into the circulatory system from a source container holding the refrigerant at ambient temperature, the system comprising an inlet portion, a pressurized portion and an expansion portion;
    (b) flowing the refrigerant from the inlet portion, comprising the source container connected, via a circuit to the pressurized portion comprising a chiller pump;
    (c) pumping into the pressurized portion of the system the refrigerant supplied from the inlet portion through the chiller pump with a pump head, the chiller pump pumping at a speed sufficient to keep the refrigerant in continuous circulation through the pressurized portion at a continuous pressure of between 500 psi and 10,000 psi;
    (d) bringing the pressurized portion into fluid communication with a heat sink to allow heat to pass from a heated component external to the circulatory system, to the heat sink, and to the refrigerant circulating through the pressurized portion;
    (e) expanding a fluid in the expansion portion of the system through orifices of an expansion device located adjacent to the pump head of the chiller pump, the expansion device cooling the expanding fluid by virtue of the Joule-Thomson effect, the cooled fluid then cooling the pump head that in turn cools the refrigerant flowing into the pressurized portion from the chiller pump to a temperature between −5° C. and −30° C.

2. The method of claim 1, wherein the refrigerant is selected from the group consisting of hydrogen, nitrogen, argon, carbon dioxide.

3. The method of claim 1, wherein the fluid is the refrigerant.

4. The method of claim 1, wherein the fluid is the refrigerant and is supplied directly from the source container.

5. The method of claim 1, wherein the fluid is the refrigerant and is supplied from an outlet of the pressurized portion of the system.

6. The method of claim 1, wherein the refrigerant circulates through the system as a liquid and is maintained at a temperature that is warmer than the triple point temperature for the liquid.

7. The method of claim 1, wherein pressurized portion is configured to maintain a mass flow rate of between 10 milliliters per minute and 300 milliliters per minute of the refrigerant within the pressurized portion.

8. The method of claim 1, wherein pressurized portion is configured to maintain a mass flow rate of at least 50 milliliters per minute of the refrigerant within the pressurized portion.

9. The method of claim 1, wherein the system includes no more than one of said chiller pump.

10. The method of claim 1, wherein the system is configured to prevent the refrigerant from evaporating within the pressurized portion.

11. The method of claim 1, wherein the system is configured to prevent the refrigerant from forming condensate within the pressurized portion.

12. The method of claim 1, wherein the chiller pump is a piston-style positive displacement pump.

13. The method of claim 1, wherein the chiller pump is an HPLC—(High Pressure Liquid Chromatography-type) pump.

14. The method of claim 1, wherein the chiller pump is configured to pressurize the refrigerant within the pressurized portion to between 1,700 psi and 1,800 psi.

15. The method of claim 1, wherein the refrigerant within the pressurized portion is chilled at least 35° C. lower than the refrigerant in the source container.

16. The method of claim 1, wherein the expansion device contains at least one inlet orifice for fluid flow and at least one outlet orifice for fluid flow, and the expansion ratio between the at least one inlet orifice and the at least one outlet orifice is equal to or greater than 5 to 1.

17. The method of claim 1, wherein the refrigerant in the pressurized portion flows through a chromatographic column configured to allow the refrigerant to pass through a layer of stationary phase media to effectuate the separation of individual chemicals from a chemical mixture.

18. The method of claim 17, wherein internal and external pressure on the chromatographic column is balanced such that pressure differential on any wall separating the interior of the column from the exterior of the column is no greater than 200 psi.

19. The method of claim 5, wherein the system comprises an open loop cooling circuit configured to allow the fluid to be expelled from the circuit after passing through the expansion device.

* * * * *